US007041443B2

(12) United States Patent
Faaberg et al.

(10) Patent No.: US 7,041,443 B2
(45) Date of Patent: May 9, 2006

(54) PORCINE REPRODUCTIVE AND RESPIRATORY SYNDROME VIRUS AND METHODS OF USE

(75) Inventors: Kay S. Faaberg, Minneapolis, MN (US); Kurt D. Rossow, Roseville, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 322 days.

(21) Appl. No.: 10/203,224

(22) PCT Filed: Feb. 8, 2001

(86) PCT No.: PCT/US01/04351

§ 371 (c)(1),
(2), (4) Date: Aug. 7, 2002

(87) PCT Pub. No.: WO01/59077

PCT Pub. Date: Aug. 16, 2001

(65) Prior Publication Data

US 2003/0086945 A1 May 8, 2003

Related U.S. Application Data

(60) Provisional application No. 60/260,041, filed on Jan. 5, 2001, provisional application No. 60/215,373, filed on Jun. 29, 2000, provisional application No. 60/206,624, filed on May 24, 2000, provisional application No. 60/193,220, filed on Mar. 30, 2000, provisional application No. 60/181,041, filed on Feb. 8, 2000.

(51) Int. Cl.
*C12Q 1/70* (2006.01)
*C12Q 1/68* (2006.01)
*C07H 21/04* (2006.01)

(52) U.S. Cl. ........................... 435/5; 435/6; 536/24.33

(58) Field of Classification Search .................... 435/5, 435/6; 536/24.33
See application file for complete search history.

(56) References Cited

U.S. PATENT DOCUMENTS

| | | | | |
|---|---|---|---|---|
| 5,510,258 | A | 4/1996 | Sanderson et al. | 435/5 |
| 5,580,859 | A | 12/1996 | Felgner et al. | 514/44 |
| 5,620,691 | A | 4/1997 | Wensvoort et al. | 424/184.1 |
| 5,683,865 | A | 11/1997 | Collins et al. | 435/5 |
| 5,695,766 | A | 12/1997 | Paul et al. | 424/204.1 |
| 5,789,388 | A | 8/1998 | Visser et al. | 514/44 |
| 5,846,805 | A | 12/1998 | Collins et al. | 435/235.1 |
| 5,858,729 | A | 1/1999 | Van Woensel et al. | 435/71.1 |
| 5,976,537 | A | 11/1999 | Mengeling et al. | 424/184.1 |
| 5,998,601 | A | 12/1999 | Murtaugh et al. | 536/23.72 |
| 6,015,663 | A | 1/2000 | Wesley et al. | 435/5 |
| 6,110,467 | A | 8/2000 | Paul et al. | 424/204.1 |

FOREIGN PATENT DOCUMENTS

| | | |
|---|---|---|
| WO | 92/21375 | 12/1992 |
| WO | 93/02556 | 2/1993 |
| WO | 96/04010 | 2/1996 |
| WO | 96/40932 | 12/1996 |
| WO | 01/59077 | 8/2001 |

OTHER PUBLICATIONS

Larochelle et al. Veterinary Microbiology. 1997; 58: 1-8.*
Larochelle et al. Journal of Virological Methods. 1997; 63: 227-235.*
Abdallah et al., "Non-Viral Gene Transfer: Applications in Developmental Biology and Gene Therapy", *Biology of the Cell*, vol. 85, No. 1 (1995), pp. 1-7.
Ausubel, et al., "Current Protocols in Molecular Biology" vol. 1, (1994), *Table of Contents*.
Bautista et al., "Comparison of Porcine Alveolar Macrophages and CL 2621 for the Detection of Porcine Reproductive and Respiratory Syndrome (PRRS) Virus and Anti-PRRS Antibody", *Journal of Veterinary Diagnositic Investigation*, vol. 5, (1993) pp. 163-165.
Cavanagh et al., "Recommendations of the Coronavirus Study Group for the Nomenclature of the Structural Proteins, mRNAs, and Genes of Coronaviruses" *Virology*, vol. 176, (1990) pp. 306-307.
Christopher-Hennings et al., "Identification of Porcine Reproductive and Respiratory Syndrome Virus in Semen and Tissues from Vasectomized and Nonvasectomized Boars", *Veterinary Pathology*, vol. 35, No. 4, (1998) pp. 260-267.
Collins et al., "Isolation of Swine Infertility and Respiratory Syndrome Virus (Isolate ATCC VR-2332) in North America and Experimental Reproduction of the Disease in Gnotobiotic Pigs", *Journal of Veterinary Diagnositic Investigation*, vol. 4, No. 2, (1992) pp. 117-126.
de Antonio et al., "Quantitative Detection of Porcine Interferon-Gamma in Response to Mitogen, Superantigen and Recall Viral Antigen" *Veterinary Immunology and Immunopathology*, vol. 61, (1998) 265-277.
Donnelly et al., "Protective Efficacy of Intramuscular Immunization with Naked DNA", *Annuals New York Academy of Sciences DNA Vaccines: A New Era in Vaccinology*, vol. 772 (1995), pp. 40-46.
Graham et al., "Characteristics of a Human Cell Line Transformed by DNA from Human Adenovirus Type 5", *Journal of General Virology*, vol. 36, (1977) pp. 59-72.

(Continued)

*Primary Examiner*—Shanon Foley
(74) *Attorney, Agent, or Firm*—Mueting Raasch & Gebhardt, P.A.

(57) ABSTRACT

The present invention provides isolated European-like porcine reproductive and respiratory syndrome viruses, polynucleotides, and polypeptides. The present invention also provides methods for making antibodies to the viruses and polypeptides, methods for detecting porcine reproductive and respiratory syndrome viruses, immunogenic compositions, and methods for treating a porcine subject at risk of infection by, or displaying symptoms of, a porcine reproductive and respiratory syndrome virus infection.

6 Claims, 23 Drawing Sheets

OTHER PUBLICATIONS

Groot Bramel-Verheije et al., "Expression of a Foreign Epitope by Porcine Reproductive and Respiratory Syndrome Virus", *Virology*, vol. 278, (2000) pp. 380-389.

Halbur et al., "Comparative Pathogenicity of Nine US Porcine Reproductive and Respiratory Syndrome Virus (PRRSV) Isolates in a Five-Week-Old Cesarean-Derived, Colostrum-Deprived Pig Model", *Journal of Veterinary Diagnositic Investigation*, vol. 8, No. 1, (1996) pp. 11-20.

Halbur et al., "Immunohistochemical Identification of Porcine Reproductive and Respiratory Syndrome Virus (PRRSV) Antigen in the Heart and Lymphoid System of Three-Week-Old Colostrum-Deprived Pigs", *Veterinary Pathology*, vol. 32, No. 2, (1995) pp. 200-204.

Harlow et al., "Antibodies: A Laboratory Manual", Cold Spring Harbor Laboratory Press, Cold Spring Harbor (1988), *Table of Contents*.

Hsu et al., "Use of Avidin-Biotin-Peroxidase Complex (ABC) in Immunoperoxidase Techniques: A Comparison between ABC and Unlabeled Antibody (PAP) Procedures", *Journal of Histochemistry and Cytochemistry*, vol. 29, (1981) pp. 577-580.

Kapur et al., "Genetic Variation in Porcine Reproductive and Respiratory Syndrome Virus Isolates in the Midwestern United States", *Journal of General Virology*, vol. 77, No. 6, pp. 1271-1276.

Kim et al., "Enhanced Replication of Porcine Reproductive and Respiratory Syndrome (PRRS) Virus in a Homogeneous SUbpopulation of MA-104 Cell Line", *Archives of Virology*, vol. 133, (1993) pp. 477-483.

Kwang et al., "Antibody and Cellular Immune Responses of Swine Following Immunisation with Plasmid DNA including the PRRS Virus ORF's 4,5,6 and 7", *Short Communication. Research in Veterinary Science* (1999) vol. 67, pp. 199-201.

Lai, "Transcription, Replication, Recombination, and Engineering of Corona Virus Genes", *Advances in Experimental Medicine and Biology Corona- and related viruses*, vol. 380 (1995) pp. 463-472.

Lowrie et al., "DNA Vaccines Methods and Protocols", Humana Press, Totowa, NJ (2000). Xix p. 529: ill.; 24 cm.

Meulenberg et al., "Infectious Transcripts from Cloned Genome-Length cDNA of Porcine Reproductive and Respiratory Syndrome Virus" *Journal of Virology*, vol. 72, No. 1, (Jan. 1998) pp. 380-387.

Molling, "Naked DNA for Vaccine or Therapy", *Journal of Molecular Medicine*, vol. 75 (1997) pp. 242-246.

Murtaugh et al., "Comparison of the Structural Protein Coding Sequences of the VR-2332 and Lelystad Virus Strains of the PRRS Virus", *Archives of Virology*, vol. 140, No. 8, (1995) pp. 1451-1460.

Needleman et al., "A General Method Applicable to the Search for Similarities in the Amino Acid Sequence of Two Proteins", *Journal of Molecular Biology*, vol. 48, (1970) pp. 443-453.

Nelsen et al., "Porcine Reproductive and Respiratory Syndrome Virus Comparison: Divergent Evolution on Two Continents", *Journal of Virology*, vol. 73, No. 1 (Jun. 1999) pp. 270-280.

Nelson et al., "Differentiation of U.S. and European Isolates of Porcine Reproductive and Respiratory Syndrome Virus by Monoclonal Antibodies", *Journal of Clinical Microbiology*, vol. 34, (1993), pp. 3184-3189.

Pardoll et al., "Exposing the Immunology of Naked DNA Vaccines", *Immunity*—Cambridge, MA, vol. 3, No. 2 (1995) pp. 165-169.

Park et al., "Pathogenesis of Plaque Variants of Porcine Reproductive and Respiratory Syndrome Virus in Pregnant Sows", *American Journal of Veterinary Research*, vol. 57 (1996) pp. 320-323.

Rossow et al., "Pathogenesis of Porcine Reproductive and Respiratory Syndrome Virus Infection in Gnotobiotic Pigs", *Veterinary Pathology*, vol. 32, No. 4, (1995) pp. 361-373.

Rossow, "Porcine Reproductive and Respiratory Syndrome", Review Article. *Veterinary Pathology*, vol. 35 (1998) pp. 1-20.

Sambrook et al., Molecular Cloning: A Laboratory Manual., Second Edition, Cold Spring Harbor Laboratory Press, vol. 3: ill.: 28 cm. (1989).

Smith et al., "Immunofluorescence in the Diagnosis of Bovine Fetal Leptospirosis", *The Cornell Veterinarian*, vol. 57 (1967) pp. 517-526.

Stevenson et al., "Idiotypic DNA Vaccines Against B-cell Lymphoma", *Immunology Reviews*, vol. 145 (1995) pp. 211-228.

Terpstra et al., "Experimental Reproduction of Porcine Epidemic Abortion and Respiratory Syndrome (Mystery Swine Disease) by Infection with Lelystad Virus: Koch's Postulates Fulfilled", *The Veterinary Quarterly*, vol. 13, (1991) pp. 131-136.

vanNieuwstadt et al., "Proteins Enclosed by Open Reading Frames 3 and 4 of the Genome of Lelystad Virus (Arteriviridae) Are Structural Proteins of the Virion", *Journal of Virology*, vol. 70, No. 7, (1996) pp. 4767-4772.

Vogel et al., "Nucleic Acid Vaccines" *Clinical Microbiology Reviews*, vol. 8, No. 3 (1995) pp. 406-410.

Wensvoort et al., "Mystery Swine Disease in the Netherlands: The Isolation of Lelystad Virus", *The Veterinary Quarterly*, Vol. 13, (1991) pp. 121-130.

Yang et al., "Developing Particle-Mediated Gene Transfer Technology for Research into Gene Therapy of Cancer", *Molecular Medicine Today*, vol. 2, No. Ref. (1996) pp. 476-481.

Yoon et al., "An Indirect Fluorescent Antibody Test for the Detection of Antibody to Swine Infertility and Respoiratory Syndrome Virus in Swine Area" *Journal of Veterinary Diagnostic Investigation*, vol. 4 (1992) pp. 144-147.

Yuan et al., "Recombination beween North American Strains of Porcine Reproductive and Respiratory Syndrome Virus", Dept. of Veterinary PathoBiology, University. of Minnesota. Received Feb. 1, 1999; Received in Revised from Mar. 17, 1999; Accepted Mar. 22, 1999, Virus Research 61 (1999) pp. 87-98.

* cited by examiner

Fig. 1A

SEQ ID NO: 1

```
         1                   21                  41                  61
1: CTTGTTGTGGGAGGAACTCCCGAGAGGATTTTCGGAGAGGACCTGCTTACTGGATGTTCACCCTTTAACCATGTGTGGGAGCGTCTCCCGGTGCATGTGC
2:         . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . .
3:           L  W  G  G  T  P  E  D  F  R  R  G  P  A  L  L  D  V  H  P  L  T  M  C  G  S  V  S  R  C  M  C

SEQ ID NO: 2
         101                 121                 141                 161                 181
1: ACCCCGGCTGTCCGGGTATTTTGGAACGCCGGCCAAGTCTTTTGCACACGGTGTCAGTGCGCGGGTCTTCTCTCTCCAGAGCTTCAGGACACTGACC
2:         . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . .
3:    T  P  A  V  R  V  F  W  N  A  G  Q  V  F  C  T  R  C  V  S  A  R  A  L  L  S  P  E  L  Q  D  T  D 201                 221                 241                 261                 281
1: TCGGTGCGGTTGGATTGTTTTACAGGCCTAGGATAAGCTACACTGGAAAGTCCCTATCGGCATCCCCAGGCGGAATGTACTCCATCCGGTGCTGTTG
2:         . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . .
3:    L  G  A  V  G  L  F  Y  R  P  R  D  K  L  H  W  K  V  P  I  G  I  P  Q  A  E  C  T  P  S  G  C  W 301                 321                 341                 361                 381
1: GCTCTCTCAGCTGTATTCCCTTTGGCGCGCAGCCTCTGGCAATCACAACTTCCTTCAACGACTTGTTAAGGTTGCTGATGTTTTGTACCGTGACGGTTGC
2:         . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . .
3:    L  S  A  V  F  P  L  A  R  M  T  S  G  N  H  N  F  L  Q  R  L  V  K  V  A  D  V  L  Y  R  D  G  C 401                 421                 441                 461                 481
1: CTGGCACCTGACACTCCGTGAGCTTCAAGTTTACGAGGCGGCTGCAATGGTACCCAATCACGGGGCCCGTACCCGGGATGGGTTTGTTGCGAATT
2:         . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . .
3:    L  A  P  R  H  L  R  E  L  Q  V  Y  E  R  G  C  N  W  Y  P  I  T  G  P  V  P  G  M  G  L  F  A  N 501                 521                 541                 561                 581
1: CCATGCACGTATCCGACCAGCCGTTCCCTGGTGCCACCCATGTGTTGACTAACTCTGTTGACTAACTCGCCTTGACTGCTGCGCAACCGGTGTCGGCAACCGTTCTGTCCATTTGA
2:         . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . .
3:    S  M  H  V  S  D  Q  P  F  P  G  A  T  H  V  L  T  N  S  P  L  P  Q  Q  A  C  R  Q  P  F  C  P  F  E 601                 621                 641                 661                 681
1: GGAAGCTCATTCTGGCTGTGTATAGGTGTGTATAGGTGGAAGAAATTGTAATTTTTTCGGACTCCCCTCCAACGGCCAATCTCGCATTATGTGGACGCCGAAATCCGAT
2:         . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . .
3:    E  A  H  S  G  V  Y  R  W  K  K  F  V  I  F  S  D  S  P  L  N  G  Q  S  R  I  M  W  T  P  K  S  D
```

Fig. 1B

```
                  721                             741                             761                             781
1: GATTCAGCTGCTCTGGAGGAACTACCGCCTGAGTTAGAGAACGTCAGTTGAAATTCTCATTCGGAGTTTCCCTGCTCATCACCCTGTCAACCTGGCGGACT
2: ..D..S..A..A..L..E..E..L..P..P..E..E..L..E..R..Q..V..E..I..L..I..R..S..F..P..A..H..H..P..V..N..L..A..D..
3: ............................................................................................................

801                             821                             841                             861                             881
1: GGGAGCTCACTGGGTCTCCTGAGAACGGTTTTTCCTTCAACACGTCTCATTCTTGCGTCCGAAACTCCAACGTGTTTGATGGCAAGTGCTG
2: ..W..E..L..T..G..S..P..E..N..G..F..S..F..N..T..S..H..S..C..G..H..L..V..R..N..S..N..V..F..D..G..K..C..W..
3: ............................................................................................................

901                             921                             941                             961                             981
1: GCTCACCTGCTTTTTGGGCCAGTCGGTCGAAGTGCGCTCGAAGAACATCTAGCCAACGCCCTTCGTTACCAAACCAAGTGGGGCGTGCACGGTAAG
2: ..L..T..C..F..L..G..Q..S..V..E..V..R..C..H..E..E..H..L..A..N..A..F..G..Y..Q..T..K..W..G..V..H..G..K..
3: ............................................................................................................

1001                            1021                            1041                            1061
1: TACCTTCAACGCAGGCTTCAAGTTCGGGGCATTCGTGCTGTAGTGGATCCTGACGGCCCATTCACGTTGAAGCGCTGTCTGCTCCCAGTCTTGGATCA
2: ..Y..L..Q..R..R..L..Q..V..R..G..I..R..A..V..V..D..D..P..D..G..P..I..H..V..E..A..L..S..C..S..Q..S..W..I..
3: ............................................................................................................

1101                            1121                            1141                            1161                            1181
1: GGCACCTGACCCTGAATGACGATCACCCCAGGATTTGTTCGCCTGACATCCATTCGACATTGTGCCGAATACAGAGCCTACCACTTCCCAGATCTTTCG
2: ..R..H..L..T..L..N..D..D..V..T..P..G..F..F..V..R..L..T..S..I..R..I..V..P..N..T..E..P..T..T..S..Q..I..F..R..
3: ............................................................................................................

1201                            1221                            1241                            1261                            1281
1: ATTTGGAGCGCATAAGTGGTATGGCGCGGTAAAGCGCAAGCGCACGGCTCGTGCCAAGCGTACCGCTAAAGGTGGGAAGGATTCTGTTCCCGCTCTCAAGGTTGCC
2: ..F..G..A..H..K..W..Y..G..A..A..G..K..R..A..K..R..T..A..K..G..G..K..D..S..V..P..A..L..K..V..A..
3: ............................................................................................................

1301                            1321                            1341                            1361                            1381
1: CTGCCCGGTCCCCGCCTGTGAATAACCACCTATTCCCGACACCGACAGACGGGTCTTGTGTTGGCATGTCCTTGCCGCCATAATGAACGGATGATGAACG
2: ..L..P..V..P..A..C..G..I..T..T..Y..S..P..P..T..D..G..S..C..G..W..H..V..L..A..A..I..M..N..R..M..M..N..
3: ............................................................................................................
```

Fig. 1C

```
     1401                                              1461
1: ATGACTTCACGTCCCCTCTGACTCAGTACAACAGACCAGAGGATGATTGGGCTTCAGATTATGATCTTGCTCAGGCGATTCAATGTCTACAACTACCTGC
2: ..D  D  F  T  S  P  L  T  Q  Y  N  R  P  E  D  D  W  A  S  D  Y  D  L  A  Q  A  I  Q  C  L  Q  L  P  A
3:

1501                                              1561
1: TACCGTGGTTCGGAATCGCGCTTGTCCTAACGCCAAGTACCTTTATAAAACTTAACGGGGTTCACTGGGAGGTAGAGTTGAGATCTGGAATGGCTCCTCGC
2: ..T  V  V  R  N  R  A  C  P  N  A  K  Y  L  I  K  L  N  G  V  H  W  E  V  E  V  R  S  G  M  A  P  R
3:

1601                                              1661
1: TCCCTTTCTCGTGAATGTGTGGTCGGCGTTTGTTCTGAAGGCTGCGTCGCGCCGCCCTTACCCAGCGGATGGGCTTCCTAAGCGTGCACTCGAGGCCTTGG
2: ..S  L  S  R  E  C  V  V  G  V  C  S  E  G  C  V  A  P  P  Y  P  A  D  G  L  P  K  R  A  L  E  A  L
3:

1701                                              1761
1: CGTCTGCTTACAGACTACCCTCCGATTGTGTTGCTCTGGTATTGCTGACTTTCTTGCCAATCCACTCCCTCAAGAATTCTGGACTCTCGACAAAATGTT
2: ..A  S  A  Y  R  L  P  S  D  C  V  C  S  G  I  A  D  F  L  A  N  P  P  P  Q  E  F  W  T  L  D  K  M  L
3:

1801                                              1861
1: GACCTCCCCGTCACCAGAACGGTCCGGCTTCTCTAGTTTGTATAAACTTGCTATTAGAGTTGTTCCGCAAAAATGCGGTGTCACGGAAGGGCCTTCACC
2: ..T  S  P  S  P  E  R  S  G  F  S  S  L  Y  N  L  L  L  E  V  V  P  Q  K  C  G  V  T  E  G  A  F  T
3:

1901                                              1961
1: TATGCTGTTGAGAGGATGTTAATGGATTGTCCGAGCTCCGAACAGGCCATGGCTCTTCTCGGCAAAAATTAAAGTTCCATCCTCAAAGGCCCCATCTGTGT
2: ..Y  A  V  E  R  M  L  M  D  C  P  S  S  E  Q  A  M  A  L  L  A  K  I  K  V  P  S  S  K  A  P  S  V
3:

2001                                              2061
1: CCTTGGACGAGTGTTTCCCTGCAGATGTTCCGGCCGATTCGAGCCAACGTCTCAGAAAAGCCCCAAAGTTCCGGCCGCTGCCCTGTTCATC
2: ..S  L  D  E  C  F  P  A  D  V  P  A  D  F  E  P  T  S  Q  K  R  P  Q  S  S  G  A  A  V  A  L  C  S
3:
```

*Fig. 1D*

```
     2101                                        2141                                        2181
     GGATGCAGAGAAGGGTTCGAGGAAGCAGCCCCAGAAGGAAGCAGGAGTTCAAGAGAGAGGCCATAAGGCCGTCCACTCTTGCACTCTTTGCCAAGGTCCAAATAACGAA
1:  ..D  A  E  G  F  E  E  A  A  P  E  G  V  Q  E  R  G  H  K  A  V  H  S  A  L  F  A  K  G  P  N  N  E   ..
2:  ..                                                                                                      ..
3:  ..                                                                                                      ..

2201                                        2241                                        2281
     CAGGTACAGAGGTGGTTGCCGGTGAGCAACAGAAGCTCGGGCGGTTGTGTTTGGCAATCGGGAATGCTCAGTCCCCTTTAAATTCCATGAAAGAAAAACATGC
1:  ..Q  V  Q  V  V  A  G  E  Q  Q  K  L  G  G  C  G  L  A  I  G  N  A  Q  S  P  L  N  S  M  K  E  N  M   ..
2:  ..                                                                                                      ..
3:  ..                                                                                                      ..

2301                                        2341                                        2381
     GCAGTAGCCGGGAGAGACGAACCACTGGATTTGTCCCAACCAGCACCAGTTGCCGCAACGACCCTTGAGAGAGAGCAAACACCCGATAACCCAGGTTCTGA
1:  ..R  S  S  R  E  D  E  P  L  D  L  S  Q  P  A  P  V  A  A  T  T  L  E  R  E  Q  T  P  D  N  P  G  S  D   ..
2:  ..                                                                                                      ..
3:  ..                                                                                                      ..

2401                                        2441                                        2481
     TGCCGGTGCCCTCCCCGCCACCGTTCGAGAATCTGTCCCGACAGGGCCTATGCTCCGTCATGTTGAGCACTGTGGCACGGAGTCTGGCGATAGCAGTTCG
1:  ..A  G  A  L  P  A  T  V  R  E  S  V  P  T  G  P  M  L  R  H  V  E  H  C  G  T  E  S  G  D  S  S  S   ..
2:  ..                                                                                                      ..
3:  ..                                                                                                      ..

2501                                        2541                                        2581
     CCTTTGGATCTGTCTTATGCGCAAACTTTGGACCAGCCTTTAGATCTATCCCTGGCCGTTGGCCGTGAAGGCCACGCCTTTCAGTTCGGGAAGCTTTCTGAGTCCGGCTCTGTCAT
1:  ..P  L  D  L  S  Y  A  Q  T  L  D  Q  P  L  D  L  S  L  A  V  W  P  V  K  A  T  A  S  D  P  G  W  V   ..
2:  ..                                                                                                      ..
3:  ..                                                                                                      ..

2601                                        2641                                        2681
     ACGGTAGGCGCGAGCCTGTCTTTGTAAAGCCTCGAAAAGCTTTCTCTGATAGCGACTCAGCCTTTCAGTTCGGGAAGCTTTCTGAGTCCGGCTCTGTCAT
1:  ..H  G  R  R  E  P  V  F  V  K  P  R  K  A  F  S  D  S  D  S  A  F  Q  F  G  K  L  S  E  S  G  S  V  I   ..
2:  ..                                                                                                      ..
3:  ..                                                                                                      ..

2701                                        2741                                        2781
     TGAGTTTGACCGAACAAAAGATGCTCCGGTTGTTGACGCCCCCGTGGCTCGACGACTTGTCTATAGCCGATCCTTTGAATTTGCC
1:  ..E  F  D  R  T  K  D  A  P  V  V  D  A  P  V  G  S  T  T  S  N  E  A  L  S  I  A  D  P  F  E  F  A   ..
2:  ..                                                                                                      ..
3:  ..                                                                                                      ..
```

Fig. 1E

```
      2801                        2821                        2841                        2861                        2881
      GAACTCAAGCGCCCGGCTTCTCCGCACAAGCCTTCCGCGTTTCTCCGCACAAGCCTTCGCGCCGAGGGCGGTCCGCGATGTCCATGCCGATGTCCGAAAATAAAGAACCGGGTGTATGAACGGT ....
1:    E  L  K  R  P  R  F  S  A  Q  A  L  I  D  R  G  G  P  L  A  D  V  H  A  K  I  K  N  R  V  Y  E  R
2:
3:

2901                        2921                        2941                        2961                        2981
      GCCTCCAAGCTTGTGAGCCCGGTAGTCGTGCAACCCCAGCCACCAAGGAGTGGCTCGACAAGATGTGGGATAGGGTGGACATGAAAACTTGGTGCTGCAC ....
1:    C  L  Q  A  C  E  P  G  S  R  A  T  P  A  T  K  E  W  L  D  K  M  W  D  R  V  D  M  K  T  W  C  C  T
2:
3:

3001                        3021                        3041                        3061                        3081
      CTCGCCAGTTCCAAGCTGTGGTCGCATTCTTGCGTCCCTCAAATTCCTCCCTGACATGATTCAAGACACACCGCTCCTGTTCCCAGGAAGAACCGAGCTAGT ....
1:    S  Q  F  Q  A  G  R  I  L  A  S  L  K  F  L  P  D  M  I  Q  D  T  P  P  P  V  P  R  K  N  R  A  S
2:
3:

3101                        3121                        3141                        3161                        3181
      GACAATGCCGATCTGAAGCAACTGGTGGCACAGTGGGATAGGAAATTGACTATGAACCCCTCCCAAAAAACCGGTTGAGCCAGTGCTTGACCAGACCGTCT ....
1:    D  N  A  D  L  K  Q  L  V  A  Q  W  D  R  K  L  S  M  T  P  P  Q  K  P  V  E  P  V  L  D  Q  T  V
2:
3:

3201                        3221                        3241                        3261                        3281
      CTCCGCCTACGGATACTCAGCAAGAAGATGTGACCCCCTCCGATGGGCCACCCATGCGCCGGATTTCCCAGTCGTGTGAGCACGGGCGGGAGTTGGAA ....
1:    S  P  P  T  D  T  Q  Q  E  D  V  T  P  S  D  G  P  P  H  A  P  D  F  P  S  R  V  S  T  G  G  S  W  K
2:
3:

3301                        3321                        3341                        3361                        3381
      AGACCCTTATGTGTTCCGGCGGTCTATGCTCAGTCAGCGCCCTCATGACATGGGTTTTTTGAAGTTTTCTCCCACCTCCCAGCCTTTATGCTC ....
1:    D  L  M  C  S  G  T  R  L  A  G  S  I  S  Q  R  L  M  T  W  V  F  E  V  F  S  H  L  P  A  F  M  L
2:
3:

3401                        3421                        3441                        3461                        3481
      ACACTTTTCTCGCCGGGCGGCTCTATGGCTCCAGTGATTGGTTGTTTGTTTGCAGTGTGTTGTTTGCAGTGTGTGTTGTTTGCAGTGTGTTACTTGCTCTGTTCATTCTTACCCGATACTCG ....
1:    T  L  F  S  P  R  G  S  M  A  P  G  D  W  L  F  A  G  V  V  L  A  L  L  L  C  H  S  Y  P  I  L
2:
3:
```

Fig. 1F

```
       3501                3521                3541                3561                3581
    GGTGCCTTCCCTTATTGGGTGTCTTTTCTGGTTCGTCTGGGTGTTGTTCGCGGGTGTTGTTCTTTGCGCGCTGTTCTTTGGATGCCTTTTGCTGTATTTTATTCTCGAC
1:                                                                                                        .
2:  ..G  C  L  P  L  L  G  V  F  S  G  S  L  R  R  V  R  L  G  V  F  G  S  W  M  A  F  A  V  F  L  F  S  T..
3:

3601                3621                3641                3661                3681
    TCCATCCAACCCAGTCGGTTCTTCTTCTTGTGACCACGATTCGCCGGAATGTCATGCTGAGCTTTGGCTCTCTGAGCAGCGCCAACTTTGGAACCTGTGCGC
1:                                                                                                        .
2:  ..P  S  N  P  V  G  S  S  C  D  H  D  S  P  E  C  H  A  E  L  L  A  L  E  Q  R  Q  L  W  E  P  V  R..
3:

3701                3721                3741                3761                3781
    GGCCTTGTGGTCGGCCCCTCGGGCCCTCTTATGTGTCATTCTTGGCAAGTTACTCGGTGGGTCACGTTATCTCGGCATATTCTCCTACGTTATGCATGC
1:                                                                                                        .
2:  ..G  L  V  V  G  P  S  G  L  L  C  V  I  L  G  K  L  L  G  G  S  R  Y  L  W  H  I  L  L  R  L  C  M..
3:

3801                3821                3841                3861                3881
    TTACAGATTGGCCCTTTCTCTTGTTGTTTATGTGGTATGTGTCCCAAGGGCCGTTGTCACAAGTGTTGGGGAAAGTGTATAAGAACAGTCCTACTGAGGTGGCTCT
1:                                                                                                        .
2:  ..L  T  D  L  A  L  S  L  V  Y  Y  V  V  S  Q  G  R  C  H  K  C  W  G  K  C  I  R  T  A  P  T  E  V  A  L..
3:

3901                3921                3941                3961                3981
    TAATGTGTTCCCTTTCACGCGCGCACCCCGTTCCTCTCTTGTATCCTTGTGTGATTCGATGATTGATCCTGTGCACTTGGCAACG
1:                                                                                                        .
2:  ..N  V  F  P  F  T  R  A  T  R  S  S  L  V  S  L  C  D  R  F  Q  T  P  K  G  V  D  P  V  H  L  A  T..
3:

4001                4021                4041                4061                4081
    GGTTGGCCGCGGGTGCTGGCGTGGTGGGAGTCCCGTCCATCAACCACCACCAAAAGCCCATTGCTTATGCCAACTTGGATGAAAAGAAAATATCTGCCCAAA
1:                                                                                                        .
2:  ..G  W  R  G  C  W  R  G  G  S  P  V  H  Q  P  H  Q  K  P  I  A  Y  A  N  L  D  E  K  K  I  S  A  Q..
3:

4101                4121                4141                4161                4181
    CGGTGGTTGCCGTCCCATACGATCCCAGTCAGGCCATCAAATGCCTGAAAGTTCTGCAGGGCGGGAGGGCTATCGTGGACCAGCCTACACCTGAGGTTGT
1:                                                                                                        .
2:  ..T  V  V  A  V  P  Y  D  P  S  Q  A  I  K  C  L  K  V  L  Q  A  G  G  A  I  V  D  Q  P  T  P  E  V  V..
3:
```

Fig. 1G

```
         4201                        4221                        4241                        4261                        4281
  1: TCGTGTGTCCGAAATCCCCTTCTCAGCTCCATTTTTTCCAAAAGTTCCAGTCAACCCAGAGATTGCAGAGAGTCGTGGTAGAGATTCGGACACTTTTGTGGCTGCCG
  2:    R  V  S  E  I  P  F  S  A  P  F  F  F  P  K  V  P  V  N  P  D  C  R  V  V  D  S  D  T  F  V  A  A
  3:

4301                        4321                        4341                        4361                        4381
  1: GTTCGATGCGGTTACTCGACAGCACAACTTGTCTTGGGCCAGGCAACTTTGCCAAGTTGAATCAGACCCCCCCAGGAACTCCACTTCCACCAAAACGA
  2:    V  R  C  G  Y  S  T  A  Q  L  V  L  G  Q  G  N  F  A  K  L  N  Q  T  P  P  R  N  S  T  K  T
  3:

4401                        4421                        4441                        4461                        4481
  1: CTGGTGGGGCCTCTTACACCCTTGCTGTGTGCTCAAGTAACTGTGTGGACTCTTTTTCATTCATTTCATTGGTTTACATCACCTCAAGTGTGTGG
  2:    L  V  G  A  S  Y  T  L  A  V  A  Q  V  T  V  W  T  L  F  H  F  I  L  G  L  W  F  T  S  P  Q  V  C  G
  3:

4501                        4521                        4541                        4561                        4581
  1: CCGAGGAACCGCTGACCCATGGTGTTCAAATCCTTTTTCATACCCCACCTATGGCCCTGGAGTTGTGTGCTCCTCTCGGCTTTGCTGCTCTGCCGACGGG
  2:    R  G  T  A  D  P  W  C  S  N  P  F  S  Y  P  P  T  Y  G  P  G  V  V  C  S  S  R  L  C  V  S  A  D  G
  3:

4601                        4621                        4641                        4661                        4681
  1: GTCACCTTGCCATTGTTCTCAGCCGTGGCACAACTTTCCGGTAGAGAGGTGGGGATCTTTATTTTGGTGCTCGTTTCCTTGATTGCCTTGGCCCACCGTA
  2:    V  T  L  P  L  F  S  A  V  A  Q  L  S  G  R  E  V  G  I  F  I  L  V  L  V  S  L  I  A  L  A  H  R
  3:

4701                        4721                        4741                        4761                        4781
  1: TGGCTCTTAAGGCAGACATGTTAGTCGTCTTTTTGGCTTTTTGTGCTTACGCCTGGCCTATGAGCTCCTGGTAATTGCTTCTTCTTTCCCTTACTCTTGAA
  2:    M  A  L  K  A  D  M  L  V  V  F  L  A  F  C  A  Y  A  W  P  M  S  S  W  L  I  C  F  F  P  L  L  L  K
  3:

4801                        4821                        4841                        4861                        4881
  1: GTGGGTCACCCTTCACCCTCTCACCATGCTTTGGGTGCACTCATTCTTGGTGTTTGTCTGCCAGCGCGGCCATCCTCTCATTAGGGACAACTGGCCTT
  2:    W  V  T  L  H  P  L  T  M  L  W  V  H  S  F  L  V  F  C  L  P  A  A  G  I  L  S  L  G  T  T  G  L
  3:
```

Fig. 1H

```
         4901                        4921                        4941                        4961                        4981
1:  CTCTGGGCAATTGGCCGCTTTACCCAGGTTGCCGGAATTATTACACCTTATGACATCCACCAATACACCTCTGGGCCACGTGGTGCAGCTGCTGTGGCCA
2:
3:  .. L  W  A  I  G  R  F  T  Q  V  A  G  I  I  T  P  Y  D  I  H  Q  Y  T  S  G  P  R  G  A  A  A  V  A ..

5001                        5021                        5041                        5061                        5081
1:  CAGCCCCAGAAGGCACTTATATGGCCGCCGTCCGGAGAGCTGCTTTAACTGGGCGAACTTTAATCTTCACCCGTCTGCAGTTGGATCCCTTCTCGAAGG
2:
3:  .. T  A  P  E  G  T  Y  M  A  A  V  R  R  A  A  L  T  G  R  T  L  I  F  T  P  S  A  V  G  S  L  L  E  G ..

5101                        5121                        5141                        5161                        5181
1:  TGCCTTCAGGACTCAAAAAACCCTGCCTTAACACCGTGAATGTTGTAGGCTCTCTTCCCTTGGTTCCGGAGGGGTTTTCACCATTAACGGCAGAAGGACTGTC
2:
3:  .. A  F  R  T  Q  K  P  C  L  N  T  V  N  V  V  G  S  S  L  G  S  G  G  V  F  T  I  N  G  R  R  T  V ..

5201                        5221                        5241                        5261                        5281
1:  GTCACTGCTGCTCATGTGTTGAACGGTGACACAGCTAGAGTCACCGGCGACTCCTACAACGCATGCACTTTCAAGACCAATGGTGATTATGCCTGGT
2:
3:  .. V  T  A  A  H  V  L  N  G  D  T  A  R  V  T  G  D  S  Y  N  R  M  H  T  F  K  T  N  G  D  Y  A  W ..

5301                        5321                        5341                        5361                        5381
1:  CCCATGCTGATGACTGGCAGGGCGTTGCTCCTGTGGTCAAGGTTGCGAAGGGGTACCGCGGTCGTGCCTACTGGCAAACATCAACTGGTGTCGAACCCGG
2:
3:  .. S  H  A  D  D  W  Q  G  V  A  P  V  V  K  V  A  K  G  Y  R  G  R  A  Y  W  Q  T  S  T  G  V  E  P  G ..

5401                        5421                        5441                        5461                        5481
1:  CATTATTGGGGAAGGTTCGCCTTCTGCTTCTTCACCAACTGTGGCGATTCAGGGTCACCTGTTATCTCAGAATCTGGTGATCTCATTGGAATCCACACTGGT
2:
3:  .. I  I  G  E  G  F  A  F  C  F  F  T  N  C  G  D  S  G  S  P  V  I  S  E  S  G  D  L  I  G  I  H  T  G ..

5501                        5521                        5541                        5561                        5581
1:  TCAAACAAACTCGGTTCTGTCTTGTGGTCTTGTGACGACCCCTGAAGGGGAGACCTGCGCCATCAAAGAAACCAAGCTCTCTGACCTTTCCAGACATTTGCAGGCC
2:
3:  .. S  N  K  L  G  S  G  L  V  T  T  P  E  G  E  T  C  A  I  K  E  T  K  L  S  D  L  S  R  H  F  A  G ..
```

Fig. 1I

```
         5601                        5621                        5641                        5661                        5681
      1: CGAGCGTTCCTCCTTGGGGACATTAAGTTGAGTCCGGCCATTCCGAGTGACTTGGCATCGCTCCTCCGTCCCTGT
      2:    P  S  V  P  L  G  D  I  K  L  S  P  A  I  I  P  D  V  T  S  I  P  S  D  L  A  S  L  L  A  S  V  P  V
      3:

5701                        5721                        5741                        5761                        5781
      1: ATTGGAAGGCGGCCTCTCGACCGTCCAACTTCTGTGTGTCTTTTTTCCTCCTCTGGCGCATGATGGGCCATGTCGCCGTGGGCTTC
      2:    L  E  G  G  L  S  T  V  Q  L  L  C  V  F  F  L  L  W  R  M  M  G  H  A  W  T  P  I  V  A  V  G  F
      3:

5801                        5821                        5841                        5861                        5881
      1: TTTCTACTAAATGAAATCCTTCCAGCAGTTTTGGTGTCCGAGCCGTGTTTCTTGTGCTTGCATGGGTCACCCCTGGTCTCGCCAGGTGT
      2:    F  L  L  N  E  I  L  P  A  V  L  V  R  A  V  F  S  F  A  L  F  V  L  A  W  V  T  P  W  S  A  Q  V
      3:

5901                        5921                        5941                        5961                        5981
      1: TGATGATTAGGCTCCTCACGGCATCTCTCAACCGCAACAAGTTCTCTCTGGCGTTCTACGCCACTCGGGGTGTCATCGGTTGGCCGCTGAAATTGGGAC
      2:    L  M  I  R  L  L  T  A  S  L  N  R  N  K  F  S  L  A  F  Y  A  L  G  G  V  I  G  L  A  A  E  I  G  T
      3:

6001                        6021                        6041                        6061                        6081
      1: TTTTGCTGGTAGACTGCCTGAATTGTCTCAAGCCCTTTCGACATACTGTTTCTTACTAGGTTCTTGCCATGGCCAGTTGTGTTCCATCATCATCATT
      2:    F  A  G  R  L  P  E  L  S  Q  A  L  S  T  Y  C  F  L  P  R  V  L  A  M  A  S  C  V  P  I  I  I  I
      3:

6101                        6121                        6141                        6161                        6181
      1: GGTGGACTCCATACCCTCGGTGTGATTCTGTGGTTGTTCAAATACCGGTGCCTCCACAACATGCTGGTTGGTGATGGGAGTTTTCAAGCGCCTTCTTCC
      2:    G  G  L  H  T  L  G  V  I  L  W  L  F  K  Y  R  C  L  H  N  M  L  V  G  D  G  S  F  S  S  A  F  F
      3:

6201                        6221                        6241                        6261                        6281
      1: TACGGTATTTGCAGAGGGTAATTTGAGAAAAGGTGTTTCACAGTCCTGTGGCATGAATAACGAGTCCCTGACGGCTGCTTGCAAGTTGTCGCA
      2:    L  R  Y  F  A  E  G  N  L  R  K  G  V  S  Q  S  C  G  M  N  N  E  S  L  T  A  A  L  A  C  K  L  S  Q
      3:
```

*Fig. 1J*

```
       6301                                6361
   AGCTGACCTTGATTTTTGTCCAGCTTAACGAACTTCAAGTGCTTTGTATCTGCTTCAAACATGAAAAATGCCGCTGGCCAGTACATTGAAGCAGCTTAT
1:
2:  .. A  D  L  D  F  L  S  S  L  T  N  F  K  C  F  V  S  A  S  N  M  K  N  A  A  G  Q  Y  I  E  A  A  Y ..
3:

6401                                6461
   GCCAGGGCCCTACGCCAAGAGTTGGCCTCTCTAGTTCAGGTTGACAAGATGAAAGGAGTTTTGTCCAAGCTCGAGGCCTTTGCTGAAACAGCCACCCCGT
1:
2:  .. A  R  A  I  R  Q  E  L  A  S  L  V  Q  V  D  K  M  K  G  V  L  S  K  L  E  A  F  A  E  T  A  T  P ..
3:

6501                                6561
   CCCTTGACACAGGTGACGTGGTTGTTCTGCTTGGGCAACATCCTCACGGATCCATCCTCGATATTAATGTGGGAACTGAAAGGAAAACTGTGTCCGTGCA
1:
2:  .. S  L  D  T  G  D  V  V  V  L  L  G  Q  H  P  H  G  S  I  L  D  I  N  V  G  T  E  R  K  T  V  S  V  Q ..
3:

6601                                6661
   AGAGACCCGGAGCCTTGGCGGCTCCAAATTCAGTGTTTGCACTGTTGTGTCCAACACACCCGTGGATGCCTTAACCGGCATCCCACTCCAGACACCAACC
1:
2:  .. E  T  R  S  L  G  G  S  K  F  S  V  C  T  V  V  S  N  T  P  V  D  A  L  T  G  I  P  L  Q  T  P  T ..
3:

6701                                6761
   CCTCTTTTTGAGAATGGTCCGCGTCACCGCAGTGAGGAAGACCTCTTAAAGTCGAGAGAATCGAGAGAACACTGTGTGTCCCTCGGCTTTCACAACATCA
1:
2:  .. P  L  F  E  N  G  P  R  H  R  S  E  E  D  D  L  K  V  E  R  M  K  K  H  C  V  S  L  G  F  H  N  I ..
3:

6801                                6861
   ATGGCAAAGTATACTGCAAAATCTGGGATAAGTCTACCGGTGACACCTTTTACACCGGTGACGATGATTCCCGGTATACCCAAGACTATGCTTTTCAGGACAGTC
1:
2:  .. N  G  K  V  Y  C  K  I  W  D  K  S  T  G  D  T  F  Y  T  D  D  S  R  Y  T  Q  D  Y  A  F  Q  D  R  S ..
3:

6901                                6961
   AGCCGACTACAGAGACAGGACTATGAAGGTGTGCAAACCGCCCCCAACAGGGCTTTGATCCAAAGTCTGAAACCCCTGTTGGCACTGTAGTGATCGGC
1:
2:  .. A  D  Y  R  D  R  D  Y  E  G  V  Q  T  A  P  Q  Q  G  F  D  P  K  S  E  T  P  V  G  T  V  V  I  G ..
3:
```

Fig. 1K

```
      7001                     7021                     7041                     7061                     7081
1: GGTATTACGTATAATAGGTACCTGATCAAAGGTAAGGAGATCCTGGTTCCCAAGCCTGACAACTGCCTTGAAGCTGCCAAGCTGTCCCTTGAGCAAGCTC
    ...  G  I  T  Y  N  R  Y  L  I  K  G  K  E  I  L  V  P  K  P  D  N  C  L  E  A  A  K  L  S  L  E  Q  A
2: ...................................................................................................
3: ...................................................................................................

7101                     7121                     7141                     7161                     7181
1: TCGCTGGATGGTCAAACTTGTGACCTCACAGCTGCCGAGGTGGAAAAGCTAAAGCGTATCATTAGTCAACTCCAAGGTTTGACCACTGAACAGGCTTT
    L  A  G  M  G  Q  T  C  D  L  T  A  A  A  E  V  E  K  L  K  R  I  I  S  Q  L  Q  G  L  T  T  E  Q  A  L
2: ...................................................................................................
3: ...................................................................................................

7201  SEQ ID NO: 3       7221                     7241                     7261                     7281
1: AAACTGTTAGCCGCCAGTGGCTTGACCCGCTGTGGCGCCCGCGGGGCCGGGGGCTTAGTTGTAACTGAAACAGCTGTGAAAATTGTAAAATACCAGCAGAACTTTCA
       L  A  A  S  G  L  T  R  C  G  R  G  G  L  V  V  T  E  T  A  V  K  I  V  K  Y  H  S  R  T  F
2:    L  A  A  S  .............................................................................
3:    N  C  @  ................................................................................

7301                     7321                     7341                     7361                     7381
1: CCTTTGGCCCCTCTTGACCTGAAAGTTACTTCCGAGGCGGAGGTAAAGAAAATCAACTGAGCAGGGCCACGCTGTTGTGGCAAACTTATGTTCGGTGTCAT
    T  F  G  P  L  D  L  K  V  T  S  E  A  E  V  K  K  S  T  E  Q  G  H  A  V  V  A  N  L  C  S  G  V  I
2: ...................................................................................................
3: ...................................................................................................

7401                     7421                     7441                     7461                     7481
1: CTTGATGAGACCTCACCCACCGTCCCTTGTTGACGTTCTTCTGAAACCCGGACTTGACACAAAACCCGGCATTCAACCGGACTTGACACAAAACCCGGCATTCAACCAGGCATGGGCCATGGAAGGCATGTGAAGTTAGGCCGGGG
    L  M  R  P  H  P  P  S  L  V  D  V  L  L  K  P  G  L  D  T  K  P  G  I  Q  P  G  H  G  A  G  N  M
2: ...................................................................................................
3: ...................................................................................................

7501                     7521                     7541                     7561                     7581
1: GGCGTGGACGGTTCTATGTGGGATTTTGAAACCGCCACACCGGCAGAACTGAGTTATCCAAGCAAATAATTCAAGCTGAGATTTGAAGTTGAAGTTAGGCCGGGG
    G  V  D  G  S  M  W  D  F  E  T  A  P  T  K  A  E  L  E  L  S  K  Q  I  I  Q  A  C  E  V  R  R  G
2: ...................................................................................................
3: ...................................................................................................

7601                     7621                     7641                     7661                     7681
1: ACGCCCCCGAACCTCCAACTTCCTTATAAGCTCTATCCTTATAGCTCTATCCTTATCAATAAGCATGGGGGGATCCTGCGCGGGCCGCATGCGGCGCGCGCGGAGGGGATATCCTGCGCGGGCCTTATCAATACCAGGTTTGAGAGATTTATC
    D  A  P  N  L  Q  L  P  Y  K  L  Y  P  V  R  G  D  P  A  R  H  G  G  R  L  I  N  T  R  F  G  D  L  S
2: ...................................................................................................
3: ...................................................................................................
```

Fig. 1L

```
          7701                                                         7741                                                         7781
     TTACAAAACTCCTCAAGACACCAAGTCCGCAATCCACGCGGCTTGTTGCCTGCACCCCAAACGGGGCCCCTGTGTCTGATGGTAAATCAACACTAGTACC
1:    Y  K  T  P  Q  D  T  K  S  A  I  H  A  A  C  C  L  H  P  N  G  A  P  V  S  D  G  K  S  T  L  G  T
2: ........................................................................................................
3: ........................................................................................................

7801                                                         7841                                                         7881
     ACTCTCCAACATGGTTTCGAGCTTTATGTCCCCACTGTACCTTATAGTGTCATGGAGTACCTCGATTCACGCCCTGACACCCTTTTTATGTGTACTAAGC
1:    T  L  Q  H  G  F  E  L  Y  V  P  T  V  P  Y  S  V  M  E  Y  L  D  S  R  P  D  T  P  F  M  C  T  K
2: ........................................................................................................
3: ........................................................................................................

7901                                                         7941                                                         7981
     ATGGCACTTCCAAGGCTGCTGCAGAGGACCTCCAAAAATACGACCTGTCCACTCAGGATTCGTCCTGCCTGGGTCTTACGCCTAGTACGTAGATTCAT
1:    H  G  T  S  K  A  A  A  E  D  L  Q  K  Y  D  L  S  T  Q  G  F  V  L  P  G  V  L  R  L  V  R  R  F  I
2: ........................................................................................................
3: ........................................................................................................

8001                                                         8041                                                         8081
     CTTTGGCCATATTGGTAAGGCGCCGCCCATTGTTCCTTCCATCAACCTATCCGCCAAAAACTCTATGGCAGGATCAATGGCCAGAGGTTTCCAACAAAG
1:    F  G  H  I  G  K  A  P  P  L  F  L  P  S  T  Y  P  A  K  N  S  M  A  G  I  N  G  Q  R  F  P  T  K
2: ........................................................................................................
3: ........................................................................................................

8101                                                         8141                                                         8181
     GACGTTCAGAGCATACCTGAAATTGATGAAATGTGTGCCCGCGTTCAAGGAGAATTGGCCAAACTGTGACACCTTGTACTCTCAAGAAACAGTACTGTT
1:    D  V  Q  S  I  P  E  I  D  E  M  C  A  R  A  V  K  E  N  W  Q  T  V  T  P  C  T  L  K  K  Q  Y  C
2: ........................................................................................................
3: ........................................................................................................

8201                                                         8241                                                         8281
     CCAAGCCCAAAACCAGGACCATCCTGGGCACCAACAACTTTATTGCCTTGGCTCACAGATCGGCCGCTCAGTGGTGTCACCAGGCATTCATGAAGAAGC
1:    S  K  P  K  T  R  T  I  L  G  T  N  N  F  I  A  L  A  H  R  S  A  L  S  G  V  T  Q  A  F  M  K  K  A
2: ........................................................................................................
3: ........................................................................................................

8301                                                         8341                                                         8381
     CTGGAAGTCCCCAATTGCCTTGGGAAAAAACAAATTCAAGGAGCTGCATTGCACCGTGCGCGGCAGGTGTCTTGAGGCCGACTTGGCCTCCTGTGACCGC
1:    W  K  S  P  I  A  L  G  K  N  K  F  K  E  L  H  C  T  V  A  G  R  C  L  E  A  D  L  A  S  C  D  R
2: ........................................................................................................
3: ........................................................................................................
```

Fig. 1M

```
              8401                        8421                        8441                        8461                        8481
    AGCACCCCGCCATTGTAAGATGGTTCGTCGCCAACCTCCTGTATGAACTTGCAGGATGTGAAGAGTACTTGCCTAGCTATGTGCTTAATTGCTGCCATG
1:   S  T  P  A  I  V  R  W  F  V  A  N  L  L  Y  E  L  A  G  C  E  E  Y  L  P  S  Y  V  L  N  C  C  H
2:  ...............................................................................................
3:  ...............................................................................................

8501                        8521                        8541                        8561                        8581
    ACCTTGTGGCAACAGGATGTGCCTTCACAAACGCGGTGCCTTGTCGTCCGGGGACCCCGTCGTGTCCAACACGGTGTCCAACACGGTGTCCAACACGGTGAT
1:   D  L  V  A  T  Q  D  G  A  F  T  K  R  G  G  L  S  S  G  D  P  V  T  S  V  S  N  T  V  Y  S  L  V  I
2:  ...............................................................................................
3:  ...............................................................................................

8601                        8621                        8641                        8661                        8681
    TTATGCCCAGCACATGGTTGTGTCGGCCTTGAAAATGGGTCATGAAAATCGGTCTCAAGTTCCTGGAGGAACAGCTCAAATTTGAGGACCTCCTGAAATT
1:   Y  A  Q  H  M  V  L  S  A  L  K  M  G  H  E  I  G  L  K  F  L  E  E  Q  L  K  F  E  D  L  L  E  I
2:  ...............................................................................................
3:  ...............................................................................................

8701                        8721                        8741                        8761                        8781
    CAGCCTATGCTGGTATACTCTGATGACCTTGTCTTGTACGCTGAAAGACCCACTTTTCCTAATTACCACTGGTGGTCGAGCACCTTGACTAATGCTGG
1:   Q  P  M  L  V  Y  S  D  D  L  V  L  Y  A  E  R  P  T  F  P  N  Y  H  W  W  V  E  H  L  D  L  M  L
2:  ...............................................................................................
3:  ...............................................................................................

8801                        8821                        8841                        8861                        8881
    GTTTCAGAACGGACCCAAAGAAAACTGTCATAACTGATGATAAACCAGCTTCCTCGGCTGCAGAATTGAGGCCAGGCGACAGCTGGTTCCCAATCGGACCG
1:   G  F  R  T  D  P  P  K  K  T  V  I  T  D  K  P  S  F  L  G  C  R  I  E  A  G  R  Q  L  V  P  N  R  D  R
2:  ...............................................................................................
3:  ...............................................................................................

8901                        8921                        8941                        8961                        8981
    CATCCTGGCTGCTCTCGCATACCACACATGAAGGCCCAGAACGCCTCAGAGTATTATGCGTCTTACGCAGCAGCGATTCTGATGGATTCATGCGCTTGCATTGAC
1:   I  L  A  A  L  A  Y  H  M  K  A  Q  N  A  S  E  Y  Y  A  S  A  A  A  I  L  M  D  S  C  A  C  I  D
2:  ...............................................................................................
3:  ...............................................................................................

9001                        9021                        9041                        9061                        9081
    CATGACCCTGAGTGGTATGAGGACCTCATCTGCGGTATTGCCCAGTGCGCCAGGCAGGATGGTTATAGCTTCCCAGGTCCCGGGCCATTTTTCATGTCCATGT
1:   H  D  P  E  W  Y  E  D  L  I  C  G  I  A  Q  C  A  R  Q  D  G  Y  S  F  P  G  P  A  F  F  M  S  M
2:  ...............................................................................................
3:  ...............................................................................................
```

Fig. 1N

```
     9101                9121                9141                9161                9181
  GGGAGAGGCTGAGAAGTCATAATGAAGGGAAGAAATTTCGCCACTGTGATTGTGGGCATCTGCGATGCCAAAGCTGACTATGCATCCGCCTGTGGGCTTGATTTGTG
1: W  E  R  L  R  S  H  N  E  G  K  K  F  R  H  C  G  I  C  D  A  K  A  D  Y  A  S  A  C  G  L  D  L  C
2: ..................................................................................................
3: ..................................................................................................

9201                9221                9241                9261                9281
  TTTGTTTCATTCGCACTTTCATCAACACTGTCCTGTCACTCTGAGCTGCGGTCTCAAGGAATGTTCGCAGTGTCAGTCACCTGTTGGG
1: L  F  H  S  H  F  H  Q  H  C  P  V  T  L  S  C  G  H  H  A  G  S  R  E  C  S  Q  C  Q  S  P  V  G
2: ..................................................................................................
3: ..................................................................................................

9301                9321                9341                9361                9381
  GCTGGCAGATCCCCTCTTGATGCCGTGTTAAAACAAATTCCATATAAACCTCCGTACTGTCATCATGAAGGTGGGTAACAAAACAACGGCTCTCGATC
1: A  G  R  S  P  L  D  A  V  L  K  Q  I  P  Y  K  P  P  R  T  V  I  M  K  V  G  N  K  T  T  A  L  D
2: ..................................................................................................
3: ..................................................................................................

9401                9421                9441                9461                9481
  CGGGGAGGTACCAATCCCGTCTCGTTGCAGTCAAGAGGTATTGCAGGCAATGAGGTTGATCTTTCGATGGAGACTACCAAGTGGTGCCTCT
1: P  G  R  Y  Q  S  R  R  G  L  V  A  V  K  R  G  I  A  G  N  E  V  D  L  S  D  G  D  Y  Q  V  V  P  L
2: ..................................................................................................
3: ..................................................................................................

9501                9521                9541                9561                9581
  TTTGCCGACTTGCAAAGACACATAAACATGGTGAAGGTTGGCTTGTAATGTACTACTCAGTAAGTCATAGTGGGGCCACCAGGTTCCGGAAAGACCACCTGG
1: L  P  T  C  K  D  I  N  M  V  K  V  A  C  N  V  L  L  S  K  F  I  V  G  P  P  G  S  G  K  T  T  W
2: ..................................................................................................
3: ..................................................................................................

9601                9621                9641                9661                9681
  TTACTAGGTCAAGTCCAGGACGATGATGTCATTTACACACCCATCAGATACTATGTTGATATAGTCAGTGCTCTCAAAGTTTGCAGGTATATACCATCC
1: L  L  G  Q  V  Q  D  D  D  V  I  Y  T  P  T  H  Q  T  M  F  D  I  V  S  A  L  K  V  C  R  Y  T  I
2: ..................................................................................................
3: ..................................................................................................

9701                9721                9741                9761                9781
  CAGGAGCCTCAGGACTTCCTTTCCCACCACCCGCCGCCAGGTCCGGACGTTGGGTTAGGCTCATAGCCAGCGGGGCACGTCCCTGGCCAGTATCATACCTCGA
1: P  G  A  S  G  L  P  F  P  P  P  A  R  S  G  P  W  V  R  L  I  A  S  G  H  V  P  G  R  V  S  Y  L  D
2: ..................................................................................................
3: ..................................................................................................
```

Fig. 10

```
         9801                        9821                        9841                        9861                        9881
     TGAGGCTGGATACTGTAATCATTTGGACATTCTCAGACTGCTCTCCAAAACACCCCTGTGTGTTTGGGTGACCTTCAACAACTTCACCCTGTCGGCTTT
      E  A  G  Y  C  N  H  L  D  I  L  R  L  L  S  K  T  P  L  V  C  L  G  D  L  Q  Q  L  H  P  V  G  F
1:   ..................................................................................................
2:   ..................................................................................................
3:   ..................................................................................................

9901                        9921                        9941                        9961                        9981
     GATTCCTACTGTTATGTGTTGATCAGATGCCTCAGAAGCAACTGACCACCATTTACAGATTTGGCCCTAACATCTGCGCGGCCATTCAGCCTTGCTACA
      D  S  Y  C  Y  V  F  D  Q  M  P  Q  K  Q  L  T  T  I  Y  R  F  G  P  N  I  C  A  A  I  Q  P  C  Y
1:   ..................................................................................................
2:   ..................................................................................................
3:   ..................................................................................................

10001                       10021                       10041                       10061                       10081
     GGGAGAAGCTTGAATCTAAGGCTAGGAACACCAGGGTGGTTTTTACCACCCGGCCTGTGGCCTTTGGTCAGGTGCTGACACCATACCATAAAGATGCAT
      R  E  K  L  E  S  K  A  R  N  T  R  V  V  F  T  T  R  P  V  A  F  G  Q  V  L  T  P  Y  H  K  D  R  I
1:   ..................................................................................................
2:   ..................................................................................................
3:   ..................................................................................................

10101                       10121                       10141                       10161                       10181
     CGGCTCTGCGATAACCATAGACTCATCCCAGGGGGCCACCTTTGATATTGTGACATTGCTCCACCTGCCAAAATCTCTAAACAAATCCCGAGCACTT
      G  S  A  I  T  I  D  S  S  Q  G  A  T  F  D  I  V  T  L  H  L  P  S  P  K  S  L  N  K  S  R  A  L
1:   ..................................................................................................
2:   ..................................................................................................
3:   ..................................................................................................

10201                       10221                       10241                       10261                       10281
     GTGGCCATCACTCGGGCAAGACGGGTTGTTCATTTATGACCCTCCATAATCAGCTTCAGGAGTTTTTCAACTTAACCCCCTGAGCGTACTGATTGCAACC
      V  A  I  T  R  A  R  H  G  L  F  I  Y  D  P  H  N  Q  L  Q  E  F  F  N  L  T  P  E  R  T  D  C  N
1:   ..................................................................................................
2:   ..................................................................................................
3:   ..................................................................................................

10301                       10321                       10341                       10361                       10381
     TTGTGTTCAGCCGTGGGGATGAGCTAGTAGTTCTGGATGCGGATAATGCAGTCACAACTGTGGCGAAGGCCCTAGAAACAGGTCCATCTCGATTCGAGT
      L  V  F  S  R  G  D  E  L  V  V  L  D  A  D  N  A  V  T  T  V  A  K  A  L  E  T  G  P  S  R  F  R  V
1:   ..................................................................................................
2:   ..................................................................................................
3:   ..................................................................................................

10401                       10421                       10441                       10461                       10481
     GTCAGACCCGAGGTGCAAGTCTCTCTTAGCCGGCTTGTTCGGCCAGTCGTATGCCACTACCGCAAGTGGCACATAACTTGGGGTTTTAC
      S  D  P  R  C  K  S  L  L  A  A  C  S  A  S  L  E  G  S  C  M  P  L  P  Q  V  A  H  N  L  G  F  Y
1:   ..................................................................................................
2:   ..................................................................................................
3:   ..................................................................................................
```

Fig. 1P

```
       10501                                     10561
      TTTTCCCCGGACAGTCCAGCATTTGCACCTCTGCCAAGAGAGTTGGGCGCCACATTGGCCAGTAGTTACCCACCAGAATAATCGGGCGTGGCCTGATCGAC
1:     F  S  P  D  D  S  P  A  F  A  P  L  P  R  E  L  A  P  H  W  P  V  V  T  H  Q  N  N  R  A  W  P  D  R
2:    ..............................................................................................
3:    ..............................................................................................

10601                                     10661
      TTGTCGCTAGTATGCGCCAATTGATGCCGCTACAGCAAGCCTTTGCAGGTATGGTGGTGCAGGTATGTCGGCGCCGTCCACCTTTCTTGGTACTCCTGGTGT
1:     L  V  A  S  M  R  P  I  D  A  R  Y  S  K  P  M  V  G  A  G  Y  V  V  G  P  S  T  F  L  G  T  P  G  V
2:    ..............................................................................................
3:    ..............................................................................................

10701                                     10761
      GGTGTCATATATTATCTCACGCTGTACATCAGGGGTGAGCCCCAGGCTTTGCCAGAAAACACTCGTTTCAACAGGACGTATAGCTACAGATTGTCGGAGTAT
1:     V  S  Y  Y  L  T  L  Y  I  R  G  E  P  Q  A  L  P  E  T  L  V  S  T  G  R  I  A  T  D  C  R  E  Y
2:    ..............................................................................................
3:    ..............................................................................................

10801                                     10861
      CTCGACGCGGCTGAGGAAGAGGCAGCAAAAGAACTCCCCCACGCCATTTATTGGCGATGTCAAAGGTACCACGGTTGTCATCACATCACATCAA
1:     L  D  A  A  E  E  E  A  A  K  E  L  P  H  A  F  I  G  D  V  K  G  T  T  V  G  G  C  H  H  I  T  S
2:    ..............................................................................................
3:    ..............................................................................................

10901                                     10961
      AGTACCTACCTAGGTCCCCTGCCTAAGGACTCTATTGCCGTAGTTGGAGTAAGTTCGCCCGGCAGGGCTGCTAAAGCAATGTGCACTCTCACCGATGTGTA
1:     K  Y  L  P  R  S  L  P  K  D  S  I  A  V  V  G  V  S  S  P  G  R  A  A  K  A  M  C  T  L  T  D  V  Y
2:    ..............................................................................................
3:    ..............................................................................................

11001                                     11061
      TCTCCCCGAACTCCGGCCTATCTGCAACCTGGAGACGGCATCAAAATGCTGGAAACTCAAATTAGACTTCAGGAGAGTCCGACTAATGGTCTGGAAAGGA
1:     L  P  E  L  R  P  Y  L  Q  P  E  T  A  S  K  C  W  K  L  K  L  D  F  R  D  V  R  L  M  V  W  K  G
2:    ..............................................................................................
3:    ..............................................................................................

11101                                     11161
      GCCACCGCCTATTCCAGTTGGAAGGGTTTACATGGTCGGCGCTCCAGTTTATTCAGCTGCCCAAGGATGCCGTTGTATACATTGATC
1:     A  T  A  Y  F  Q  L  E  G  F  T  W  S  A  L  P  D  Y  A  R  F  I  Q  L  P  K  D  A  V  V  Y  I  D
2:    ..............................................................................................
3:    ..............................................................................................
```

Fig. 12

```
      11201                            11241                            11281
     CGTGTATAGGACCGGCACAGCCAAGTCGTGCGAACCACAGACTGGCGGCCGACCTGGCAGTGACACCGTATGATTACGGTGCCCAGAACAT
1:    P  C  I  G  P  A  T  A  N  R  K  V  V  R  T  T  D  W  R  A  D  L  A  V  T  P  Y  D  Y  G  A  Q  N  I
2:    .  .  .  .  .  .  .  .  .  .  .  .  .  .  .  .  .  .  .  .  .  .  .  .  .  .  .  .  .  .  .  .  .  .
3:    .  .  .  .  .  .  .  .  .  .  .  .  .  .  .  .  .  .  .  .  .  .  .  .  .  .  .  .  .  .  .  .  .  .

11301                            11341                            11381
     TTTGACAACAGCCTGGTTCGAGGACCTCGGGCCCAGTGGCCCCAGTGGAAGATTTTAGGGTTGCAGCCCTTTAGGCGAGCGTTTGGCCTTGAAAACACTGAGGATTGG
1:    L  T  T  A  W  F  E  D  L  G  P  Q  W  K  I  L  G  L  Q  P  F  R  R  A  F  G  L  E  N  T  E  D  W
2:    .  .  .  .  .  .  .  .  .  .  .  .  .  .  .  .  .  .  .  .  .  .  .  .  .  .  .  .  .  .  .  .  .
3:    .  .  .  .  .  .  .  .  .  .  .  .  .  .  .  .  .  .  .  .  .  .  .  .  .  .  .  .  .  .  .  .  .

11401                            11441                            11481
     GCAATCCTTGCACGTGTCGTATGAATGACGGCAAGGACTATACACTGACTATAAACTGGAACTGTGTTCGAGAACGCTCACACGACGTGCTCGTG
1:    A  I  L  A  R  R  M  N  D  G  K  D  Y  T  D  Y  N  W  N  C  V  R  E  R  S  H  A  I  Y  G  R  A  R
2:    .  .  .  .  .  .  .  .  .  .  .  .  .  .  .  .  .  .  .  .  .  .  .  .  .  .  .  .  .  .  .  .  .
3:    .  .  .  .  .  .  .  .  .  .  .  .  .  .  .  .  .  .  .  .  .  .  .  .  .  .  .  .  .  .  .  .  .

11501                            11541                            11581
     ACCATACATATCATTTGCCCCCGGCACGGAACTGCAGGTGGAGCTAGGTAAACCCGGCTGCCGCCTGGGCAGGTGCCTGAATTGGAGTAATGCAAT
1:    D  H  T  Y  H  F  A  P  G  T  E  L  Q  V  E  L  G  K  P  R  L  P  P  G  Q  V  P  @     .  M  Q
2:    .  .  .  .  .  .  .  .  .  .  .  .  .  .  .  .  .  .  .  .  .  .  .  .  .  .  .  .  .     SEQ ID NO: 4
3:    .  .  .  .  .  .  .  .  .  .  .  .  .  .  .  .  .  .  .  .  .  .  .  .  .  .  .  .  .

11601                            11641                            11681
     GGGGTCACTGTGGAGTAAGATCAGCAGCCAGCTGTTCGTGGACGCCCTTCACTGAGTTCCTTGTTGATATTGTCATTTTCTTGCCATACTGTTT
1:    W  G  H  C  G  V  R  S  A  S  C  S  W  T  P  S  L  S  S  L  L  V  W  L  I  L  S  F  F  L  P  Y  C  L
2:    .  .  .  .  .  .  .  .  .  .  .  .  .  .  .  .  .  .  .  .  .  .  .  .  .  .  .  .  .  .  .  .  .  .
3:    .  .  .  .  .  .  .  .  .  .  .  .  .  .  .  .  .  .  .  .  .  .  .  .  .  .  .  .  .  .  .  .  .  .

11701                            11741                            11781
     GGGGTTCACCGTCGCAGGATGGTTATTGGTCTTCTTTCTCAGAGTGGTTTGCTCCGGCTTCTCCGTTGCCGCTCTCCTGCCATTCACTCCCCGAACTATCGA
1:    G  S  P  S  Q  D  G  Y  W  S  F  F  S  E  W  F  A  P  R  E  S  V  R  A  L  P  F  T  L  P  N  Y  R
2:    .  .  .  .  .  .  .  .  .  .  .  .  .  .  .  .  .  .  .  .  .  .  .  .  .  .  .  .  .  .  .  .  .
3:    .  .  .  .  .  .  .  .  .  .  .  .  .  .  .  .  .  .  .  .  .  .  .  .  .  .  .  .  .  .  .  .  .

11801                            11841                            11881
     AGGTCCCTATGAAGGCTTGTTGCCCAACTGGACCGGACGTCCCACAATTTGCAGTTAAGCACCCACTGGTATGTTTGGCACACATGGGTATGTTTTGGCACATGGGAGTTTCCCACT
1:    R  S  Y  E  G  L  L  P  N  C  R  P  D  V  P  Q  F  A  V  K  H  P  L  G  M  F  W  H  M  R  V  S  H
2:    .  .  .  .  .  .  .  .  .  .  .  .  .  .  .  .  .  .  .  .  .  .  .  .  .  .  .  .  .  .  .  .  .
3:    .  .  .  .  .  .  .  .  .  .  .  .  .  .  .  .  .  .  .  .  .  .  .  .  .  .  .  .  .  .  .  .  .
```

Fig. 1R

```
      11901                            11921                            11941                            11961                            11981
1: TGATTGATGAGATGGTCTCTCGCCCCATTTACCCAGAGACCATGGAACATTCAGGAGACAAGCGGCATGGAAGCATGTGTTGGTGAGGCCACTCTCACGAAGCT
2: ...  L   I   D   E   M   V   S   R   R   I   Y   Q   T   M   E   H   S   G   Q   A   A   W   K   H   V   V   G   E   A   T   L   T   K   L
3: ...........................................................................................................................................

12001                            12021                            12041                            12061                            12081
1: TTCAGGGCTCGACATAGTTACCCATTTCCAACACCTGGCCGCAGTGGAGGCGGATTCTTGTCGCTTTCTCAGCTCACGACTCGTGATGCTAAAGAATCTT
2: ...  S   G   L   D   I   V   T   H   F   Q   H   L   A   A   V   E   A   D   S   C   R   F   L   S   S   R   L   V   M   L   K   N   L
3: ...........................................................................................................................................

12101                            12121                            12141                            12161                            12181
1: GCCGTTGGCAATGTGAGCCTGCAGTACAACACCACGCTTGAGCTCATTTTCCCCAGGCACGAGGCCCAAGTTGACCGACTTCAGAC
2: ...  A   V   G   N   V   S   L   Q   Y   N   T   T   L   N   R   V   E   L   I   F   P   T   P   G   T   R   P   K   L   T   D   F   R
3: ...........................................................................................................................................

12201    SEQ ID NO: 5            12221                            12241                            12261                            12281
1: AATGGCTCATCAGTGTGCACGCTTCCATTTTTTCCTCTGTGGCTTCATCTGTTACTTTGTTCACAGTGCTTTGGCTTGCGTTGGCTTTTGGCTTTGTACTTTGTTCAGTTCGAATTCCAGCTCTACGCTATGT
2: ...  M   A   H   Q   C   A   R   F   H   F   F   L   C   G   F   I   C   Y   T   L   F   T   V   H   S   A   L   A   S   N   S   S   T   L   C
3: ...  Q   W   L   I   S   V   H   A   S   I   F   F   S   V   A   S   S   V   T   L   F   T   V   L   W   L   R   I   P   A   L   R   Y   V 12301                            12321                            12341                            12361                            12381
1: TTTTGGTTTCCATTGGCCCACGGCCAACACATCATTCGAGCTGACCATCAACTACACCGTATGCATGCCCTGTCCTACCAGTCAAGCAGCTCTCCAAAGC
2: ...  F   W   F   P   L   A   H   G   N   T   H   S   F   E   L   T   I   N   Y   T   V   C   M   P   C   P   T   S   Q   A   A   L   Q   R
3: ...  F   G   F   H   W   P   T   A   T   H   H   S   S   @

12401                            12421                            12441                            12461                            12481
1: TCGAGCCCGGTCGTAACATGTGGTGCAAAATAGGGCATGACAGATGAGTTGTTAAATGTCCATCCCGTCCGGGTACGACAA
2: ...  L   E   P   G   R   N   M   W   C   K   I   G   H   D   R   C   E   E   R   D   Q   D   E   L   L   M   S   I   P   S   G   Y   D   N 12501                            12521                            12541                            12561                            12581
1: CCTCAAACTTGAGGGTTATTATGCTTGGCTGGCTTTTTTGTCTTTTTTCCTACGCGGCCCAATTCCATCCAGAGTTGTTCGGATCGGAAATGTGTCGGC
2: ...  L   K   L   E   G   Y   Y   A   W   L   A   F   L   S   F   S   Y   A   A   Q   F   H   P   E   L   F   G   I   G   N   V   S   R
```

```
        14001                    14021                    14041                    14061
1: ACTCCTGGGGCTATTGCACATCCTAATATTTCTGAACTGTTCCTTCACATTCGGATACATATGTGCATTTCAATCCGCCAACCGTGTCGCACTT
2:  L  L  G  L  I  H  I  L  I  F  L  N  C  S  F  T  F  G  Y  M  T  Y  V  H  F  Q  S  A  N  R  V  A  L
3:

14101                    14121                    14141                    14161
1: ACCCTGGGGGCTGTGTCGCCCTTCTGTGGGGCGTTTACAGCCTCACAGAGTCATGGAAGTTTATCACTTCCAGATGCAGATTGTGTTGCCTTGGCCGGC
2:  T  L  G  A  V  V  A  L  L  W  G  V  Y  S  L  T  E  S  W  K  F  I  T  S  R  C  R  L  C  C  L  G  R
3:

14201                    14221                    14241                    14261
1: GATACATTCTGGCCCCTGCCCATCACGTAGAAAGTGCTGCAGGTCTCCATTCAATCTCAGCGTCTGGTAACCGAGCATACGCTGTGAGAAAGCCCGGATT
2:  R  Y  I  L  A  P  A  H  H  V  E  S  A  A  G  L  H  S  I  S  A  S  G  N  R  A  Y  A  V  R  K  P  G  L
3:

14301                    14321                    14341                    14361
1: AACATCAGTGAACGGCACTCTAGTACCAGGACTTCGGGAGCCTGTCGTGGGGCGCAAACGAGCTGTGTTAAACGAGGAGTGGTTAACCTCGTCAAATATGGC
2:  T  S  V  N  G  T  L  V  P  G  L  R  S  L  V  L  G  G  K  R  A  V  K  R  G  V  N  L  V  K  Y  G
3:                                                                                              M  A  →SEQ ID NO: 10

14401                    14421                    14441                    14461
1: CGGTAAAAACCAGAGCCAGAGAAAAAGAAAAGTACAGCTCAATGGGAATGCCAGCCAGTCAATCAACTGTGCCAGTTGCTGGGTGCAATGATAAAG
2:  R  @  K  N  Q  S  Q  K  K  K  K  S  T  A  P  M  G  N  G  Q  P  V  N  Q  L  C  Q  L  L  G  A  M  I  K
3:

14501                    14521                    14541                    14561
1: TCCCAGCGCCCAGCCTAGAGGAGACAGGCCAAAAAGAAAAAGCCTGAGAAGATGACATCCGGCATCACCTTA
2:  S  Q  R  Q  Q  P  R  G  G  Q  A  K  K  K  K  P  E  K  P  H  F  P  L  A  A  E  D  D  I  R  H  H  L
3:

14601                    14621                    14641                    14661                    14681
1: CCCAGACTGAACGTTCTCTGCTTGCAATCGATCCAGACGGCTTTCAATCAAGGCGCGGAACTGCGTGCTTTCATCCAGCGGAAGTTCAGTTTTCA
2:  T  Q  T  E  R  S  L  C  L  Q  S  I  Q  T  A  F  N  Q  G  A  G  T  A  S  L  S  S  G  K  V  S  F  Q
3:
```

```
           14701                  14721                  14741                  14761                  14781
     GGTTGAGTTCATGCTGCCGGTTGGTCATACAGTGCGCCCTGATTCGCGTGACTTCTACATCCGCCAGTCAGGGTGCAAGTTAATTTGACAGTCAGGTGAAT
1: ..V  E  F  M  L  P  V  G  H  T  V  R  L  I  R  V  T  S  T  S  A  S  Q  G  A  S  @ .................
2: ....................................................................................................
3: ....................................................................................................

14801                  14821                  14841                  14861                  14881
     GGTCGCGATTGGCGTGTGACCTCTGAGTCACCTATTCAATTAGGGCGATCACATGGGGTCATACTTAATCAGGCAGGAACCATGTGACCGAAATT
1: ....................................................................................................
2: ....................................................................................................
3: ....................................................................................................
```

SEQ ID NO: 11
Nucleotides 1,830 to 2,618 of SEQ ID NO: 1

: TCTCTAGTTTGTATAACTTGCTATTAGAGGTTGTTCCGCAAAAATGCGGTGTCACGGAAG
: ---------------A--A-----------------------------C--------

: GGGCCTTCACCTATGCTGTTGAGAGGATGTTAATGGATTGTCCGAGCTCCGAACAGGCCA
: ----T----T------------------G-A----------------A---------

: TGGCTCTTCTGGCAAAAATTAAAGTTCCATCCTCAAAGGCCCCATCTGTGTCCTTGGACG
: ----C---------------------------------------G---------C------

: AGTGTTTCCCTGCAGATGTTCCGGCCGATTTCGAGCCAACGTCTCAGAAAAGGCCCCAAA
: ----------A-G------TTA-----C---------G-A------G-----------

: GTTCCGGCGCCGCTGTCGCCCTGTGTTCATCGGATGCAGAAGGGTTCGAGGAAGCAGCCC
: ----------T-----T-T----------C--------A---A-----------------

: CAGAAGGAGTTCAAGAGAGAGGCCATAAGGCCGTCCACTCTGCACTCTTTGCCAAGGGTC
: -G----A------------T-----C----------------------C-----G------

: CAAATAACGAACAGGTACAGGTGGTTGCCGGTGAGCAACAGAAGCTCGGCGGTTGTGGTT
: -T--C--T--G-----------------------------T------------------

: TGGCAATCGGGAATGCTCA.........................................
: -----G--------------tgaaggtgctctggtctcagctggtctaattaacctggtag : ...........GTCCCCTTTAAATTCCATGAAAGAAAACATGCGCAGTAGCCGGGAAGACG
: gcgggaattt------C-C-G-CC------------------T--A------------

: AACCACTGGATTTGTCCCAACCAGCACCAGTTGCCGCAACGACCCTTGAGAGAGAGCAAA
: --------------------------------C-T--A------------T----------

: CACCCGATAACCCAGGTTCTGATGCCGGTGCCCTCCCCGCCACCGTTCGAGAATCTGTCC
: -------C--------------------------------T--------------T-----

: CGACAGGGCCTATGCTCCGTCATGTTGAGCACTGTGGCACGGAGTCTGGCGATAGCAGTT
: ----G--------A---T----------------C----------G-----C-------

: CGCCTTTGGATCTGTCTTATGCGCAAACTTTGGACCAGCCTTTAGATCTATCCCTGGCCG
: -------------A---G---------CC--------------A--------------

: TTTGGCCGGTGAAGGCCACCGCGTCTGACCCTGGCTGGGTCCACGGTAGGCGCGAGCCTG
: C------A----G--------------------------------------------

SEQUENCE LISTING

<160> NUMBER OF SEQ ID NOS: 21

<210> SEQ ID NO 1
<211> LENGTH: 14896
<212> TYPE: DNA
<213> ORGANISM: Porcine reproductive and respiratory syndrome virus

<400> SEQUENCE: 1
cttgttgtgg ggaggaactc ccgaggattt tcggagagga cctgctttac tggatgttca      60
ccctttaacc atgtgtggga gcgtctcccg gtgcatgtgc accccggctg tccgggtatt     120
ttggaacgcc ggccaagtct tttgcacacg gtgtgtcagt gcgcgggctc ttctctctcc     180
agagcttcag gacactgacc tcggtgcggt tggattgttt tacaggccta gggataagct     240
acactggaaa gtccctatcg gcatccccca ggcggaatgt actccatccg ggtgctgttg     300
gctctcagct gtattccctt tggcgcgcat gacctctggc aatcacaact tccttcaacg     360
acttgttaag gttgctgatg ttttgtaccg tgacggttgc ctggcacctc gacacctccg     420
tgagcttcaa gtttacgagc gcggctgcaa ctggtaccca atcacggggc ccgtacccgg     480
gatgggtttg tttgcgaatt ccatgcacgt atccgaccag ccgttccctg gtgccaccca     540
tgtgttgact aactcgcctc tacctcaaca ggcgtgtcgg caaccgttct gtccatttga     600
ggaagctcat tctggcgtgt ataggtggaa gaaatttgta attttttcgg actccccctc     660
caacggccaa tctcgcatta tgtggacgcc gaaatccgat gattcagctg ctctggagga     720
actaccgcct gagttagaac gtcaggttga aattctcatt cggagtttcc ctgctcatca     780
ccctgtcaac ctggcggact gggagctcac tgggtctcct gagaacggtt tttccttcaa     840

```
cacgtctcat tcttgcggtc atctcgtccg aaactccaac gtgtttgatg gcaagtgctg    900
gctcacctgc ttttggggcc agtcggtcga agtgcgctgc catgaagaac atctagccaa    960
cgccttcggt taccaaacca agtggggcgt gcacggtaag taccttcaac gcaggcttca   1020
agttcgcggc attcgtgctg tagtcgatcc tgacggcccc attcacgttg aagcgctgtc   1080
ttgctcccag tcttggatca ggcacctgac cctgaatgac gatgtcaccc caggatttgt   1140
tcgcctgaca tccattcgca ttgtgccgaa tacagagcct accacttccc agatctttcg   1200
atttggagcg cataagtggt atggcgctgc cggtaaacgg gctcgtgcca agcgtaccgc   1260
taaaggtggg aaggattctg ttcccgctct caaggttgcc ctgccggtcc ccgcctgtgg   1320
aataaccacc tattccccac cgacagacgg gtcttgtggt tggcatgtcc ttgccgccat   1380
aatgaaccgg atgatgaacg atgacttcac gtcccctctg actcagtaca acagaccaga   1440
ggatgattgg gcttcagatt atgatcttgc tcaggcgatt caatgtctac aactacctgc   1500
taccgtggtt cggaatcgcg cttgtcctaa cgccaagtac cttataaaac ttaacggggt   1560
tcactgggag gtagaggtga gatctggaat ggctcctcgc tccctttctc gtgaatgtgt   1620
ggtcggcgtt tgttctgaag gctgcgtcgc gccgccttac ccagcggatg ggcttcctaa   1680
gcgtgcactc gaggccttgg cgtctgctta cagactaccc tccgattgtg tttgctctgg   1740
tattgctgac tttcttgcca atccacctcc tcaagaattc tggactctcg acaaaatgtt   1800
gacctccccg tcaccagaac ggtccggctt ctctagtttg tataacttgc tattagaggt   1860
tgttccgcaa aaatgcggtg tcacggaagg ggccttcacc tatgctgttg agaggatgtt   1920
aatggattgt ccgagctccg aacaggccat ggctcttctg gcaaaaatta agttccatc    1980 ctcaaaggcc ccatctgtgt ccttggacga gtgtttccct gcagatgttc cggccgattt   2040
cgagccaacg tctcagaaaa ggccccaaag ttccggcgcc gctgtcgccc tgtgttcatc   2100
ggatgcagaa gggttcgagg aagcagcccc agaaggagtt caagagagag gccataaggc   2160
cgtccactct gcactctttg ccaagggtcc aaataacgaa caggtacagg tggttgccgg   2220
tgagcaacag aagctcggcg gttgtggttt ggcaatcggg aatgctcagt ccccttaaa    2280 ttccatgaaa gaaaacatgc gcagtagccg ggaagacgaa ccactggatt tgtcccaacc   2340
agcaccagtt gccgcaacga cccttgagag agagcaaaca cccgataacc caggttctga   2400
tgccggtgcc ctccccgcca ccgttcgaga atctgtcccg acagggccta tgctccgtca   2460
tgttgagcac tgtggcacgg agtctggcga tagcagttcg cctttggatc tgtcttatgc   2520
gcaaactttg gaccagcctt tagatctatc cctggccgtt tggccggtga aggccaccgc   2580
gtctgaccct ggctgggtcc acggtaggcg cgagcctgtc tttgtaaagc ctcgaaaagc   2640
tttctctgat agcgactcag cctttcagtt cgggaagctt tctgagtccg gctctgtcat   2700
tgagtttgac cgaacaaaag atgctccggt ggttgacgcc cctgttggct cgacgacttc   2760
gaacgaggca ctgtctatag ccgatccttt cgaatttgcc gaactcaagc gcccgcgttt   2820
ctccgcacaa gccttaattg accgaggcgg tccgcttgcc gatgtccatg cgaaaataaa   2880 gaacgggtg tatgaacggt gcctccaagc ttgtgagccc ggtagtcgtg caaccccagc    2940
caccaaggag tggctcgaca agatgtggga tagggtggac atgaaaactt ggtgctgcac   3000
ctcgcagttc caagctggtc gcattcttgc gtccctcaaa ttcctccctg acatgattca   3060
agacacaccg cctcctgttc ccaggaagaa ccgagctagt gacaatgccg atctgaagca   3120
actggtggca cagtgggata ggaaattgag tatgaccccct ccccaaaaac cggttgagcc   3180
agtgcttgac cagaccgtct ctccgcctac ggatactcag caagaagatg tgaccccctc   3240
```

-continued

```
cgatgggcca ccccatgcgc cggattttcc cagtcgtgtg agcacgggcg ggagttggaa      3300
agaccttatg tgttccggca cccgtctcgc ggggtctatc agtcagcgcc tcatgacatg      3360 ggttttttgaa gttttctccc acctcccagc ctttatgctc acactttttct cgccgcgggg    3420 ctctatggct ccaggtgatt ggttgtttgc aggtgttgtt ttacttgctc tcttgctctg      3480
tcattcttac ccgatactcg ggtgccttcc cttattgggt gtcttttctg gttctttgcg      3540
gcgtgttcgt ctgggtgttt ttggttcttg gatggctttt gctgtatttt tattctcgac      3600
tccatccaac ccagtcggtt cttcttgtga ccacgattcg ccggaatgtc atgctgagct      3660
tttggctctt gagcagcgcc aactttggga acctgtgcgc ggccttgtgg tcggcccctc      3720
gggcctctta tgtgtcattc ttggcaagtt actcggtggg tcacgttatc ctggcatat      3780 tctcctacgt ttatgcatgc ttacagattt ggcccttttct cttgtttatg tggtgtccca    3840
agggcgttgt cacaagtgtt ggggaaagtg tataagaaca gctcctactg aggtggctct      3900
taatgtgttt cctttcacgc gcgccacccg ttcctctctt gtatccttgt gtgatcgatt      3960
ccaaacgcca aaaggggttg atcctgtgca cttggcaacg ggttggcgcg ggtgctggcg      4020
tggtgggagt cccgtccatc aaccacacca aaagcccatt gcttatgcca acttggatga      4080
aaagaaaata tctgcccaaa cggtggttgc cgtcccatac gatcccagtc aggccatcaa      4140
atgcctgaaa gttctgcagg cgggagggc tatcgtggac cagcctacac ctgaggttgt        4200
tcgtgtgtcc gaaatcccct ctctcagctcc attttttcca aaagttccag tcaacccaga     4260
ttgcagagtc gtggtagatt cggacacttt tgtggctgcg gttcgatgcg gttactcgac      4320
agcacaactg gtcttgggcc agggcaactt tgccaagttg aatcagaccc ccccagagaa      4380
ctccacttcc accaaaacga ctggtggggc ctcttacacc cttgctgtgg ctcaagtaac      4440
tgtgtggact ctttttcatt tcatcctcgg cctttggttt acatcacctc aagtgtgtgg      4500
ccgaggaacc gctgacccat ggtgttcaaa tccttttttca tccccacct atggccctgg     4560 agttgtgtgc tcctctcggc tttgcgtgtc tgccgacggg gtcaccttgc cattgttctc      4620
agccgtggca caactttccg gtagagaggt ggggatcttt attttggtgc tcgtttcctt      4680
gattgccttg gccaccgta tggctcttaa ggcagacatg ttagtcgtct ttttggcttt       4740
ttgtgcttac gcctggccta tgagctcctg gttaatttgc ttctttccct tactcttgaa      4800
gtgggtcacc cttcaccctc tcaccatgct ttgggtgcac tcattcttgg tgttttgtct     4860
gccagcggcc ggcatcctct cattagggac aactggcctt ctctgggcaa ttggccgctt     4920
tacccaggtt gccggaatta ttacacctta tgacatccac caatacacct ctgggccacg      4980
tggtgcagct gctgtggcca cagccccaga aggcacttat atggccgcg tccggagagc      5040 tgctttaact gggcgaactt taatcttcac cccgtctgca gttggatccc ttctcgaagg      5100
tgccttcagg actcaaaaac cctgccttaa caccgtgaat gttgtaggct cttcccttgg     5160
ttccggaggg gttttcacca ttaacggcag aaggactgtc gtcactgctg ctcatgtgtt      5220
gaacggtgac acagctagag tcaccggcga ctcctacaac cgcatgcaca ctttcaagac     5280
caatggtgat tatgcctggt cccatgctga tgactggcag ggcgttgctc ctgtggtcaa      5340
ggttgcgaag gggtaccgcg tcgtgccta ctggcaaaca tcaactggtg tcgaacccgg      5400
cattattggg gaagggttcg ccttctgttt caccaactgt ggcgattcag ggtcacctgt      5460
tatctcagaa tctggtgatc tcattggaat ccacactggt tcaaacaaac tcggttctgg      5520
tcttgtgacg accccctgaag gggagacctg cgccatcaaa gaaaccaagc tctctgacct      5580
```

-continued

```
ttccagacat tttgcaggcc cgagcgttcc tcttggggac attaagttga gtccggccat    5640
catccctgat gtgacatcca ttccgagtga cttggcatcg ctcctagcct ccgtccctgt    5700
attggaaggc ggcctctcga ccgtccaact tctgtgtgtc tttttcctcc tctggcgcat    5760
gatgggccat gcctggacac ccattgtcgc cgtgggcttc tttctactaa atgaaatcct    5820
tccagcagtt ttggtccgag ccgtgttttc ttttgcactc tttgtgcttg catgggtcac    5880
cccctggtct gcgcaggtgt tgatgattag gctcctcacg gcatctctca accgcaacaa    5940
gttctctctg gcgttctacg cactcggggg tgtcatcggt ttggccgctg aaattgggac    6000
ttttgctggt agactgcctg aattgtctca agcccttttcg acatactgtt tcttacctag    6060
ggttcttgcc atggccagtt gtgttcccat catcatcatt ggtggactcc ataccctcgg    6120
tgtgattctg tggttgttca ataccggtg cctccacaac atgctggttg gtgatgggag    6180
tttttcaagc gccttcttcc tacggtattt tgcagagggt aatttgagaa aaggtgtttc    6240
acagtcctgt ggcatgaata acgagtccct gacggctgct ctagcttgca agttgtcgca    6300
agctgacctt gattttttgt ccagcttaac gaacttcaag tgctttgtat ctgcttcaaa    6360
catgaaaaat gccgctggcc agtacattga agcagcttat gccagggccc tacgccaaga    6420
gttggcctct ctagttcagg ttgacaagat gaaaggagtt ttgtccaagc tcgaggcctt    6480
tgctgaaaca gccaccccgt cccttgacac aggtgacgtg gttgttctgc ttgggcaaca    6540
tcctcacgga tccatcctcg atattaatgt ggggactgaa aggaaaactg tgtccgtgca    6600
agagacccgg agccttggcg gctccaaatt cagtgtttgc actgttgtgt ccaacacacc    6660
cgtggatgcc ttaaccggca tcccactcca gacaccaacc cctcttttg agaatggtcc    6720
gcgtcatcgc agtgaggaag acgatcttaa agtcgagagg atgaagaaac actgtgtgtc    6780
cctcggcttt cacaacatca atggcaaagt atactgcaaa atctgggata agtctaccgg    6840
tgacaccttt tacaccgatg attcccggta tacccaagac tatgcttttc aggacaggtc    6900
agccgactac agagacaggg actatgaagg tgtgcaaacc gccccccaac agggctttga    6960
tccaaagtct gaaaccccctg ttggcactgt agtgatcggc ggtattacgt ataataggta    7020
cctgatcaaa ggtaaggaga tcctggttcc caagcctgac aactgccttg aagctgccaa    7080
gctgtccctt gagcaagctc tcgctgggat gggtcaaact tgtgacctca cagctgccga    7140
ggtggaaaag ctaaagcgta tcattagtca actccaaggt ttgaccactg aacaggcttt    7200
aaactgttag ccgccagtgg cttgacccgc tgtggccgcg gcggcttagt tgtaactgaa    7260
acggcggtaa aaattgtaaa ataccacagc agaactttca cctttggccc tcttgacctg    7320
aaagttactt ccgaggcgga ggtaaagaaa tcaactgagc agggccacgc tgttgtggca    7380
aacttatgtt cgggtgtcat cttgatgaga cctcacccac cgtcccttgt tgacgttctt    7440
ctgaaacccg gacttgacac aaaacccggc attcaaccag gcatgggggc cgggaatatg    7500
ggcgtggacg gttctatgtg ggattttgaa accgcaccca caaggcaga actcgagtta    7560
tccaagcaaa taattcaagc atgtgaagtt aggcgcgggg acgccccgaa cctccaactt    7620
ccttataagc tctatcctgt tagggggggat cctgcgcggc atgggggccg ccttatcaat    7680
accaggtttg gagatttatc ttacaaaact cctcaagaca ccaagtccgc aatccacgcg    7740
gcttgttgcc tgcaccccaa cggggcccct gtgtctgatg gtaaatcaac actaggtacc    7800
actctccaac atggtttcga gctttatgtc cccactgtac cttatagtgt catggagtac    7860
ctcgattcac gccctgacac cccttttatg tgtactaagc atggcacttc caaggctgct    7920
gcagaggacc tccaaaaata cgacctgtcc actcagggat tcgtcctgcc tggggtctta    7980
```

-continued

```
cgcctagtac gtagattcat ctttggccat attggtaagg cgccgccatt gttccttcca    8040
tcaacctatc ccgccaaaaa ctctatggca gggatcaatg ccagaggtt tccaacaaag     8100
gacgttcaga gcatacctga aattgatgaa atgtgtgccc cgccgtcaa ggagaattgg     8160
caaactgtga caccttgtac tctcaagaaa cagtactgtt ccaagcccaa aaccaggacc    8220
atcctgggca ccaacaactt tattgccttg gctcacagat cggcgctcag tggtgtcacc    8280
caggcattca tgaagaaggc ctggaagtcc ccaattgcct tgggaaaaaa caaattcaag    8340
gagctgcatt gcaccgtcgc cggcaggtgt cttgaggccg acttggcctc ctgtgaccgc    8400
agcacccccg ccattgtaag atggttcgtc gccaacctcc tgtatgaact gcaggatgt     8460
gaagagtact tgcctagcta tgtgcttaat tgctgccatg accttgtggc aacacaggat    8520
ggtgccttca caaaacgcgg tggcctgtcg tccggggacc ccgtcaccag tgtgtccaac    8580
accgtatatt cactggtgat ttatgcccag cacatggtgt tgtcggcctt gaaaatgggt    8640
catgaaatcg gtctcaagtt cctcgaggaa cagctcaaat ttgaggacct cctcgaaatt    8700
cagcctatgc tggtatactc tgatgacctt gtcttgtacg ctgaaagacc cacttttcct    8760
aattaccact ggtgggtcga gcaccttgac ctaatgctgg gtttcagaac ggacccaaag    8820
aaaactgtca taactgataa acccagcttc ctcggctgca gaattgaggc agggcgacag    8880
ctggttccca atcgcgaccg catcctggct gctctcgcat accacatgaa ggcgcagaac    8940
gcctcagagt attatgcgtc tgctgccgca atcctgatgg attcatgcgc ttgcattgac    9000
catgaccctg agtggtatga ggacctcatc tgcggtattg cccaatgcgc ccgccaggat    9060
ggttatagct tcccaggtcc ggcatttttc atgtccatgt gggagaggct gagaagtcat    9120
aatgaaggga agaaatttcg ccactgcggc atctgcgatg ccaaagctga ctatgcatcc    9180
gcctgtgggc ttgatttgtg tttgtttcat tcgcactttc atcaacactg tcctgtcact    9240
ctgagctgcg gtcatcatgc cggttcaagg gaatgttcgc agtgtcagtc acctgttggg    9300
gctggcagat cccctcttga tgccgtgtta aaacaaattc catataaacc tcctcgtact    9360
gtcatcatga aggtgggtaa caaaacaacg gctctcgatc cggggaggta ccaatcccgt    9420
cgaggtctcg ttgcagtcaa gagaggtatt gcaggcaatg aggttgatct ttccgatgga    9480
gactaccaag tggtgcctct tttgccgact tgcaaagaca taaacatggt gaaggtggct    9540
tgtaatgtac tactcagtaa gttcatagtg gggccaccag gttccggaaa gaccacctgg    9600
ttactaggtc aagtccagga cgatgatgtc atttacacac ccacccatca gactatgttt    9660
gatatagtca gtgctctcaa agtttgcagg tataccatcc caggagcctc aggacttcct    9720
ttcccaccac ccgccaggtc cggaccgtgg gttaggctca tagccagcgg gcacgtccct    9780
ggccgagtat catacctcga tgaggctgga tactgtaatc atttggacat tctcagactg    9840
ctctccaaaa caccccttgt gtgtttgggt gaccttcaac aacttcaccc tgtcggcttt    9900
gattcctact gttatgtgtt tgatcagatg cctcagaagc aactgaccac catttacaga    9960
tttggcccta acatctgcgc ggccattcag ccttgctaca gggagaagct tgaatctaag   10020
gctaggaaca ccagggtggt ttttaccacc cggcctgtgg cctttggtca ggtgctgaca   10080
ccataccata aagatcgcat cggctctgcg ataaccatag actcatccca ggggccacc    10140
tttgatattg tgacattgca tctaccatcg ccaaaatctc taaacaaatc ccgagcactt   10200
gtggccatca ctcgggcaag acacgggtt tcatttatg accctcataa tcagcttcag    10260
gagttttca acctaaccc tgagcgtact gattgcaacc ttgtgttcag ccgtgggat     10320
```

```
gagctagtag ttctggatgc ggataatgca gtcacaactg tggcgaaggc cctagaaaca    10380
ggtccatctc gatttcgagt gtcagacccg aggtgcaagt ctctcttagc cgcttgttcg    10440
gccagtctgg aggggagctg tatgccacta ccgcaagtgg cacataactt ggggttttac    10500
ttttccccgg acagtccagc atttgcacct ctgccaagag agttggcgcc acattggcca    10560
gtagttaccc accagaataa tcgggcgtgg cctgatcgac ttgtcgctag tatgcgccca    10620
attgatgccc gctacagcaa gccaatggtc ggtgcagggt atgtggtcgg gccgtccacc    10680
tttcttggta ctcctggtgt ggtgtcatat tatctcacgc tgtacatcag gggtgagccc    10740
caggctttgc cagaaacact cgtttcaaca ggacgtatag ctacagattg tcgggagtat    10800
ctcgacgcgg ctgaggaaga ggcagcaaaa gaactccccc acgcatttat tggcgatgtc    10860
aaaggtacca cggtgggggg ttgtcatcac atcacatcaa agtacctacc taggtccctg    10920
cctaaggact ctattgccgt agttggagta agttcgcccg gcagggctgc taaagccatg    10980
tgcactctca ccgatgtgta tctccccgaa ctccggccct atctgcaacc tgagacggca    11040
tcaaaatgct ggaaactcaa attagacttc agggacgtcc gactaatggt ctggaaagga    11100
gccaccgcct atttccagtt ggaagggttt acatggtcgg cgctgcctga ctatgccagg    11160
tttattcagc tgcccaagga tgccgttgta tacattgatc cgtgtatagg accggcaaca    11220
gccaaccgca aggtcgtgcg aaccacagac tggcgggccg acctggcagt gacaccgtat    11280
gattacggtg cccagaacat tttgacaaca gcctggttcg aggacctcgg gccgcagtgg    11340
aagattttag ggttgcagcc cttttaggcga gcgtttggcc ttgaaaacac tgaggattgg    11400
gcaatccttg cacgtcgtat gaatgacggc aaggactaca ctgactataa ctggaactgt    11460
gttcgagaac gctcacacgc catctacgga cgtgctcgtg accatacata tcattttgcc    11520
cccggcacgg aactgcaggt ggagctaggt aaacccggc tgccgcctgg gcaggtgccg    11580
tgaatttgga gtaatgcaat ggggtcactg tggagtaaga tcagccagct gttcgtggac    11640
gccttcactg agttccttgt tagtgtggtt gatattgtca ttttcttgc catactgttt    11700 gggttcaccg tcgcaggatg gttattggtc tttcttctca gagtggtttg ctccgcgctt    11760
ctccgttcgc gctctgccat tcactctccc gaactatcga aggtcctatg aaggcttgtt    11820
gcccaactgc agaccggacg tcccacaatt tgcagttaag cacccactgg gtatgttttg    11880
gcacatgcga gtttcccact tgattgatga gatggtctct cgccgcattt accagaccat    11940
ggaacattca ggacaagcgg catgaaagca tgtggttggt gaggccactc tcacgaagct    12000
ttcagggctc gacatagtta cccatttcca acacctggcc gcagtggagg cggattcttg    12060
tcgctttctc agctcacgac tcgtgatgct aaagaatctt gccgttggca atgtgagcct    12120
acagtacaac accacgctga accgcgttga gctcattttc cccacgccag gcacgaggcc    12180
caagttgacc gacttcagac aatggctcat cagtgtgcac gcttccattt tttcctctgt    12240
ggcttcatct gttactttgt tcacagtgct ttggcttcga attccagctc tacgctatgt    12300
ttttggtttc cattggccca cggcaacaca tcattcgagc tgaccatcaa ctacaccgta    12360
tgcatgccct gtcctaccag tcaagcagct ctccaaaggc tcgagcccgg tcgtaacatg    12420
tggtgcaaaa tagggcatga taggtgtgag gagcgtgacc aagatgagtt gttaatgtcc    12480
atcccgtccg ggtacgacaa cctcaaactt gagggttatt atgcttggct ggcttttttg    12540 tcttttttcct acgcggccca attccatcca gagttgttcg ggatcggaaa tgtgtcgcgc    12600
gtcttcgtgg acaagtggca ccagttcatt tgtgccgagc atgatggatc caattcaacc    12660
gtatctaccg gacacaacat ctccgcatta tatgcggcat attaccacca ccaaatagac    12720
```

-continued

```
gggggtaatt ggtttcattt ggaatggctg cggccattct tttcctcctg gctggtgctc    12780
aacatatcat ggtttctgag gcgttcgcct gtaagccctg tttctcgacg catctatcag    12840
atattaagac caacacgacc gcagctgccg gtttcatggt ccttcaggac atcaattgtt    12900
tccgacctca tgaggtctca gcaacgcaaa gggaaattcc cttcaggaag tcgtcccaat    12960
gccgtgaagc cgtcggcact ccccaatata tcacgataac agctaacgtg accgacgaat    13020
catatttgta caacgcggat tgctgatgcc tttctgcgtg ccttttctac gcttcagaaa    13080
tgagcgagaa aggcttcaaa gtcatctttg ggaatgtctc tggcgttgtt tctgcttgtg    13140
tcaatttcac ggattatgtg gcccatgtga cccaacatac ccagcagcat catctggtga    13200
ttgatcacat tcggctgctg catttcctga caccatctac aatgaggtgg gctacaacca    13260
ttgcctgttt gttcgccatt ctcttggcga tatgagatgt tcttacaaat tgggcgttc    13320 cttgattctg cactcttgct cctggtggtt ttttttgctg tgtaccggct tgtcttggtc    13380 cttttgccgat ggcaacggca acaactcgac ataccaatac atatataatt tgacgatatg    13440
cgagttaaat gggaccaatt ggctttccgg ccatttgat tgggcagttg agacctttgt    13500
gctttacccg gtcgtcactc atatcctctc actgggtttt ctcacgacaa gtcatttttt    13560
tgacgcgctc ggtctcggcg ctgtgtccac cgcaggattt attgacgggc ggtatgtgct    13620
cagcagcatc tacggcgctt gtgctttcgc agcgttcgta tgttttgtca tccgtgctgc    13680
taaaaattgc atggcctgcc gttacgcccg tacccggttt accaacttta ttgtggacga    13740
ccggggagga gttcatcggt ggaagtctcc aatagtggta gaaaaattgg gcaaagccga    13800
catcgacggc agccttgtca ccatcaaaca tgtcgtcctc gaaggggtta aagctcaacc    13860
cttgacaagg acttcggctg agcaatggga ggcctagatg attttgcaa tgatcccacc    13920 gccgcacaaa agctcgtgct agcctttagc atcacataca cacctataat gatatacgcc    13980
cttaaggtgt cacgcggccg actcctgggg ctattgcaca tcctaatatt tctgaactgt    14040
tccttcacat tcggatacat gacatatgtg cattttcaat ccgccaaccg tgtcgcactt    14100
accctggggg ctgttgtcgc ccttctgtgg ggcgtttaca gcctcacaga gtcatggaag    14160
tttatcactt ccagatgcag attgtgttgc cttggccggc gatacattct ggcccctgcc    14220
catcacgtag aaagtgctgc aggtctccat tcaatctcag cgtctggtaa ccgagcatac    14280
gctgtgagaa agcccggatt aacatcagtg aacggcactc tagtaccagg acttcggagc    14340
ctcgtgctgg gcggcaaacg agctgttaaa cgaggagtgg ttaacctcgt caaatatggc    14400
cggtaaaaac cagagccaga agaaaaagaa aagtacagct ccaatgggga atggccagcc    14460
agtcaatcaa ctgtgccagt tgctgggtgc aatgataaag tcccagcgcc agcagcctag    14520
aggaggacag gccaaaaaga aaagcctga gaagccacat ttcccccctgg ctgcagaaga    14580 tgacatccgg catcaccta cccagactga acgttctctc tgcttgcaat cgatccagac    14640
ggctttcaat caaggcgcgg gaactgcgtc gctttcatcc agcgggaagg tcagttttca    14700
ggttgagttc atgctgccgg ttggtcatac agtgcgcctg attcgcgtga cttctacatc    14760
cgccagtcag ggtgcaagtt aatttgacag tcaggtgaat ggtcgcgatt ggcgtgtgac    14820
ctctgagtca cctattcaat tagggcgatc acatgggggt catacttaat caggcaggaa    14880
ccatgtgacc gaaatt                                                   14896
```

<210> SEQ ID NO 2
<211> LENGTH: 2402
<212> TYPE: PRT

<213> ORGANISM: Porcine reproductive and respiratory syndrome virus

<400> SEQUENCE: 2

```
Leu Leu Trp Gly Gly Thr Pro Glu Asp Phe Arg Arg Gly Pro Ala Leu
 1               5                  10                  15

Leu Asp Val His Pro Leu Thr Met Cys Gly Ser Val Ser Arg Cys Met
             20                  25                  30

Cys Thr Pro Ala Val Arg Val Phe Trp Asn Ala Gly Gln Val Phe Cys
         35                  40                  45

Thr Arg Cys Val Ser Ala Arg Ala Leu Leu Ser Pro Glu Leu Gln Asp
     50                  55                  60

Thr Asp Leu Gly Ala Val Gly Leu Phe Tyr Arg Pro Arg Asp Lys Leu
 65                  70                  75                  80

His Trp Lys Val Pro Ile Gly Ile Pro Gln Ala Glu Cys Thr Pro Ser
                 85                  90                  95

Gly Cys Cys Trp Leu Ser Ala Val Phe Pro Leu Ala Arg Met Thr Ser
            100                 105                 110

Gly Asn His Asn Phe Leu Gln Arg Leu Val Lys Val Ala Asp Val Leu
        115                 120                 125

Tyr Arg Asp Gly Cys Leu Ala Pro Arg His Leu Arg Glu Leu Gln Val
    130                 135                 140

Tyr Glu Arg Gly Cys Asn Trp Tyr Pro Ile Thr Gly Pro Val Pro Gly
145                 150                 155                 160

Met Gly Leu Phe Ala Asn Ser Met His Val Ser Asp Gln Pro Phe Pro
                165                 170                 175

Gly Ala Thr His Val Leu Thr Asn Ser Pro Leu Pro Gln Gln Ala Cys
            180                 185                 190

Arg Gln Pro Phe Cys Pro Phe Glu Glu Ala His Ser Gly Val Tyr Arg
        195                 200                 205

Trp Lys Lys Phe Ile Phe Ser Asp Ser Pro Leu Asn Gly Gln Ser
    210                 215                 220

Arg Ile Met Trp Thr Pro Lys Ser Asp Asp Ser Ala Ala Leu Glu Glu
225                 230                 235                 240

Leu Pro Pro Glu Leu Glu Arg Gln Val Glu Ile Leu Ile Arg Ser Phe
                245                 250                 255

Pro Ala His His Pro Val Asn Leu Ala Asp Trp Glu Leu Thr Gly Ser
            260                 265                 270

Pro Glu Asn Gly Phe Ser Phe Asn Thr Ser His Ser Cys Gly His Leu
        275                 280                 285

Val Arg Asn Ser Asn Val Phe Asp Gly Lys Cys Trp Leu Thr Cys Phe
    290                 295                 300

Leu Gly Gln Ser Val Glu Val Arg Cys His Glu Glu His Leu Ala Asn
305                 310                 315                 320

Ala Phe Gly Tyr Gln Thr Lys Trp Gly Val His Gly Lys Tyr Leu Gln
                325                 330                 335

Arg Arg Leu Gln Val Arg Gly Ile Arg Ala Val Val Asp Pro Asp Gly
            340                 345                 350

Pro Ile His Val Glu Ala Leu Ser Cys Ser Gln Ser Trp Ile Arg His
        355                 360                 365

Leu Thr Leu Asn Asp Asp Val Thr Pro Gly Phe Val Arg Leu Thr Ser
    370                 375                 380

Ile Arg Ile Val Pro Asn Thr Glu Pro Thr Thr Ser Gln Ile Phe Arg
385                 390                 395                 400
```

-continued

```
Phe Gly Ala His Lys Trp Tyr Gly Ala Gly Lys Arg Ala Arg Ala
                405                 410                 415
Lys Arg Thr Ala Lys Gly Lys Asp Ser Val Pro Ala Leu Lys Val
            420                 425                 430
Ala Leu Pro Val Pro Ala Cys Gly Ile Thr Thr Tyr Ser Pro Pro Thr
        435                 440                 445
Asp Gly Ser Cys Gly Trp His Val Leu Ala Ala Ile Met Asn Arg Met
450                 455                 460
Met Asn Asp Asp Phe Thr Ser Pro Leu Thr Gln Tyr Asn Arg Pro Glu
465                 470                 475                 480
Asp Asp Trp Ala Ser Asp Tyr Asp Leu Ala Gln Ala Ile Gln Cys Leu
                485                 490                 495
Gln Leu Pro Ala Thr Val Val Arg Asn Arg Ala Cys Pro Asn Ala Lys
            500                 505                 510
Tyr Leu Ile Lys Leu Asn Gly Val His Trp Glu Val Glu Val Arg Ser
        515                 520                 525
Gly Met Ala Pro Arg Ser Leu Ser Arg Glu Cys Val Val Gly Val Cys
    530                 535                 540
Ser Glu Gly Cys Val Ala Pro Pro Tyr Pro Ala Asp Gly Leu Pro Lys
545                 550                 555                 560
Arg Ala Leu Glu Ala Leu Ala Ser Ala Tyr Arg Leu Pro Ser Asp Cys
                565                 570                 575
Val Cys Ser Gly Ile Ala Asp Phe Leu Ala Asn Pro Pro Gln Glu
            580                 585                 590
Phe Trp Thr Leu Asp Lys Met Leu Thr Ser Pro Glu Arg Ser
        595                 600                 605
Gly Phe Ser Ser Leu Tyr Asn Leu Leu Leu Glu Val Val Pro Gln Lys
    610                 615                 620
Cys Gly Val Thr Glu Gly Ala Phe Thr Tyr Ala Val Glu Arg Met Leu
625                 630                 635                 640
Met Asp Cys Pro Ser Ser Gln Ala Met Ala Leu Leu Ala Lys Ile
                645                 650                 655
Lys Val Pro Ser Ser Lys Ala Pro Ser Val Ser Leu Asp Glu Cys Phe
            660                 665                 670
Pro Ala Asp Val Pro Ala Asp Phe Glu Pro Thr Ser Gln Lys Arg Pro
        675                 680                 685
Gln Ser Ser Gly Ala Ala Val Ala Leu Cys Ser Ser Asp Ala Glu Gly
    690                 695                 700
Phe Glu Glu Ala Ala Pro Glu Gly Val Gln Glu Arg Gly His Lys Ala
705                 710                 715                 720
Val His Ser Ala Leu Phe Ala Lys Gly Pro Asn Asn Glu Gln Val Gln
                725                 730                 735
Val Val Ala Gly Glu Gln Gln Lys Leu Gly Gly Cys Gly Leu Ala Ile
            740                 745                 750
Gly Asn Ala Gln Ser Pro Leu Asn Ser Met Lys Glu Asn Met Arg Ser
        755                 760                 765
Ser Arg Glu Asp Glu Pro Leu Asp Leu Ser Gln Pro Ala Pro Val Ala
    770                 775                 780
Ala Thr Thr Leu Glu Arg Glu Gln Thr Pro Asp Asn Pro Gly Ser Asp
785                 790                 795                 800
Ala Gly Ala Leu Pro Ala Thr Val Arg Glu Ser Val Pro Thr Gly Pro
                805                 810                 815
Met Leu Arg His Val Glu His Cys Gly Thr Glu Ser Gly Asp Ser Ser
```

-continued

```
              820                 825                 830
Ser Pro Leu Asp Leu Ser Tyr Ala Gln Thr Leu Asp Gln Pro Leu Asp
            835                 840                 845

Leu Ser Leu Ala Val Trp Pro Val Lys Ala Thr Ala Ser Asp Pro Gly
        850                 855                 860

Trp Val His Gly Arg Arg Glu Pro Val Phe Val Lys Pro Arg Lys Ala
865                 870                 875                 880

Phe Ser Asp Ser Asp Ser Ala Phe Gln Phe Gly Lys Leu Ser Glu Ser
                885                 890                 895

Gly Ser Val Ile Glu Phe Asp Arg Thr Lys Asp Ala Pro Val Val Asp
            900                 905                 910

Ala Pro Val Gly Ser Thr Thr Ser Asn Glu Ala Leu Ser Ile Ala Asp
        915                 920                 925

Pro Phe Glu Phe Ala Glu Leu Lys Arg Pro Arg Phe Ser Ala Gln Ala
    930                 935                 940

Leu Ile Asp Arg Gly Gly Pro Leu Ala Asp Val His Ala Lys Ile Lys
945                 950                 955                 960

Asn Arg Val Tyr Glu Arg Cys Leu Gln Ala Cys Glu Pro Gly Ser Arg
                965                 970                 975

Ala Thr Pro Ala Thr Lys Glu Trp Leu Asp Lys Met Trp Asp Arg Val
            980                 985                 990

Asp Met Lys Thr Trp Cys Cys Thr Ser Gln Phe Gln Ala Gly Arg Ile
        995                 1000                1005

Leu Ala Ser Leu Lys Phe Leu Pro Asp Met Ile Gln Asp Thr Pro Pro
    1010                1015                1020

Pro Val Pro Arg Lys Asn Arg Ala Ser Asp Asn Ala Asp Leu Lys Gln
1025                1030                1035                1040

Leu Val Ala Gln Trp Asp Arg Lys Leu Ser Met Thr Pro Pro Gln Lys
                1045                1050                1055

Pro Val Glu Pro Val Leu Asp Gln Thr Val Ser Pro Pro Thr Asp Thr
            1060                1065                1070

Gln Gln Glu Asp Val Thr Pro Ser Asp Gly Pro Pro His Ala Pro Asp
        1075                1080                1085

Phe Pro Ser Arg Val Ser Thr Gly Gly Ser Trp Lys Asp Leu Met Cys
    1090                1095                1100

Ser Gly Thr Arg Leu Ala Gly Ser Ile Ser Gln Arg Leu Met Thr Trp
1105                1110                1115                1120

Val Phe Glu Val Phe Ser His Leu Pro Ala Phe Met Leu Thr Leu Phe
                1125                1130                1135

Ser Pro Arg Gly Ser Met Ala Pro Gly Asp Trp Leu Phe Ala Gly Val
            1140                1145                1150

Val Leu Leu Ala Leu Leu Leu Cys His Ser Tyr Pro Ile Leu Gly Cys
        1155                1160                1165

Leu Pro Leu Leu Gly Val Phe Ser Gly Ser Leu Arg Arg Val Arg Leu
    1170                1175                1180

Gly Val Phe Gly Ser Trp Met Ala Phe Ala Val Phe Leu Phe Ser Thr
1185                1190                1195                1200

Pro Ser Asn Pro Val Gly Ser Ser Cys Asp His Asp Ser Pro Glu Cys
                1205                1210                1215

His Ala Glu Leu Leu Ala Leu Glu Gln Arg Gln Leu Trp Glu Pro Val
            1220                1225                1230

Arg Gly Leu Val Val Gly Pro Ser Gly Leu Leu Cys Val Ile Leu Gly
        1235                1240                1245
```

-continued

Lys Leu Leu Gly Gly Ser Arg Tyr Leu Trp His Ile Leu Leu Arg Leu
    1250                1255                1260

Cys Met Leu Thr Asp Leu Ala Leu Ser Leu Val Tyr Val Val Ser Gln
1265                1270                1275                1280

Gly Arg Cys His Lys Cys Trp Gly Lys Cys Ile Arg Thr Ala Pro Thr
                1285                1290                1295

Glu Val Ala Leu Asn Val Phe Pro Phe Thr Arg Ala Thr Arg Ser Ser
            1300                1305                1310

Leu Val Ser Leu Cys Asp Arg Phe Gln Thr Pro Lys Gly Val Asp Pro
        1315                1320                1325

Val His Leu Ala Thr Gly Trp Arg Gly Cys Trp Arg Gly Gly Ser Pro
    1330                1335                1340

Val His Gln Pro His Gln Lys Pro Ile Ala Tyr Ala Asn Leu Asp Glu
1345                1350                1355                1360

Lys Lys Ile Ser Ala Gln Thr Val Val Ala Val Pro Tyr Asp Pro Ser
                1365                1370                1375

Gln Ala Ile Lys Cys Leu Lys Val Leu Gln Ala Gly Gly Ala Ile Val
            1380                1385                1390

Asp Gln Pro Thr Pro Glu Val Val Arg Val Ser Glu Ile Pro Phe Ser
        1395                1400                1405

Ala Pro Phe Phe Pro Lys Val Pro Val Asn Pro Asp Cys Arg Val Val
    1410                1415                1420

Val Asp Ser Asp Thr Phe Val Ala Ala Val Arg Cys Gly Tyr Ser Thr
1425                1430                1435                1440

Ala Gln Leu Val Leu Gly Gln Gly Asn Phe Ala Lys Leu Asn Gln Thr
                1445                1450                1455

Pro Pro Arg Asn Ser Thr Ser Thr Lys Thr Thr Gly Gly Ala Ser Tyr
            1460                1465                1470

Thr Leu Ala Val Ala Gln Val Thr Val Trp Thr Leu Phe His Phe Ile
        1475                1480                1485

Leu Gly Leu Trp Phe Thr Ser Pro Gln Val Cys Gly Arg Gly Thr Ala
    1490                1495                1500

Asp Pro Trp Cys Ser Asn Pro Phe Ser Tyr Pro Thr Tyr Gly Pro Gly
1505                1510                1515                1520

Val Val Cys Ser Ser Arg Leu Cys Val Ser Ala Asp Gly Val Thr Leu
                1525                1530                1535

Pro Leu Phe Ser Ala Val Ala Gln Leu Ser Gly Arg Glu Val Gly Ile
            1540                1545                1550

Phe Ile Leu Val Leu Val Ser Leu Ile Ala Leu Ala His Arg Met Ala
        1555                1560                1565

Leu Lys Ala Asp Met Leu Val Val Phe Leu Ala Phe Cys Ala Tyr Ala
    1570                1575                1580

Trp Pro Met Ser Ser Trp Leu Ile Cys Phe Phe Pro Leu Leu Leu Lys
1585                1590                1595                1600

Trp Val Thr Leu His Pro Leu Thr Met Leu Trp Val His Ser Phe Leu
                1605                1610                1615

Val Phe Cys Leu Pro Ala Ala Gly Ile Leu Ser Leu Gly Thr Thr Gly
            1620                1625                1630

Leu Leu Trp Ala Ile Gly Arg Phe Thr Gln Val Ala Gly Ile Ile Thr
        1635                1640                1645

Pro Tyr Asp Ile His Gln Tyr Thr Ser Gly Pro Arg Gly Ala Ala Ala
    1650                1655                1660

-continued

```
Val Ala Thr Ala Pro Glu Gly Thr Tyr Met Ala Ala Val Arg Arg Ala
1665                1670                1675                1680

Ala Leu Thr Gly Arg Thr Leu Ile Phe Thr Pro Ser Ala Val Gly Ser
                1685                1690                1695

Leu Leu Glu Gly Ala Phe Arg Thr Gln Lys Pro Cys Leu Asn Thr Val
            1700                1705                1710

Asn Val Val Gly Ser Ser Leu Gly Ser Gly Gly Val Phe Thr Ile Asn
        1715                1720                1725

Gly Arg Arg Thr Val Val Thr Ala Ala His Val Leu Asn Gly Asp Thr
    1730                1735                1740

Ala Arg Val Thr Gly Asp Ser Tyr Asn Arg Met His Thr Phe Lys Thr
1745                1750                1755                1760

Asn Gly Asp Tyr Ala Trp Ser His Ala Asp Asp Trp Gln Gly Val Ala
                1765                1770                1775

Pro Val Val Lys Val Ala Lys Gly Tyr Arg Gly Arg Ala Tyr Trp Gln
            1780                1785                1790

Thr Ser Thr Gly Val Glu Pro Gly Ile Ile Gly Glu Gly Phe Ala Phe
        1795                1800                1805

Cys Phe Thr Asn Cys Gly Asp Ser Gly Ser Pro Val Ile Ser Glu Ser
    1810                1815                1820

Gly Asp Leu Ile Gly Ile His Thr Gly Ser Asn Lys Leu Gly Ser Gly
1825                1830                1835                1840

Leu Val Thr Thr Pro Glu Gly Glu Thr Cys Ala Ile Lys Glu Thr Lys
                1845                1850                1855

Leu Ser Asp Leu Ser Arg His Phe Ala Gly Pro Ser Val Pro Leu Gly
            1860                1865                1870

Asp Ile Lys Leu Ser Pro Ala Ile Ile Pro Asp Val Thr Ser Ile Pro
        1875                1880                1885

Ser Asp Leu Ala Ser Leu Leu Ala Ser Val Pro Val Leu Glu Gly Gly
    1890                1895                1900

Leu Ser Thr Val Gln Leu Leu Cys Val Phe Phe Leu Leu Trp Arg Met
1905                1910                1915                1920

Met Gly His Ala Trp Thr Pro Ile Val Ala Val Gly Phe Phe Leu Leu
                1925                1930                1935

Asn Glu Ile Leu Pro Ala Val Leu Val Arg Ala Val Phe Ser Phe Ala
            1940                1945                1950

Leu Phe Val Leu Ala Trp Val Thr Pro Trp Ser Ala Gln Val Leu Met
        1955                1960                1965

Ile Arg Leu Leu Thr Ala Ser Leu Asn Arg Asn Lys Phe Ser Leu Ala
    1970                1975                1980

Phe Tyr Ala Leu Gly Gly Val Ile Gly Leu Ala Ala Glu Ile Gly Thr
1985                1990                1995                2000

Phe Ala Gly Arg Leu Pro Glu Leu Ser Gln Ala Leu Ser Thr Tyr Cys
                2005                2010                2015

Phe Leu Pro Arg Val Leu Ala Met Ala Ser Cys Val Pro Ile Ile Ile
            2020                2025                2030

Ile Gly Gly Leu His Thr Leu Gly Val Ile Leu Trp Leu Phe Lys Tyr
        2035                2040                2045

Arg Cys Leu His Asn Met Leu Val Gly Asp Gly Ser Phe Ser Ser Ala
    2050                2055                2060

Phe Phe Leu Arg Tyr Phe Ala Glu Gly Asn Leu Arg Lys Gly Val Ser
2065                2070                2075                2080

Gln Ser Cys Gly Met Asn Asn Glu Ser Leu Thr Ala Ala Leu Ala Cys
```

2085                2090                2095
Lys Leu Ser Gln Ala Asp Leu Asp Phe Leu Ser Ser Leu Thr Asn Phe
            2100                2105                2110
Lys Cys Phe Val Ser Ala Ser Asn Met Lys Asn Ala Ala Gly Gln Tyr
        2115                2120                2125
Ile Glu Ala Ala Tyr Ala Arg Ala Leu Arg Gln Glu Leu Ala Ser Leu
    2130                2135                2140
Val Gln Val Asp Lys Met Lys Gly Val Leu Ser Lys Leu Glu Ala Phe
2145                2150                2155                2160
Ala Glu Thr Ala Thr Pro Ser Leu Asp Thr Gly Asp Val Val Val Leu
            2165                2170                2175
Leu Gly Gln His Pro His Gly Ser Ile Leu Asp Ile Asn Val Gly Thr
        2180                2185                2190
Glu Arg Lys Thr Val Ser Val Gln Glu Thr Arg Ser Leu Gly Gly Ser
    2195                2200                2205
Lys Phe Ser Val Cys Thr Val Val Ser Asn Thr Pro Val Asp Ala Leu
    2210                2215                2220
Thr Gly Ile Pro Leu Gln Thr Pro Thr Pro Leu Phe Glu Asn Gly Pro
2225                2230                2235                2240
Arg His Arg Ser Glu Glu Asp Asp Leu Lys Val Glu Arg Met Lys Lys
            2245                2250                2255
His Cys Val Ser Leu Gly Phe His Asn Ile Asn Gly Lys Val Tyr Cys
        2260                2265                2270
Lys Ile Trp Asp Lys Ser Thr Gly Asp Thr Phe Tyr Thr Asp Asp Ser
    2275                2280                2285
Arg Tyr Thr Gln Asp Tyr Ala Phe Gln Asp Arg Ser Ala Asp Tyr Arg
    2290                2295                2300
Asp Arg Asp Tyr Glu Gly Val Gln Thr Ala Pro Gln Gln Gly Phe Asp
2305                2310                2315                2320
Pro Lys Ser Glu Thr Pro Val Gly Thr Val Val Ile Gly Gly Ile Thr
            2325                2330                2335
Tyr Asn Arg Tyr Leu Ile Lys Gly Lys Glu Ile Leu Val Pro Lys Pro
        2340                2345                2350
Asp Asn Cys Leu Glu Ala Ala Lys Leu Ser Leu Glu Gln Ala Leu Ala
    2355                2360                2365
Gly Met Gly Gln Thr Cys Asp Leu Thr Ala Ala Glu Val Glu Lys Leu
    2370                2375                2380
Lys Arg Ile Ile Ser Gln Leu Gln Gly Leu Thr Thr Glu Gln Ala Leu
2385                2390                2395                2400
Asn Cys

<210> SEQ ID NO 3
<211> LENGTH: 1458
<212> TYPE: PRT
<213> ORGANISM: Porcine reproductive and respiratory syndrome virus

<400> SEQUENCE: 3

Leu Ala Ala Ser Gly Leu Thr Arg Cys Gly Arg Gly Gly Leu Val Val
 1               5                  10                  15
Thr Glu Thr Ala Val Lys Ile Val Lys Tyr His Ser Arg Thr Phe Thr
            20                  25                  30
Phe Gly Pro Leu Asp Leu Lys Val Thr Ser Glu Ala Glu Val Lys Lys
        35                  40                  45
Ser Thr Glu Gln Gly His Ala Val Val Ala Asn Leu Cys Ser Gly Val

-continued

```
                50                    55                    60
Ile Leu Met Arg Pro His Pro Ser Leu Val Asp Val Leu Lys
 65                    70                    75                    80

Pro Gly Leu Asp Thr Lys Pro Gly Ile Gln Pro Gly His Gly Ala Gly
                       85                    90                    95

Asn Met Gly Val Asp Gly Ser Met Trp Asp Phe Glu Thr Ala Pro Thr
                      100                   105                   110

Lys Ala Glu Leu Glu Leu Ser Lys Gln Ile Ile Gln Ala Cys Glu Val
                      115                   120                   125

Arg Arg Gly Asp Ala Pro Asn Leu Gln Leu Pro Tyr Lys Leu Tyr Pro
                      130                   135                   140

Val Arg Gly Asp Pro Ala Arg His Gly Gly Arg Leu Ile Asn Thr Arg
145                   150                   155                   160

Phe Gly Asp Leu Ser Tyr Lys Thr Pro Gln Asp Thr Lys Ser Ala Ile
                      165                   170                   175

His Ala Ala Cys Cys Leu His Pro Asn Gly Ala Pro Val Ser Asp Gly
                      180                   185                   190

Lys Ser Thr Leu Gly Thr Thr Leu Gln His Gly Phe Glu Leu Tyr Val
                      195                   200                   205

Pro Thr Val Pro Tyr Ser Val Met Glu Tyr Leu Asp Ser Arg Pro Asp
                      210                   215                   220

Thr Pro Phe Met Cys Thr Lys His Gly Thr Ser Lys Ala Ala Ala Glu
225                   230                   235                   240

Asp Leu Gln Lys Tyr Asp Leu Ser Thr Gln Gly Phe Val Leu Pro Gly
                      245                   250                   255

Val Leu Arg Leu Val Arg Arg Phe Ile Phe Gly His Ile Gly Lys Ala
                      260                   265                   270

Pro Pro Leu Phe Leu Pro Ser Thr Tyr Pro Ala Lys Asn Ser Met Ala
                      275                   280                   285

Gly Ile Asn Gly Gln Arg Phe Pro Thr Lys Asp Val Gln Ser Ile Pro
                      290                   295                   300

Glu Ile Asp Glu Met Cys Ala Arg Ala Val Lys Glu Asn Trp Gln Thr
305                   310                   315                   320

Val Thr Pro Cys Thr Leu Lys Lys Gln Tyr Cys Ser Lys Pro Lys Thr
                      325                   330                   335

Arg Thr Ile Leu Gly Thr Asn Asn Phe Ile Ala Leu Ala His Arg Ser
                      340                   345                   350

Ala Leu Ser Gly Val Thr Gln Ala Phe Met Lys Lys Ala Trp Lys Ser
                      355                   360                   365

Pro Ile Ala Leu Gly Lys Asn Lys Phe Lys Glu Leu His Cys Thr Val
                      370                   375                   380

Ala Gly Arg Cys Leu Glu Ala Asp Leu Ala Ser Cys Asp Arg Ser Thr
385                   390                   395                   400

Pro Ala Ile Val Arg Trp Phe Val Ala Asn Leu Leu Tyr Glu Leu Ala
                      405                   410                   415

Gly Cys Glu Glu Tyr Leu Pro Ser Tyr Val Leu Asn Cys Cys His Asp
                      420                   425                   430

Leu Val Ala Thr Gln Asp Gly Ala Phe Thr Lys Arg Gly Gly Leu Ser
                      435                   440                   445

Ser Gly Asp Pro Val Thr Ser Val Ser Asn Thr Val Tyr Ser Leu Val
                      450                   455                   460

Ile Tyr Ala Gln His Met Val Leu Ser Ala Leu Lys Met Gly His Glu
465                   470                   475                   480
```

-continued

```
Ile Gly Leu Lys Phe Leu Glu Glu Gln Leu Lys Phe Glu Asp Leu Leu
            485                 490                 495
Glu Ile Gln Pro Met Leu Val Tyr Ser Asp Leu Val Leu Tyr Ala
            500                 505                 510
Glu Arg Pro Thr Phe Pro Asn Tyr His Trp Val Glu His Leu Asp
            515                 520                 525
Leu Met Leu Gly Phe Arg Thr Asp Pro Lys Lys Thr Val Ile Thr Asp
            530                 535                 540
Lys Pro Ser Phe Leu Gly Cys Arg Ile Glu Ala Gly Arg Gln Leu Val
545                 550                 555                 560
Pro Asn Arg Asp Arg Ile Leu Ala Ala Leu Ala Tyr His Met Lys Ala
            565                 570                 575
Gln Asn Ala Ser Glu Tyr Tyr Ala Ser Ala Ala Ile Leu Met Asp
            580                 585                 590
Ser Cys Ala Cys Ile Asp His Asp Pro Glu Trp Tyr Glu Asp Leu Ile
            595                 600                 605
Cys Gly Ile Ala Gln Cys Ala Arg Gln Asp Gly Tyr Ser Phe Pro Gly
            610                 615                 620
Pro Ala Phe Phe Met Ser Met Trp Glu Arg Leu Arg Ser His Asn Glu
625                 630                 635                 640
Gly Lys Lys Phe Arg His Cys Gly Ile Cys Asp Ala Lys Ala Asp Tyr
            645                 650                 655
Ala Ser Ala Cys Gly Leu Asp Leu Cys Leu Phe His Ser His Phe His
            660                 665                 670
Gln His Cys Pro Val Thr Leu Ser Cys Gly His His Ala Gly Ser Arg
            675                 680                 685
Glu Cys Ser Gln Cys Gln Ser Pro Val Gly Ala Gly Arg Ser Pro Leu
            690                 695                 700
Asp Ala Val Leu Lys Gln Ile Pro Tyr Lys Pro Pro Arg Thr Val Ile
705                 710                 715                 720
Met Lys Val Gly Asn Lys Thr Thr Ala Leu Asp Pro Gly Arg Tyr Gln
            725                 730                 735
Ser Arg Arg Gly Leu Val Ala Val Lys Arg Gly Ile Ala Gly Asn Glu
            740                 745                 750
Val Asp Leu Ser Asp Gly Asp Tyr Gln Val Val Pro Leu Leu Pro Thr
            755                 760                 765
Cys Lys Asp Ile Asn Met Val Lys Val Ala Cys Asn Val Leu Leu Ser
770                 775                 780
Lys Phe Ile Val Gly Pro Pro Gly Ser Gly Lys Thr Thr Trp Leu Leu
785                 790                 795                 800
Gly Gln Val Gln Asp Asp Val Ile Tyr Thr Pro Thr His Gln Thr
            805                 810                 815
Met Phe Asp Ile Val Ser Ala Leu Lys Val Cys Arg Tyr Thr Ile Pro
            820                 825                 830
Gly Ala Ser Gly Leu Pro Phe Pro Pro Ala Arg Ser Gly Pro Trp
            835                 840                 845
Val Arg Leu Ile Ala Ser Gly His Val Pro Gly Arg Val Ser Tyr Leu
            850                 855                 860
Asp Glu Ala Gly Tyr Cys Asn His Leu Asp Ile Leu Arg Leu Leu Ser
865                 870                 875                 880
Lys Thr Pro Leu Val Cys Leu Gly Asp Leu Gln Gln Leu His Pro Val
            885                 890                 895
```

-continued

```
Gly Phe Asp Ser Tyr Cys Tyr Val Phe Asp Gln Met Pro Gln Lys Gln
            900                 905                 910

Leu Thr Thr Ile Tyr Arg Phe Gly Pro Asn Ile Cys Ala Ala Ile Gln
            915                 920                 925

Pro Cys Tyr Arg Glu Lys Leu Glu Ser Lys Ala Arg Asn Thr Arg Val
            930                 935                 940

Val Phe Thr Thr Arg Pro Val Ala Phe Gly Gln Val Leu Thr Pro Tyr
945                 950                 955                 960

His Lys Asp Arg Ile Gly Ser Ala Ile Thr Ile Asp Ser Ser Gln Gly
            965                 970                 975

Ala Thr Phe Asp Ile Val Thr Leu His Leu Pro Ser Pro Lys Ser Leu
            980                 985                 990

Asn Lys Ser Arg Ala Leu Val Ala Ile Thr Arg Ala Arg His Gly Leu
            995                 1000                1005

Phe Ile Tyr Asp Pro His Asn Gln Leu Gln Glu Phe Phe Asn Leu Thr
            1010                1015                1020

Pro Glu Arg Thr Asp Cys Asn Leu Val Phe Ser Arg Gly Asp Glu Leu
1025                1030                1035                1040

Val Val Leu Asp Ala Asp Asn Ala Val Thr Thr Val Ala Lys Ala Leu
            1045                1050                1055

Glu Thr Gly Pro Ser Arg Phe Arg Val Ser Asp Pro Arg Cys Lys Ser
            1060                1065                1070

Leu Leu Ala Ala Cys Ser Ala Ser Leu Glu Gly Ser Cys Met Pro Leu
            1075                1080                1085

Pro Gln Val Ala His Asn Leu Gly Phe Tyr Phe Ser Pro Asp Ser Pro
            1090                1095                1100

Ala Phe Ala Pro Leu Pro Arg Glu Leu Ala Pro His Trp Pro Val Val
1105                1110                1115                1120

Thr His Gln Asn Asn Arg Ala Trp Pro Asp Arg Leu Val Ala Ser Met
            1125                1130                1135

Arg Pro Ile Asp Ala Arg Tyr Ser Lys Pro Met Val Gly Ala Gly Tyr
            1140                1145                1150

Val Val Gly Pro Ser Thr Phe Leu Gly Thr Pro Gly Val Val Ser Tyr
            1155                1160                1165

Tyr Leu Thr Leu Tyr Ile Arg Gly Glu Pro Gln Ala Leu Pro Glu Thr
            1170                1175                1180

Leu Val Ser Thr Gly Arg Ile Ala Thr Asp Cys Arg Glu Tyr Leu Asp
1185                1190                1195                1200

Ala Ala Glu Glu Glu Ala Ala Lys Glu Leu Pro His Ala Phe Ile Gly
            1205                1210                1215

Asp Val Lys Gly Thr Thr Val Gly Gly Cys His His Ile Thr Ser Lys
            1220                1225                1230

Tyr Leu Pro Arg Ser Leu Pro Lys Asp Ser Ile Ala Val Val Gly Val
            1235                1240                1245

Ser Ser Pro Gly Arg Ala Ala Lys Ala Met Cys Thr Leu Thr Asp Val
            1250                1255                1260

Tyr Leu Pro Glu Leu Arg Pro Tyr Leu Gln Pro Glu Thr Ala Ser Lys
1265                1270                1275                1280

Cys Trp Lys Leu Lys Leu Asp Phe Arg Asp Val Arg Leu Met Val Trp
            1285                1290                1295

Lys Gly Ala Thr Ala Tyr Phe Gln Leu Glu Gly Phe Thr Trp Ser Ala
            1300                1305                1310

Leu Pro Asp Tyr Ala Arg Phe Ile Gln Leu Pro Lys Asp Ala Val Val
```

```
                    1315                1320                1325
Tyr Ile Asp Pro Cys Ile Gly Pro Ala Thr Ala Asn Arg Lys Val Val
    1330                1335                1340

Arg Thr Thr Asp Trp Arg Ala Asp Leu Ala Val Thr Pro Tyr Asp Tyr
1345                1350                1355                1360

Gly Ala Gln Asn Ile Leu Thr Thr Ala Trp Phe Glu Asp Leu Gly Pro
                1365                1370                1375

Gln Trp Lys Ile Leu Gly Leu Gln Pro Phe Arg Arg Ala Phe Gly Leu
            1380                1385                1390

Glu Asn Thr Glu Asp Trp Ala Ile Leu Ala Arg Arg Met Asn Asp Gly
        1395                1400                1405

Lys Asp Tyr Thr Asp Tyr Asn Trp Asn Cys Val Arg Glu Arg Ser His
    1410                1415                1420

Ala Ile Tyr Gly Arg Ala Arg Asp His Thr Tyr His Phe Ala Pro Gly
1425                1430                1435                1440

Thr Glu Leu Gln Val Glu Leu Gly Lys Pro Arg Leu Pro Pro Gly Gln
                1445                1450                1455

Val Pro

<210> SEQ ID NO 4
<211> LENGTH: 249
<212> TYPE: PRT
<213> ORGANISM: Porcine reproductive and respiratory syndrome virus

<400> SEQUENCE: 4

Met Gln Trp Gly His Cys Gly Val Arg Ser Ala Ser Cys Ser Trp Thr
  1               5                  10                  15

Pro Ser Leu Ser Ser Leu Leu Val Trp Leu Ile Leu Ser Phe Phe Leu
                 20                  25                  30

Pro Tyr Cys Leu Gly Ser Pro Ser Gln Asp Gly Tyr Trp Ser Phe Phe
             35                  40                  45

Ser Glu Trp Phe Ala Pro Arg Phe Ser Val Arg Ala Leu Pro Phe Thr
         50                  55                  60

Leu Pro Asn Tyr Arg Arg Ser Tyr Glu Gly Leu Leu Pro Asn Cys Arg
 65                  70                  75                  80

Pro Asp Val Pro Gln Phe Ala Val Lys His Pro Leu Gly Met Phe Trp
                 85                  90                  95

His Met Arg Val Ser His Leu Ile Asp Glu Met Val Ser Arg Arg Ile
            100                 105                 110

Tyr Gln Thr Met Glu His Ser Gly Gln Ala Ala Trp Lys His Val Val
        115                 120                 125

Gly Glu Ala Thr Leu Thr Lys Leu Ser Gly Leu Asp Ile Val Thr His
    130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asn Arg Val Glu Leu Ile Phe Pro Thr Pro
            180                 185                 190

Gly Thr Arg Pro Lys Leu Thr Asp Phe Arg Gln Trp Leu Ile Ser Val
        195                 200                 205

His Ala Ser Ile Phe Ser Ser Val Ala Ser Ser Val Thr Leu Phe Thr
    210                 215                 220

Val Leu Trp Leu Arg Ile Pro Ala Leu Arg Tyr Val Phe Gly Phe His
```

```
                225                 230                 235                 240

Trp Pro Thr Ala Thr His His Ser Ser
                245

<210> SEQ ID NO 5
<211> LENGTH: 265
<212> TYPE: PRT
<213> ORGANISM: Porcine reproductive and respiratory syndrome virus

<400> SEQUENCE: 5

Met Ala His Gln Cys Ala Arg Phe His Phe Leu Cys Gly Phe Ile
  1               5                  10                  15

Cys Tyr Phe Val His Ser Ala Leu Ala Ser Asn Ser Ser Thr Leu
                 20                  25                  30

Cys Phe Trp Phe Pro Leu Ala His Gly Asn Thr Ser Phe Glu Leu Thr
             35                  40                  45

Ile Asn Tyr Thr Val Cys Met Pro Cys Pro Thr Ser Gln Ala Ala Leu
 50                  55                  60

Gln Arg Leu Glu Pro Gly Arg Asn Met Trp Cys Lys Ile Gly His Asp
 65                  70                  75                  80

Arg Cys Glu Glu Arg Asp Gln Asp Glu Leu Leu Met Ser Ile Pro Ser
                 85                  90                  95

Gly Tyr Asp Asn Leu Lys Leu Glu Gly Tyr Tyr Ala Trp Leu Ala Phe
            100                 105                 110

Leu Ser Phe Ser Tyr Ala Ala Gln Phe His Pro Glu Leu Phe Gly Ile
        115                 120                 125

Gly Asn Val Ser Arg Val Phe Val Asp Lys Trp His Gln Phe Ile Cys
    130                 135                 140

Ala Glu His Asp Gly Ser Asn Ser Thr Val Ser Thr Gly His Asn Ile
145                 150                 155                 160

Ser Ala Leu Tyr Ala Ala Tyr Tyr His His Gln Ile Asp Gly Gly Asn
                165                 170                 175

Trp Phe His Leu Glu Trp Leu Arg Pro Phe Phe Ser Ser Trp Leu Val
            180                 185                 190

Leu Asn Ile Ser Trp Phe Leu Arg Arg Ser Pro Val Ser Pro Val Ser
        195                 200                 205

Arg Arg Ile Tyr Gln Ile Leu Arg Pro Thr Arg Pro Gln Leu Pro Val
    210                 215                 220

Ser Trp Ser Phe Arg Thr Ser Ile Val Ser Asp Leu Met Arg Ser Gln
225                 230                 235                 240

Gln Arg Lys Gly Lys Phe Pro Ser Gly Ser Arg Pro Asn Ala Val Lys
                245                 250                 255

Pro Ser Ala Leu Pro Asn Ile Ser Arg
            260                 265

<210> SEQ ID NO 6
<211> LENGTH: 183
<212> TYPE: PRT
<213> ORGANISM: Porcine reproductive and respiratory syndrome virus

<400> SEQUENCE: 6

Met Ala Ala Ala Ile Leu Phe Leu Leu Ala Gly Ala Gln His Ile Met
  1               5                  10                  15

Val Ser Glu Ala Phe Ala Cys Lys Pro Cys Phe Ser Thr His Leu Ser
                 20                  25                  30

Asp Ile Lys Thr Asn Thr Thr Ala Ala Ala Gly Phe Met Val Leu Gln
```

```
                 35                  40                  45
Asp Ile Asn Cys Phe Arg Pro His Glu Val Ser Ala Thr Gln Arg Glu
 50                  55                  60

Ile Pro Phe Arg Lys Ser Ser Gln Cys Arg Glu Ala Val Gly Thr Pro
 65                  70                  75                  80

Gln Tyr Ile Thr Ile Thr Ala Asn Val Thr Asp Glu Ser Tyr Leu Tyr
                 85                  90                  95

Asn Ala Asp Leu Leu Met Leu Ser Ala Cys Leu Phe Tyr Ala Ser Glu
                100                 105                 110

Met Ser Glu Lys Gly Phe Lys Val Ile Phe Gly Asn Val Ser Gly Val
            115                 120                 125

Val Ser Ala Cys Val Asn Phe Thr Asp Tyr Val Ala His Val Thr Gln
130                 135                 140

His Thr Gln Gln His His Leu Val Ile Asp His Ile Arg Leu Leu His
145                 150                 155                 160

Phe Leu Thr Pro Ser Thr Met Arg Trp Ala Thr Thr Ile Ala Cys Leu
                165                 170                 175

Phe Ala Ile Leu Leu Ala Ile
            180

<210> SEQ ID NO 7
<211> LENGTH: 201
<212> TYPE: PRT
<213> ORGANISM: Porcine reproductive and respiratory syndrome virus

<400> SEQUENCE: 7

Met Arg Cys Ser Tyr Lys Leu Gly Arg Ser Leu Ile Leu His Ser Cys
  1               5                  10                  15

Ser Trp Trp Phe Phe Leu Leu Cys Thr Gly Leu Ser Trp Ser Phe Ala
                 20                  25                  30

Asp Gly Asn Gly Asn Ser Thr Tyr Gln Tyr Ile Tyr Asn Leu Thr
                 35                  40                  45

Ile Cys Glu Leu Asn Gly Thr Asn Trp Leu Ser Gly His Phe Asp Trp
 50                  55                  60

Ala Val Glu Thr Phe Val Leu Tyr Pro Val Val Thr His Ile Leu Ser
 65                  70                  75                  80

Leu Gly Phe Leu Thr Thr Ser His Phe Phe Asp Ala Leu Gly Leu Gly
                 85                  90                  95

Ala Val Ser Thr Ala Gly Phe Ile Asp Gly Arg Tyr Val Leu Ser Ser
                100                 105                 110

Ile Tyr Gly Ala Cys Ala Phe Ala Ala Phe Val Cys Phe Val Ile Arg
            115                 120                 125

Ala Ala Lys Asn Cys Met Ala Cys Arg Tyr Ala Arg Thr Arg Phe Thr
130                 135                 140

Asn Phe Ile Val Asp Asp Arg Gly Gly Val His Arg Trp Lys Ser Pro
145                 150                 155                 160

Ile Val Val Glu Lys Leu Gly Lys Ala Asp Ile Asp Gly Ser Leu Val
                165                 170                 175

Thr Ile Lys His Val Val Leu Glu Gly Val Lys Ala Gln Pro Leu Thr
            180                 185                 190

Arg Thr Ser Ala Glu Gln Trp Glu Ala
            195                 200

<210> SEQ ID NO 8
<211> LENGTH: 108
```

```
<212> TYPE: PRT
<213> ORGANISM: Porcine reproductive and respiratory syndrome virus

<400> SEQUENCE: 8

Met Gly Pro Ile Gly Phe Pro Ala Ile Leu Ile Gly Gln Leu Arg Pro
 1               5                  10                  15

Leu Cys Phe Thr Arg Ser Ser Leu Ile Ser Ser His Trp Val Phe Ser
                20                  25                  30

Arg Gln Val Ile Phe Leu Thr Arg Ser Val Ser Ala Leu Cys Pro Pro
            35                  40                  45

Gln Asp Leu Leu Thr Gly Gly Met Cys Ser Ala Ser Thr Ala Leu
        50                  55                  60

Val Leu Ser Gln Arg Ser Tyr Val Leu Ser Ser Val Leu Lys Ile
 65                 70                  75                  80

Ala Trp Pro Ala Val Thr Pro Val Pro Gly Leu Pro Thr Leu Leu Trp
                85                  90                  95

Thr Thr Gly Glu Glu Phe Ile Gly Gly Ser Leu Gln
            100                 105

<210> SEQ ID NO 9
<211> LENGTH: 173
<212> TYPE: PRT
<213> ORGANISM: Porcine reproductive and respiratory syndrome virus

<400> SEQUENCE: 9

Met Gly Gly Leu Asp Asp Phe Cys Asn Asp Pro Thr Ala Ala Gln Lys
 1               5                  10                  15

Leu Val Leu Ala Phe Ser Ile Thr Tyr Thr Pro Ile Met Ile Tyr Ala
                20                  25                  30

Leu Lys Val Ser Arg Gly Arg Leu Leu Gly Leu Leu His Ile Leu Ile
            35                  40                  45

Phe Leu Asn Cys Ser Phe Thr Phe Gly Tyr Met Thr Tyr Val His Phe
        50                  55                  60

Gln Ser Ala Asn Arg Val Ala Leu Thr Leu Gly Ala Val Val Ala Leu
 65                 70                  75                  80

Leu Trp Gly Val Tyr Ser Leu Thr Glu Ser Trp Lys Phe Ile Thr Ser
                85                  90                  95

Arg Cys Arg Leu Cys Cys Leu Gly Arg Arg Tyr Ile Leu Ala Pro Ala
            100                 105                 110

His His Val Glu Ser Ala Ala Gly Leu His Ser Ile Ser Ala Ser Gly
        115                 120                 125

Asn Arg Ala Tyr Ala Val Arg Lys Pro Gly Leu Thr Ser Val Asn Gly
130                 135                 140

Thr Leu Val Pro Gly Leu Arg Ser Leu Val Leu Gly Gly Lys Arg Ala
145                 150                 155                 160

Val Lys Arg Gly Val Val Asn Leu Val Lys Tyr Gly Arg
                165                 170

<210> SEQ ID NO 10
<211> LENGTH: 128
<212> TYPE: PRT
<213> ORGANISM: Porcine reproductive and respiratory syndrome virus

<400> SEQUENCE: 10

Met Ala Gly Lys Asn Gln Ser Gln Lys Lys Lys Lys Ser Thr Ala Pro
 1               5                  10                  15

Met Gly Asn Gly Gln Pro Val Asn Gln Leu Cys Gln Leu Leu Gly Ala
```

```
            20                  25                  30
Met Ile Lys Ser Gln Arg Gln Gln Pro Arg Gly Gly Gln Ala Lys Lys
         35                  40                  45

Lys Lys Pro Glu Lys Pro His Phe Pro Leu Ala Ala Glu Asp Asp Ile
     50                  55                  60

Arg His His Leu Thr Gln Thr Glu Arg Ser Leu Cys Leu Gln Ser Ile
 65                  70                  75                  80

Gln Thr Ala Phe Asn Gln Gly Ala Gly Thr Ala Ser Leu Ser Ser Ser
                 85                  90                  95

Gly Lys Val Ser Phe Gln Val Glu Phe Met Leu Pro Val Gly His Thr
            100                 105                 110

Val Arg Leu Ile Arg Val Thr Ser Thr Ser Ala Ser Gln Gly Ala Ser
        115                 120                 125

<210> SEQ ID NO 11
<211> LENGTH: 840
<212> TYPE: DNA
<213> ORGANISM: Porcine reproductive and respiratory syndrome virus

<400> SEQUENCE: 11
tctctagttt gtataaatta ctattagagg ttgttccgca aaaatgcggt gccacggaag    60
gggctttcat ctatgctgtt gagaggatgt tgaaggattg tccgagctcc aaacaggcca   120
tggcccttct ggcaaaaatt aaagttccat cctcaaaggc cccgtctgtg tccctggacg   180
agtgtttccc tacggatgtt ttagccgact tcgagccagc atctcaggaa aggccccaaa   240
gttccggcgc tgctgttgtc ctgtgttcac cggatgcaaa agagttcgag aagcagccc    300 cggaagaagt tcaagagagt ggccacaagg ccgtccactc tgcactcctt gccgagggtc   360
ctaacaatga gcaggtacag gtggttgccg gtgagcaact gaagctcggc ggttgtggtt   420
tggcagtcgg gaatgctcat gaaggtgctc tggtctcagc tggtctaatt aacctggtag   480
gcgggaattt gtccccctca gaccccatga agaaaacat gctcaatagc cgggaagacg    540
aaccactgga tttgtcccaa ccagcaccag cttccacaac gacccttgtg agagagcaaa   600
cacccgacaa cccaggttct gatgccggtg ccctccccgt caccgttcga gaatttgtcc   660
cgacggggcc tatactctgt catgttgagc actgcggcac ggagtcgggc gacagcagtt   720
cgcctttgga tctatctgat gcgcaaaccc tggaccagcc tttaaatcta tccctggccg   780
cttggccagt gagggccacc gcgtctgacc ctggctgggt ccacggtagg cgcgagcctg   840

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 12
atcgggaatg ctcagtcccc tt                                             22

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 13
gcgcataaga cagatcca                                                  18
```

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 14
aaggggactg agcattcccg                                              20

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 15
cagaagggtt cgaggaag                                                18

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 16
gcctgtccta acgccaagta c                                            21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 17
catgtccacc ctatcccaca t                                            21

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence:
          oligonucleotide

<400> SEQUENCE: 18
agagcgggaa cagaatcctt cccaccttta gcggtacgct tg                     42

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence:primer

<400> SEQUENCE: 19
gcttggaact gcgagg                                                  16

<210> SEQ ID NO 20
<211> LENGTH: 17
<212> TYPE: DNA
<213> ORGANISM: Artificial Sequence -continued

```
<220> FEATURE:
<223> OTHER INFORMATION: Description of Artificial Sequence:primer

<400> SEQUENCE: 20
tgaaggtgct ctggtct                                                   17

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence:primer

<400> SEQUENCE: 21
aaattcccgc ctacc                                                     15
```

PORCINE REPRODUCTIVE AND RESPIRATORY SYNDROME VIRUS AND METHODS OF USE

CONTINUING APPLICATION DATA

This application claims the benefit of the following U.S. Provisional Applications: Ser. No. 60/181,041, filed Feb. 8, 2000; Ser. No. 60/193,220, filed Mar. 30, 2000; Ser. No. 60/206,624, filed May 24. 2000; Ser. No. 60/215,373, filed Jun. 29, 2000; and Ser. No. 60/260,041, filed Jan. 5, 2001, entitled PORCINE REPRODUCTIVE AND RESPIRATORY SYNDROME VIRUS AND METHOD OF DETECTION; each of which is incorporated by reference herein.

BACKGROUND

Porcine reproductive and respiratory syndrome virus (PRRSV) is a member of the family *Arteriviridae* in the order *Nidovirales* (Cavanagh et al., *Virol.*, 176, 306–307 (1990)) that causes reproductive failure in breeding swine and respiratory problems in young pigs (see Rossow, *Vet. Pathol.*, 35, 1–20 (1998)). The syndrome was first recognized as a "mystery swine disease" in the United States in 1987 and was discovered in Europe in 1990. A strain of PRRSV that is prevalent in Europe has been isolated and is referred to as the Lelystad virus (Wensvoort et al., *Vet. Q.*, 13, 121–130(1991)). A North American PRRSV, referred to as VR-2332, has been isolated (Collins et al., *J. Vet. Diagn. Investig.*, 4, 117–126 (1992)). The disease has also been referred to as Wabash syndrome, mystery pig disease, porcine reproductive and respiratory syndrome, swine plague, porcine epidemic abortion and respiratory syndrome, blue abortion disease, blue ear disease, abortus blau, and seuchenhafter spatabort der schweine. The disease is characterized by reproductive failure in pregnant sows and respiratory problems in pigs of all ages. The disease has a significant negative impact on the swine industry.

PRRSV is an enveloped positive single-stranded RNA virus. The 5'-capped and 3'-polyadenylated RNA of the virus is polycistronic, containing (5' to 3') two large replicase open reading frames (ORFs), 1a and 1b, and several smaller ORFs. In the infected cell, arteriviruses produce a nested set of six to eight major coterminal subgenomic mRNAs (sgm-RNAs) each thought to express only the relative 5'-terminal ORF. These sgmRNAs have a leader sequence derived from the 5' end of the genome that is joined at specific leader-body junction sites located downstream by an unclear discontinuous transcription mechanism (Lai, *Adv. Exp. Med. Biol.*, 380, 463–471 (1995)). The sgmRNAs of PRRSV encode four glycoproteins (GP2 to 5, encoded by sgmRNAs 2 to 5), an unglycosylated membrane protein (M, encoded by sgmRNA 6), and a nucleocapsid protein (N, encoded by sgmRNA 7). The European prototype strain of PRRSV, Lelystad, contains all six of these proteins in the virus particle, but only the proteins encoded by ORFs 5 to 7 have conclusively been demonstrated to be in the virion of North American isolates.

Nucleotide and amino acid sequence comparisons of the 3'-terminal ORFs 2 to 7 have shown that there are significant differences between PRRSV strains native to Europe and those found in North America (Kapur et al., *J. Gen. Virol.*, 77, 1271–1276 (1996), Murtaugh et al., *Arch. Virol.*, 40, 1451–1460 (1995)). Substantial variation also occurs among North American PRRSV isolates. Genotypic comparison between strains VR-2332 and Lelystad has revealed that ORF 1a of VR-2332 is vastly different from that of Lelystad in both length and sequence, while ORF 1b is relatively conserved between the two strains of PRRSV. The 5' leader sequence of VR-2332 was 31 bases shorter than that of Lelystad and differed considerably in nucleotide sequence. Regional amino acid sequence comparisons also revealed that although the recognized functional domains of the ORF 1a proteins were present in both strains, the proteins were not well conserved between these domains. Thus, although these two PRRSV strains cause similar diseases, they are different in the genes encoding structural proteins.

PRRSV continues to cause significant economic losses throughout the world. Vaccines are available, but they are based on one PRRSV strain, and there is evidence that PRRSV strains vary at the antigenic and genetic levels. In addition, since the virus was identified in Europe and in the United States, new disease phenotypes have continued to emerge.

SUMMARY OF THE INVENTION

The present invention represents the identification of a novel porcine reproductive and respiratory syndrome virus (PRRSV). It is known to the art that there is a great deal of nucleotide sequence variation between European PRRSV associated with European outbreaks of mystery swine disease (MSD) and North American PRRSV associated with North American outbreaks of MSD. As used herein the terms "European PRRSV" and "European strain" are used interchangeably and refer to strains of PRRSV that are prevalent in Europe. An example of a "European PRRSV" that is known to the art is the prototypic European strain, Lelystad, which is available from the Collection Nationale De Cultures De Microorganisms, Institut Pasteur, France, as deposit number I-1102 (see Wensvoort et al., U.S. Pat. No. 5,620, 691). The nucleotide sequence of the Lelystad strain is available at Genbank Accession Number NC_002533. As used herein the terms "North American PRRSV" and "North American strain" are used interchangeably and refer to strains of the PRRSV that are prevalent in North America. An example of a "North American PRRSV" that is known to the art is the prototypic North American strain, VR-2332, which is available from the ATCC as deposit number VR-2332. The nucleotide sequence of the VR-2332 strain is available at Genbank Accession Number U87392.

The PRRSV described herein has not been described before, and was associated with a North American outbreak of MSD, but unexpectedly and surprisingly has a nucleotide sequence that has more similarity to European PRRSV strains, than to North American PRRSV strains. As used herein the phrase "European-like PRRSV" and "European-like strain" are used interchangeably and refer to PRRSV of the present invention. The characteristics of European-like PRRSV are described herein.

The present invention provides an isolated virus deposited under ATCC Accession Number PTA-2194, and an isolated cell comprising the virus. Also provided by the invention is an isolated virus that includes an RNA polynucleotide that includes the RNA nucleotide sequence corresponding to SEQ ID NO: 1. The invention provides an isolated polynucleotide that includes the sequence SEQ ID NO: 1. The isolated polynucleotide can have at least about 96% identity with a polynucleotide having the sequence shown in SEQ ID NO: 1 using a GAP algorithm with default parameters, wherein the polynucleotide replicates in a cell.

Also provided is a vector that includes a polynucleotide that includes the sequence shown in SEQ ID NO: 1, and a polypeptide that includes an amino acid sequence selected from the group consisting of SEQ ID NO:2–10. The invention provides polypeptides that have an amino acid sequence having at least about 95% identity to SEQ ID NO:2, at least about 99% identity to SEQ ID NO:3, at least about 98% identity to SEQ ID NO:4, at least about 94% identity to SEQ ID NO:5, at least about 95% identity to SEQ ID NO:6, at least about 91% identity to SEQ ID NO:7, at least about 99% identity to SEQ ID NO:9, or at least about 99.5% identity to SEQ ID NO: 10.

The invention provides an antibody that specifically binds a European-like porcine reproductive and respiratory syndrome virus (PRRSV), and a method of making an antibody. The method includes administering to an animal a virus particle that includes an RNA polynucleotide that includes the RNA nucleotide sequence corresponding to SEQ ID NO: 1, or a polypeptide that includes an amino acid sequence selected from the group consisting of SEQ ID NO:2–10, or a polynucleotide encoding the polypeptide. The particle, polypeptide, or polynucleotide is administered in an amount effective to cause the production of an antibody specific for the virus particle. The antibody can be a polyclonal antibody or a monoclonal antibody, and the method can further include isolating the antibody. Also provided is the antibody produced by the method.

Methods for detecting a PRRSV are also provided. A method includes contacting a virus particle, for instance from a biological sample, with an antibody of the present invention under conditions to form a complex with a virus particle, and detecting the complex, wherein the presence of the complex indicates the presence of a PRRSV. The method can also be used to detect PRRSV in a porcine subject. Also provided is a kit for use in detecting PRRSV in a porcine subject. The kit includes the antibody of the invention and instructions for using the antibody.

Methods for detecting the presence of a European-like PRRSV are also provided. The methods include contacting a viral polynucleotide with a first primer and a second primer under conditions suitable to form a detectable amplification product. The first primer includes a nucleotide sequence that is complementary to nucleotides 2268 and 2269 of SEQ ID NO:1 or the complement thereof. The method further includes detecting an amplification product, wherein the detection indicates that the viral polynucleotide is a European-like PRRSV. Examples of first primers that can be used include 5'ATCGGGAATGCTCAGTCCCCTT (SEQ ID NO:12), and 5'-AAGGGGACTGAGCATTCCCG (SEQ ID NO:14). The method can also be used for detecting the presence of a European-like PRRSV in a porcine subject, and includes contacting a biological sample of a porcine subject with the first primer and the second primer. The biological sample preferably includes lung tissue.

Also provided by the invention is a kit for use in detecting PRRSV in a porcine subject. The kit includes the first primers and second primers of the invention suitable for use in amplification of a portion of a PRRSV and instructions for using the primer pair. Another kit provided by the invention is for use in detecting antibody to PRRSV in a porcine subject. The kit includes the virus of the invention and instructions for using the virus.

Further provided by the invention is an immunogenic composition. The composition includes an attenuated or inactivated PRRSV that includes a polynucleotide having at least about 96% identity with a polynucleotide having the sequence shown in SEQ ID NO: 1 using a GAP algorithm with default parameters. The immunogenic composition may include a polypeptide selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, an immunogenic analog thereof, an immunogenic fragment thereof, or a combination thereof.

Methods of treating a porcine subject at risk of infection with a PRRSV or displaying symptoms of a PRRSV infection are also provided. The methods include administering to the animal an immunogenic composition that includes an attenuated or inactivated PRRSV that includes a polynucleotide having at least about 96% identity with comprising an RNA polynucleotide comprising the RNA nucleotide sequence corresponding to SEQ ID NO: 1 using a GAP algorithm with default parameters. The immunogenic composition is administered in an amount effective to cause an immune response to the PRRSV. The immunogenic composition can include a polypeptide selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, an immunogenic analog thereof, an immunogenic fragment thereof, or a combination thereof. Alternatively, the porcine subject can be administered a neutralizing antibody in an amount effective to treat the porcine subject.

Unless otherwise specified, "a," "an," "the," and "at least one" are used interchangeably and mean one or more than one.

BRIEF DESCRIPTION OF THE FIGURES

FIG. 1. DNA nucleotide sequence of a portion of the positive strand of the genome of the European-like strain (SEQ ID NO: 1). The RNA sequence that corresponds to SEQ ID NO: 1 and is present in a viral particle has uracil (U) nucleotides instead of the thymidine (T) residues. Rows 1, 2, and 3 under the nucleotide sequence represent the three different reading frames. The predicted amino acid sequences encoded by the European-like strain are depicted for some predicted open reading frames, including: SEQ ID NO:2 (ORF1 a), SEQ ID NO:3 (ORF1b), SEQ ID NO:4 (ORF2), SEQ ID NO:5 (ORF3), SEQ ID NO:6 (OFR4), SEQ ID NO:7 (ORF5), SEQ ID NO:8, SEQ ID NO:9 (ORF6), and SEQ ID NO: 10 (ORF7).

FIG. 2. DNA nucleotide sequence of a portion of the positive strand of the genome of the European-like strain (nucleotides 1,830 to 2,618 of SEQ ID NO: 1) compared to a portion of the DNA nucleotide sequence of the prototypic European strain Lelystad (SEQ ID NO 11, which corresponds to nucleotides 1,981 to 2,820 of Genbank Accession Number NC_002533). In SEQ ID NO: 11, the upper case nucleotides signify aligned non-identical nucleotides; lower case nucleotides signify unaligned nucleotides; dashes signify aligned identical nucleotides; and dots signify a gap.

DETAILED DESCRIPTION OF THE INVENTION

Polynucleotides

Figure 1S:
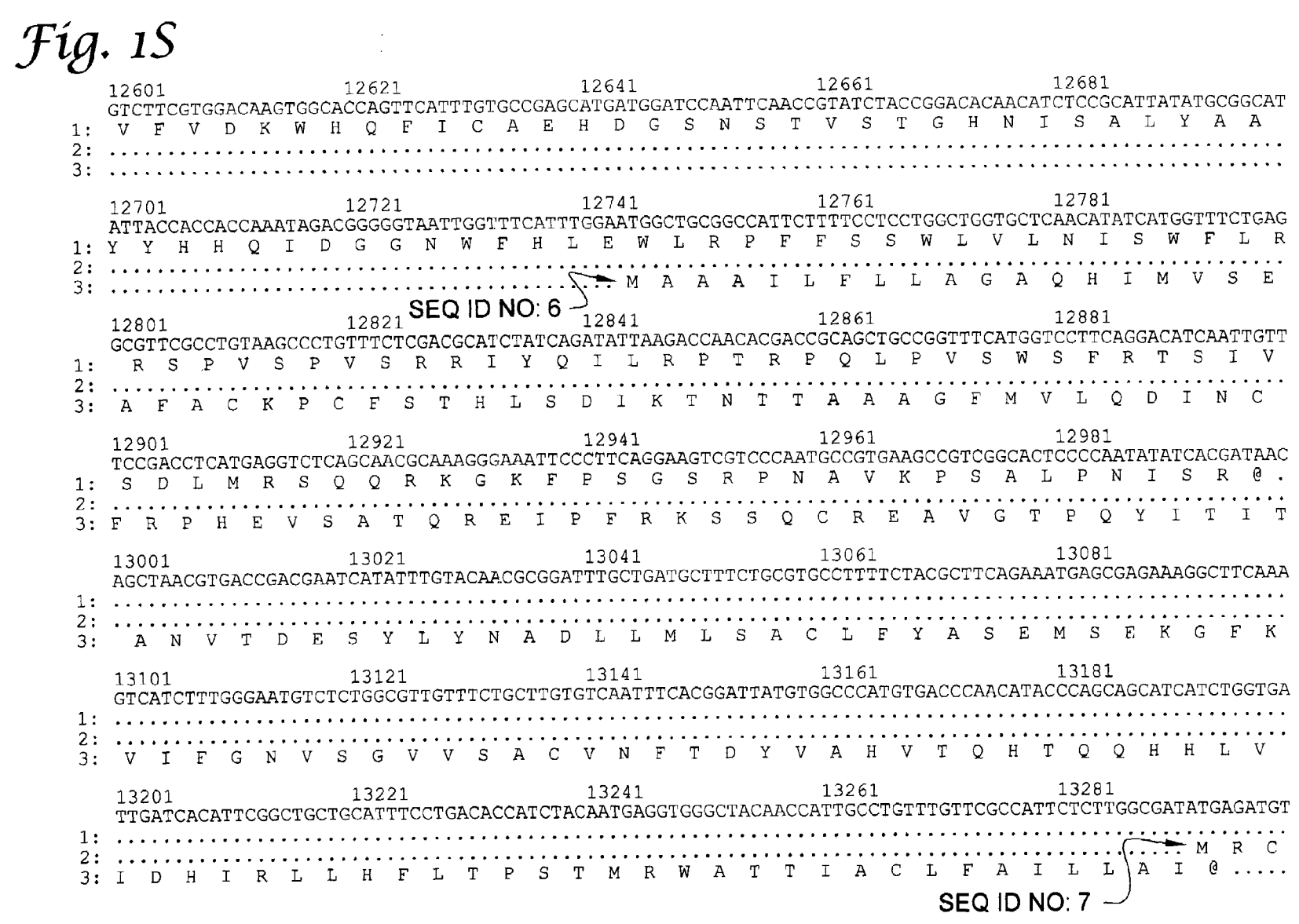

The present invention is based on the the identification of a novel porcine reproductive and respiratory syndrome virus (PRRSV), an enveloped positive single-stranded RNA virus. Accordingly, the present invention provides isolated polynucleotides. Preferably, an isolated polynucleotide can replicate in a cell. Preferably, an isolated polynucleotide of the present invention is no greater than about 15.3 kilobases. Whether an isolated polynucleotide can replicate in a cell can be determined by inserting the polynucleotide into an expression vector, producing an infectious RNA, introducing the infectious RNA to a cells, and evaluating if the infectious RNA causes the cell to produce virus particles. These methods are described in greater detail herein. A preferred example of a polynucleotide of the present invention is SEQ ID NO: 1 (FIG. 1). This polypeptide is a portion of a polynucleotide obtained from a European-like PRRSV. Preferably, the European-like PRRSV is one having the strain designation MND99-35186, and deposited with the American Type Culture Collection, 10801 University Blvd., Manassas, Va., 20110-2209, USA, on Jul. 7, 2000 (granted ATCC Accession Number PTA-2194).

The deposit was made under the Budapest Treaty on the International Recognition of the Deposit of Microorganisms for the Purposes of Patent Procedure. It is expected that the complete nucleotide sequence of the PRRSV disclosed in SEQ ID NO: 1 will include additional nucleotides at the 5' end of the polynucleotide. Specifically, it is expected that about 100 to about 200, preferably about 150, additional nucleotides can be present at the 5' end of SEQ ID NO: 1 when the nucleotide sequence of the entire PRRSV represented by SEQ ID NO: 1 is determined. It should be noted that while SEQ ID NO: 1 is a DNA sequence, the present invention contemplates the corresponding RNA sequence, and RNA and DNA complements thereof, as well.

As used herein, an "isolated" substance is one that has been removed from its natural environment, produced using recombinant techniques, or chemically or enzymatically synthesized. For instance, a polypeptide, polynucleotide, or virus particle of this invention can be isolated. Preferably, a polypeptide, polynucleotide, or virus particle of this invention is purified, i.e., essentially free from any other type of polypeptide, polynucleotide, or virus particle and associated cellular products or other impurities. As used herein, the term "polynucleotide" refers to a polymeric form of nucleotides of any length, either ribonucleotides or deoxynucleotides, and includes both double- and single-stranded DNA and RNA. Unless otherwise noted, a polynucleotide includes the complement thereof. The nucleotide sequence of the complement of a polynucleotide can be easily determined by a person of skill in the art. A polynucleotide may include nucleotide sequences having different functions, including for instance coding sequences, and non-coding sequences such as regulatory sequences and/or non-translated regions. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations and the like.

The terms "coding region" and "coding sequence" are used interchangeably and refer to a polynucleotide region that encodes a polypeptide and, when placed under the control of appropriate regulatory sequences, expresses the encoded polypeptide. The boundaries of a coding region are generally determined by a translation start codon at its 5' end and a translation stop codon at its 3' end. A regulatory sequence is a polynucleotide sequence that regulates expression of a coding region to which it is operably linked. Nonlimiting examples of regulatory sequences include promoters, transcription initiation sites, translation start sites, translation stop sites, and terminators. "Operably linked" refers to a juxtaposition wherein the components so described are in a relationship permitting them to function in their intended manner. A regulatory sequence is "operably linked" to a coding region when it is joined in such a way that expression of the coding region is achieved under conditions compatible with the regulatory sequence.

"Complement" and "complementary" refer to the ability of two single stranded polynucleotides to base pair, i.e., hybridize, with each other, where an adenine of one polynucleotide will base pair to a thymine of a second polynucleotide and a cytosine of one polynucleotide will base pair to a guanine of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary. The terms complement and complementary also encompass two polynucleotides where one polynucleotide contains at least one nucleotide that will not base pair to at least one nucleotide present on a second polynucleotide under the hybridization conditions described below. For instance the third nucleotide of each of the two polynucleotides 5'-ATTGC and 5'-GCTAT will not base pair, but these two polynucleotides are complementary as defined herein.

The present invention also provides isolated polynucleotides that correspond to the coding regions present in SEQ ID NO:1. These coding regions are shown in Table 1.

TABLE 1

Coding regions of SEQ ID NO: 1

| Nucleotides of SEQ ID NO: 1 corresponding to the coding region. | Polypeptide encoded by the coding region. | SEQ ID NO of the polypeptide. |
| --- | --- | --- |
| 71 to 7,210 | ORF1a | SEQ ID NO: 2 |
| 7,207 to 11,583 | ORF1b | SEQ ID NO: 3 |
| 11,594 to 12,343 | ORF2 | SEQ ID NO: 4 |
| 12,202 to 12,994 | ORF3 | SEQ ID NO: 5 |
| 12,744 to 13,295 | ORF4 | SEQ ID NO: 6 |
| 13,292 to 13,897 | ORF5 | SEQ ID NO: 7 |
| 13,449 to 13,775 | not applicable | SEQ ID NO: 8 |
| 13,885 to 14,406 | ORF6 | SEQ ID NO: 9 |
| 14,396 to 14,782 | ORF7 | SEQ ID NO: 10 |

The present invention also includes polynucleotides having structural similarity to SEQ ID NO:1 or to a coding region present in SEQ ID NO:1. The similarity is referred to as "percent identity" and is determined by aligning the residues of the two polynucleotides (i.e., the nucleotide sequence of a candidate polynucleotide and the nucleotide sequence of SEQ ID NO:1 or a coding region of SEQ ID NO: 1) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate polynucleotide is the polynucleotide that has the nucleotide sequence being compared to SEQ ID NO:1 or to a coding region present in SEQ ID NO: 1 (e.g., nucleotides 71 to 7,210 of SEQ ID NO:1). A candidate polynucleotide can be isolated from an animal, preferably a pig infected with PRRSV, or can be produced using recombinant techniques, or chemically or enzymatically synthesized. Preferably, two nucleotide sequences are compared using the GAP program of the GCG Wisconsin Package (Genetics Computer Group, Madison, Wis.) version 10.0 (update January 1999). The GAP program uses the algorithm of Needleman and Wunsch (*J. Mol. Biol.*, 48, 443–453 (1970)) to find the alignment of two complete sequences that maximizes the number of matches and minimizes the number of gaps. Preferably, the default values for all GAP search parameters are used, including scoring matrix=NewsgapDNA.cmp, gap weight=50, length weight=3, average match=10, average mismatch=0. In the comparison of two nucleotide sequences using the GAP search algorithm, structural similarity is referred to as "percent identity." Preferably, a polynucleotide includes a nucleotide sequence having a structural similarity with a coding region of SEQ ID NO:1 of at least about 96%, more preferably at least about 98%, most preferably at least about 99% identity.

Another isolated polynucleotide provided by the invention is an RNA polynucleotide to which an oligonucleotide having the sequence AGAGCGGGAACAGAATCCTTC-CCACCTTTAGCGGTACGCTTG (SEQ ID NO:18) hybridizes. Preferably, the RNA polynucleotide replicates in cells to form virus particles. Such an RNA is referred to as an infectious RNA. The production and testing of infectious RNAs are described in greater detail below. Preferably, hybridization conditions include denaturing about 1 μg total RNA with glyoxyl and electrophoresing through a 2% agarose gel, transferring to a nylon membrane (Magna-Graph, MSI, Westboro, Mass.), and crosslinking to the membrane by ultraviolet light. Preferably, the oligonucleotide is 3-end radiolabeled, for instance with [α$^{32}$P]dATP (Amersham Life Science, Arlington Heights, Ill.) and terminal deoxynucleotide transferase (TdT) (Promega Corporation, Madison, Wis.). Preferably, hybridization conditions include incubation of the membrane containing the crosslinked RNA with the labeled oligonucleotide in a hybridization solution, for instance QuikHyb (Stratagene, La Jolla, Calif.) at 68° C. for 16 hours. The membrane is then washed 3 times in a solution containing 0.9 M sodium chloride/0.09 M sodium citrate/pH 7.0 (6×SSC) and 0.5% sodium dodecyl sulfate (SDS) at 78° C., and then exposed to autoradiography film (NEN Life Science Products, Boston, Mass.) or a phosphoimaging screen (Molecular Dynamics, Inc., Sunnyvale, Calif.). It is expected that under these conditions, the oligonucleotide will not hybridize to the European PRRSV Lelystad or to the North American PRRSV VR-2332.

Preferably, a polynucleotide of the present invention includes a deletion when compared to the nucleotide sequence of European strain Lelystad, which is available at Genbank Accession Number NC_002533. When the nucleotide sequence of SEQ ID NO:1 and Genbank Accession Number NC_002533 are compared, nucleotides 2,419 to 2,470 of Genbank Accession Number NC_002533 are not present in SEQ ID NO: 1. Nucleotides 2268 and 2269 of SEQ ID NO: 1 are immediately 5' (upstream) and 3' (downstream) of this deletion. Thus, those polynucleotides of the present invention that include nucleotides 2268 and 2269 of SEQ ID NO:1 include this deletion. The presence of this deletion is useful in distinguishing between a polynucleotide of the present invention and some PRRSV clinical isolates (described in greater detail herein).

The isolated polynucleotides of the present invention can be obtained from a virus particle. As used herein, the terms "virus particle" and "viral particle" are used interchangeably and refer to a PRRSV particle. A virus particle includes an RNA polynucleotide that will reproduce in a cell, for instance a cell in a pig and/or a cultured primary (i.e., freshly isolated) porcine alveolar macrophage, under the appropriate conditions. A virus particle also includes an envelope that surrounds the polynucleotide. A virus particle is typically obtained from a pig presenting symptoms of mystery swine disease (MSD), including abortion, anorexia, fever, lethargy, pneumonia, red/blue discoloration of ears, labored breathing (dyspnea), and increased respiratory rate (tachypnea). While not intending to be limiting, a virus particle can be obtained from such a pig by the removal of tissue, preferably lung tissue, followed by microscopic examination of the tissue for thickened alveolar septae caused by the presence of macrophages, degenerating cells, and debris in alveolar spaces. These characteristics indicate the presence of an infection by a PRRSV. The lung or other porcine tissue is then homogenized with a pharmaceutically acceptable aqueous solution (such as physiological saline, Ringers solution, Hank's Balanced Salt Solution, Minimum Essential Medium, and the like) such that the tissue includes about 10 percent weight/volume amount of the homogenate. The virus can be isolated by low speed centrifugation as described in Example 1 to form a homogenate. Alternatively, the virus can be isolated by passing the homogenate through filters with pore diameters in the 0.05 to 10 micron range, preferably through a series of 0.45, 0.2 and 0.1 micron filters, to produce a homogenate containing the PRRSV. As a result, the homogenate contains viral particles having a size no greater than about 1.0 micron, preferably no greater than about 0.2 to 0.1 micron. Other tissues, including fetal tissue, may also be used to recover virus. Typically, such a virus particle is then grown in vivo (i.e., within the body of a subject) or in cell culture (i.e., in vitro) to produce more virus particles. This process of infecting an animal or a cell in culture, allowing the virus to reproduce, and then harvesting the newly produced virus is referred to herein as passaging the virus. Optionally, the virus is purified.

The homogenate described above can be passaged in cell culture by inoculation into a series of cultured cells. Cultured cells can be mammalian organ cells such as kidney, liver, heart and brain, lung, spleen, testicle, turbinate, white and red blood cells and lymph node cells, as well as insect and avian embryo preparations. Preferably, the cell is a primary porcine alveolar macrophage. Preferably, primary porcine alveolar macrophages are isolated from at least two pigs, and the primary porcine alveolar macrophages from each pig are not combined. It has been observed that there is some variability in the ability of the virus of the present invention to replicate in primary porcine alveolar macrophage, and the use of primary porcine alveolar macrophages from more than one pig significantly increases the ability to passage the virus in the macrophages. Culture media suitable for these cell preparations include those supporting mammalian cell growth such as serum (for instance, fetal calf serum or swine serum) and agar, blood infusion agar, brain-heart infusion glucose broth and agar and the like. After inoculating cultured cells with homogenate and growing the culture, individual clumps of cultured cells can be harvested and reintroduced into sterile culture medium with cells. Alternatively and preferably, supernatants from cultured cells are subjected to low speed centrifugation and used to inoculate sterile culture medium containing cells.

Whether an isolated, preferably purified, virus particle obtained in this way is able to cause MSD can be determined by inoculation of 3 to 4 week old pigs as described in Example 1, or by the methods of Terpstra et al., (*Vet. Q.*, 13, 131–136 (1991)), and Collins et al., (U.S. Pat. No. 5,846, 805). These methods experimentally test if the viral particle reproduces late term abortion and reproductive failure in pregnant sows or clinical signs and microscopic lesions in gnotobiotic piglets similar to field outbreaks. Pigs experimentally inoculated in this manner can also be used for in vivo passage of the virus by collecting tissue and processing for the isolation of virus as described in Example 1.

After isolation, preferably purification, of the virus particle, the polynucleotide in the particle can be isolated by, for instance, treating the particle to remove the envelope. Methods for removing the envelope are known in the art and include, for instance, solubilizing with phenol:chloroform or guanidunium. Optionally, the polynucleotide is purified using methods known to the art, including, for instance, precipitating the polynucleotide.

The polynucleotides of the present invention can be present in a vector. A vector is a replicating polynucleotide, such as a plasmid, phage, cosmid, or artificial chromosome to which another polynucleotide (e.g., a polynucleotide of the present invention) may be attached so as to bring about the replication of the attached polynucleotide. When a polynucleotide of the present invention is in a vector the polynucleotide is DNA. When present in a vector, a polynucleotide of the invention can be referred to as a "recombinant polynucleotide." Construction of vectors containing a polynucleotide of the invention employs standard ligation techniques known in the art. See, e.g., Sambrook et al, *Molecular Cloning: A Laboratory Manual.*, Cold Spring Harbor Laboratory Press (1989) or Ausubel, R. M., ed. *Current Protocols in Molecular Biology* (1994).

A vector can provide for further cloning (amplification of the polynucleotide), i.e., a cloning vector, or for expression of the polypeptide encoded by a coding region present in the polynucleotide, i.e., an expression vector. Selection of a vector depends upon a variety of desired characteristics in the resulting construct, such as a selection marker, vector replication rate, and the like. Suitable host cells for cloning or expressing the vectors herein are prokaryote or eukaryotic cells, and suitable vectors for cloning and/or expression in prokaryote and/or eukaryote cells are known to the art. Typically, when the vector is used to clone a polynucleotide, the host cell is a prokaryote. Suitable prokaryotes include eubacteria, such as gram-negative or gram-positive organisms. Preferably, *E. coli* is used. Host cells suitable for expression of the polypeptides of the invention are described in greater detail below.

The polynucleotide used to transform the host cell optionally includes one or more marker sequences, which typically encode a molecule that inactivates or otherwise detects or is detected by a compound in the growth medium. For example, the inclusion of a marker sequence can render the transformed cell resistant to an antibiotic, or it can confer compound-specific metabolism on the transformed cell. Examples of a marker sequence are sequences that confer resistance to kanamycin, ampicillin, chloramphenicol, tetracycline, neomycin, and formulations of phleomycin D1 including, for example, the formulation available under the trade-name ZEOCIN (Invitrogen).

An expression vector optionally includes regulatory sequences operably linked to the coding sequence. The invention is not limited by the use of any particular promoter, and a wide variety are known. Promoters act as regulatory signals that bind RNA polymerase in a cell to initiate transcription of a downstream (3' direction) coding sequence. The promoter used in the invention can be a constitutive or an inducible promoter. It can be, but need not be, heterologous with respect to the host cell. Examples of promoters for use in vectors present in prokaryotic cells include lac, lacUV5, tac, trc, T7, SP6 and ara.

Promoter sequences are known for eukaryotes. Most eukaryotic coding sequences have an AT-rich region located approximately 25 to 30 bases upstream from the site where transcription is initiated. Another sequence found 70 to 80 bases upstream from the start of transcription of many genes is the CXCAAT region where X may be any nucleotide. At the 3' end of most eukaryotic genes is an AATAAA sequence that may be a signal for addition of the poly A tail to the 3' end of the coding sequence. All these sequences are suitably inserted into eukaryotic expression vectors.

Transcription of a coding sequence encoding a polypeptide of the present invention in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, and Hepatitis-B virus.

Transcription of a coding sequence encoding a polypeptide of the present invention by eukaryotes can be increased by inserting an enhancer sequence into the vector. Enhancers are cis-acting elements of DNA, usually having about 10 to 300 bp, that act on a promoter to increase its transcription. Enhancers are relatively orientation- and position-independent, having been found 5' and 3' to coding sequences, within an intron as well as within the coding sequence itself. Many enhancer sequences are now known from mammalian genes (globin, elastase, albumin, alpha-fetoprotein, and insulin). Enhancers from eukaryotic cell viruses are also known and include the SV40 enhancer on the late side of the replication origin, the cytomegalovirus early promoter enhancer, the polyoma enhancer on the late side of the replication origin, and adenovirus enhancers. The enhancer may be spliced into the vector at a position 5' or 3' to the coding sequence encoding a polypeptide of the present invention, but is preferably located at a site 5' of the promoter.

An expression vector can optionally include a ribosome binding site (a Shine Dalgarno site for prokaryotic systems or a Kozak site for eukaryotic systems) and a start site (e.g., the codon ATG) to initiate translation of the transcribed message to produce the enzyme. It can also include a termination sequence to end translation. A termination sequence is typically a codon for which there exists no corresponding aminoacetyl-tRNA, thus ending polypeptide synthesis. The polynucleotide used to transform the host cell can optionally further include a transcription termination sequence. The rrnB terminators, which is a stretch of DNA that contains two terminators, T1 and T2, is an often used terminator that is incorporated into bacterial expression systems. Transcription termination sequences in vectors for eukaryotic cells typically include a polyadenylation signal 3' of the coding sequence.

Suitable host cells for expression vector that includes a polynucleotide encoding a polypeptide of the invention can be derived from multicellular organisms. Such host cells are capable of processing and glycosylation activities. Vertebrate or invertebrate culture can be used. Numerous baculoviral strains and variants and corresponding permissive insect host cells from hosts such as *Spodoptera frugiperda, Aedes aegypti, Aedes albopictus, Drosophila melanogaster, Trichoplusia ni*, and *Bombyx mori* are known to the art.

Vertebrate cells can also be used as hosts. Examples of useful mammalian host cell lines are monkey kidney CV1 line transformed by SV40 (CAS-7, ATCC CRL-1651); human embryonic kidney line (293 or 293 cells subcloned for growth in suspension culture, Graham et al., *J. Gen. Virol.*, 36:59 (1977)); baby hamster kidney cells (BHK, ATCC CCL 10); Chinese hamster ovary cells/-DHFR (CHO); CHO-K1 (ATCC CCL-61); CHO-D; mouse sertoli cells (TM4); monkey kidney cells (CV1, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (WI 38, ATCC CCL 75); human liver cells (Hep G2, HB 8065); mouse mammary tumor (MMT 060562, ATCC CCL 51); TRI cells; MRC 5 cells; FS4 cells; a human hepatoma line (Hep G2), MARC-145 (Kim et al., Arch. Virol., 133, 477–483 (1993)), and MA-104 (ATCC CRL-2378).

An expression vector of the present invention can be used to determine if a polynucleotide of the present invention replicates in a cell. A polynucleotide of the invention replicates in a cell if the cell culture shows signs of cytopathic effect (CPE) as described in Example 2, and/or if virus particles can be isolated from the cells. The polynucleotide present in the expression vector can be transcribed in vitro (i.e., cell free) to produce RNA transcripts. The RNA transcripts can be introduced into cultured cells, and incubated under conditions suitable for replication of a PRRSV. RNA transcripts that replicate will use the cellular machinery (including, for instance, ribosomes, and tRNAs) to replicate. The culture can be assayed as described in Example 2 for CPE. The presence of CPE indicates the virus is able to replicate in a cell. Optionally, the virus particles produced by the cells can be isolated. This type of expression vector is often referred to in the art as an infectious cDNA clone, and the RNA produced by the expression vector is referred to as an infectious RNA. Methods for cloning the European PRRSV Lelystad and inserting it into a vector are known to the art (Meulenberg et al., J. Virol., 72, 380–387 (1998)), and it is expected that the polynucleotides of the present invention can be used in this way to produce infectious RNAs. Moreover, the method of Meulenberg et al. can be used to make viral particles. Accordingly, a person of skill in the art can provide a polynucleotide of the present invention, for instance SEQ ID NO:1, introduce the polynucleotide into an expression vector, and produce infectious RNAs that could be introduced to cells to result in the production of virus particles. The cells transfected with an infectious RNA can be, for instance, BHK-21 cells, CL-2621 cells, MA-104 cells, MARC-145 cells, or primary porcine alveolar macrophages, preferably primary porcine alveolar macrophages. Methods for efficiently transfecting cells include the use of calcium chloride, and commercially available products known under the trade names LIPOFECTIN and LIPOFECTAMINE. Methods for efficiently transfecting primary porcine alveolar macrophages are known to the art (Groot Bramel-Verheige et al., Virol., 278, 380–389 (2000)).

Polypeptides

The present invention is also directed to polypeptides, preferably isolated polypeptides, encoded by polynucleotides of the present invention. Preferably, a polypeptide of the present invention has immunogenic activity. "Immunogenic activity" refers to an amino acid sequence which elicits an immunological response in a subject. An immunological response to a polypeptide is the development in a subject of a cellular and/or antibody-mediated immune response to the polypeptide. Usually, an immunological response includes but is not limited to one or more of the following effects: the production of antibodies, B cells, helper T cells, suppressor T cells, and/or cytotoxic T cells (see, for example, de Antonio et al., Vet. Immunol. Immunopathol., 61, 265–277 (1998), and Kwang et al., Res. Vet. Sci., 67, 199–201 (1999)) directed specifically to an epitope or epitopes of the polypeptide fragment. As used herein, an antibody that can "specifically bind" or is "specific for" a virus particle and/or a polypeptide is an antibody that interacts only with an epitope of the antigen that induced the synthesis of the antibody, or interacts with a structurally related epitope. An antibody that "specifically binds" a European-like PRRSV is an antibody that does not specifically bind a European PRRSV, preferably a European PRRSV having deposit number I-1102, or a North American PRRSV, preferably a North American PRRSV having deposit number VR-2332. As used herein, the term "complex" refers to the combination of an antibody and a virus particle and/or a polypeptide that results when an antibody specifically binds to a virus particle and/or a polypeptide.

Preferred examples of polypeptides of the invention are SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10 (see Table 1). The present invention further includes polypeptides having structural similarity with the polypeptides of the present invention. The structural similarity is referred to as percent identity and is generally determined by aligning the residues of the two amino acid sequences (i.e., a candidate amino acid sequence and the amino acid sequence of one of SEQ ID NOs:2–10) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence is the amino acid sequence being compared to an amino acid sequence present in a preferred polypeptide of the present invention. Preferably, two amino acid sequences are compared using the GAP program of the GCG Wisconsin Package (Genetics Computer Group, Madison, Wis.) version 10.0 (update January 1999). The GAP program uses the algorithm of Needleman and Wunsch (J. Mol. Biol., 48, 443–453 (1970)) to find the alignment of two complete sequences that maximizes the number of matches and minimizes the number of gaps. Preferably, the default values for all GAP search parameters are used, including scoring matrix=BLOSUM62.cmp, gap weight=8, length weight=2, average match=2.912, and average mismatch=−2.003. In the comparison of two amino acid sequences using the GAP search algorithm, structural similarity is referred to as "percent identity." Preferably, a polypeptide includes an amino acid sequence having a structural similarity with SEQ ID NO:2 of at least about 95%, more preferably at least about 97%, most preferably at least about 99% identity. Preferably, a polypeptide includes an amino acid sequence having a structural similarity with SEQ ID NO:3 of at least about 99% identity. Preferably, a polypeptide includes an amino acid sequence having a structural similarity with SEQ ID NO:4 of at least about 98%, more preferably at least about 99% identity. Preferably, a polypeptide includes an amino acid sequence having a structural similarity with SEQ ID NO:5 of at least about 94%, more preferably at least about 96%, most preferably at least about 99% identity. Preferably, a polypeptide includes an amino acid sequence having a structural similarity with SEQ ID NO:6 of at least about 95%, more preferably at least about 97%, most preferably at least about 99% identity. Preferably, a polypeptide includes an amino acid sequence having a structural similarity with SEQ ID NO:7 of, in increasing order of preference, at least about 91%, at least about 93%, at least about 95%, at least about 97%, most preferably at least about 99% identity. Preferably, a polypeptide includes an amino acid sequence having a structural similarity with SEQ ID NO:9 of at least about 99% identity. Preferably, a polypeptide includes an amino acid sequence having a structural similarity with SEQ ID NO: 10 of at least about 99.5% identity.

The present invention further includes polypeptide analogs and polypeptide fragments, preferably immunogenic polypeptide analogs and immunogenic polypeptide fragments. Preferably, a polypeptide fragment is at least about 8, more preferably at least about 12, most preferably at least about 20 amino acids in length. Immunogenic analogs of polypeptides of the present invention include polypeptides having amino acid substitutions that do not eliminate the ability of the polypeptide to elicit an immunological response. Substitutes for an amino acid may be selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, aspartate, and glutamate. The positively charged (basic) amino acids include arginine, lysine, and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$.

Immunogenic analogs, as that term is used herein, also include modified polypeptides. Modifications of polypeptides of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Immunogenic fragments of a polypeptide include a portion of the polypeptide containing deletions or additions of one or more contiguous or noncontiguous amino acids such that the resulting polypeptide is immunogenic.

The polypeptides of the present invention can be obtained from, for instance, a biological sample from a porcine subject infected with a European-like PRRSV that encodes the polypeptide. Preferably, the European-like PRRSV is one that includes SEQ ID NO: 1, more preferably it is the European-like PRRSV having ATCC number PTA-2194. The polypeptide can be obtained from cultured cells, preferably primary porcine alveolar macrophages, that have, for instance, been infected with a European-like PRRSV that encodes the polypeptide or contain a recombinant polynucleotide, preferably a polynucleotide of the invention, that encodes a polypeptide of the invention. Alternatively, the polypeptide can be obtained from a prokaryotic cell or a eukaryotic cell that contains an expression vector that includes a polynucleotide encoding a polypeptide of the invention. The polypeptides of the present invention can also be obtained by chemical synthesis.

Viruses

The present invention includes isolated European-like virus particles. The European-like virus particles of the present invention include a polynucleotide having structural similarity to SEQ ID NO: 1, preferably at least about 96%, more preferably at least about 98%, most preferably at least about 99% identity to SEQ ID NO: 1. A preferred example of a virus particle is one that includes SEQ ID NO: 1. More preferably, the virus particle is the virus having ATCC Accession Number PTA-2194. A virus particle of the present invention include an envelope, and can, when added to a cultured cell, can replicate to result in the production of more viral particles.

As discussed above, a virus particle of the present invention can be obtained from a pig presenting symptoms of MSD. A virus particle can be grown by passage in vivo or in cell culture. Passage in vivo includes inoculating a pig, for instance as described in example 1. Passage in cell culture includes exposing cultured cells to the virus particle and incubating the cells under conditions suitable for the virus to reproduce and produce more virus particles. Preferably, the cultured cells are not an immortalized or transformed cell line (i.e., the cells are not able to divide indefinitely). Preferably, primary porcine alveolar macrophages are used for passage in cell culture. The use of primary porcine alveolar macrophages is described in Example 2. A virus particle can also be obtained from cells transfected with an infectious RNA as described herein.

A virus of the present invention can be inactivated, i.e., rendered incapable of reproducing in vivo and/or in cell culture. Methods of inactivation are known to the art and include, for instance, treatment of a virus of the invention with a standard chemical inactivating agent such as an aldehyde reagent including formalin, acetaldehyde and the like; reactive acidic alcohols including cresol, phenol and the like; acids such as benzoic acid, benzene sulfonic acid and the like; lactones such as beta propiolactone and caprolactone; and activated lactams, carbodiimides and carbonyl diheteroaromatic compounds such as carbonyl diimidazole. Irradiation such as with ultraviolet and gamma irradiation can also be used to inactivate the virus.

Also included in the present invention are attenuated European-like PRRSV (i.e., viruses having reduced ability to cause the symptoms of MSD in pigs), and methods of making an attenuated European-like PRRSV. Methods of producing an attenuated virus are known to the art. Typically, a virus of the present invention is passaged, i.e., used to infect a cell in culture, allowed to reproduce, and then harvested. This process is repeated until the virulence of the virus in pigs is decreased. For instance, the virus can be passaged 10 times in cell culture, and then the virulence of the virus measured. If virulence has not decreased, the virus that was not injected into the animal is passaged an additional 10 times in cell culture. This process is repeated until virulence is decreased. In general, virulence is measured by inoculation of pigs with virus, and evaluating the presence of clinical symptoms and/or $LD_{50}$ (see, for instance, Example 1, Halbur et al., *J. Vet. Diagn. Invest.*, 8, 11–20 (1996), and Halbur et al., *Vet. Pathol.*, 32, 200–204 (1995), and Park et al., *Am. J. Vet. Res.*, 57, 320–323 (1996)). Preferably, virulence is decreased so the attenuated virus does not cause the death of animals, and preferably does not cause clinical symptoms of the disease.

Typically, a cell culture useful for producing an attenuated virus of the present invention includes cells of non-porcine mammal origin. Examples of non-porcine mammal cell cultures include, for instance, the cell line MA-104 (ATCC CRL-2378), the cell line MARC-145 (Kim et al., *Arch. Virol.*, 133, 477–483 (1993)), and the cell line CL-2621 (Baustia et al., *J. Vet. Diagn. Invest.*, 5, 163–165 (1993)). Preferably, a mixed cell culture is used for producing an attenuated virus of the present invention. In a mixed cell culture there are at least two types of cells present. Preferably, a mixed cell culture includes an immortalized or transformed cell line and a primary cell culture. A mixed cell culture is particularly useful when a virus reproduces slowly, or not at all, in an immortalized or transformed cell line. Preferred examples of an immortalized or transformed cell line for use in a mixed cell culture include, for example, the cell line MARC-145 (Kim et al., *Arch. Virol.*, 133, 477–483 (1993)), and the cell line MA-104 (ATCC CRL-2378). Preferably, primary cell cultures for use in a mixed cell culture are porcine in origin. A preferred example of a primary cell culture for use in a mixed cell culture is primary porcine alveolar macrophages.

Methods of Use

The virus particles, polynucleotides, polypeptides, and immunogenic analogs and immunogenic fragments thereof of the present invention can be used to produce antibodies. Laboratory methods for producing, characterizing, and optionally isolating polyclonal and monoclonal antibodies are known in the art (see, for instance, Harlow E. et al. *Antibodies: A laboratory manual* Cold Spring Harbor Laboratory Press, Cold Spring Harbor (1988). For instance, a virus of the present invention can be administered to an animal, preferably a mammal, in an amount effective to cause the production of antibody specific for the administered virus. Polypeptides of the present invention and immunogenic analogs and immunogenic fragments thereof can also be administered to an animal, preferably a mammal, to produce antibodies. Optionally, a virus particle or a polypeptide is mixed with an adjuvant, for instance Freund's incomplete adjuvant, to stimulate the production of antibodies upon administration. Preferably, the antibody is a monoclonal antibody.

Preferably, an antibody produced using a virus of the present invention, or a polypeptide or immunogenic analog or immunogenic fragment thereof, is a neutralizing antibody. A neutralizing antibody is one that prevents a virus of the present invention from reproducing in cell culture, preferably in primary porcine macrophages.

Optionally and preferably, antibody produced using a virus particle of the present invention, a polypeptide or polynucleotide of the present invention, or immunogenic analogs and immunogenic fragments thereof do not specifically bind to the European PRRSV deposited as I-1102 with the Collection Nationale De Cultures De Microorganisms, Institut Pasteur, France, or to the North American PRRSV deposited as VR-2332 with the ATCC. Whether an antibody of the present invention specifically binds to either or both of those viruses can be determined using methods known to the art.

The present invention provides methods for detecting a PRRSV, preferably a virus of the present invention. These methods are useful in, for instance, detecting a PRRSV in an animal, detecting a PRRSV in a cell culture, or diagnosing a disease caused by a PRRSV. Preferably, such diagnostic systems are in kit form. Kits are described in greater detail below. In some aspects of the invention, detecting a PRRSV includes detecting antibodies that specifically bind to a virus of the present invention, a polypeptide of the present invention, and/or an immunogenic analog or immunogenic fragment thereof. The method includes providing a biological sample, preferably a liquid homogenate of a tissue sample, from a porcine subject. The subject can be suspected of harboring the PRRSV, or can be a member of a herd that is being screened for the presence of the PRRSV. Antibody is added to the biological sample and incubated under conditions to form a complex with a PRRSV in the biological sample. Preferably the antibody is produced using a virus particle of the present invention, a polypeptide or polynucleotide of the present invention, or an immunogenic analog or immunogenic fragment thereof. Preferably, the antibody does not specifically bind a European PRRSV or a North American PRRSV. The complex is then detected, and the presence of the complex indicates the presence of a PRRSV in the biological sample. The detection of antibodies is known in the art and can include, for instance, immunofluorescence and peroxidase. Typical formats in which antibodies of the present invention can be used include, for instance, enzyme linked immunosorbent assay (ELISA); radioimmunoassay (RIA), immunofluorescent assay (IFA), and western immunoassay.

As used herein, a "biological sample" refers to a sample of tissue or fluid obtained from a subject, including but not limited to, for example, lung or respiratory tract. A "biological sample" also includes samples of cell culture constituents including but not limited to the cells and media resulting from the growth of cells and tissues in culture medium. The cells can be infected with PRRSV or can contain a vector that includes a polypeptide of the present invention, and preferably includes a coding region encoding a polypeptide of the present invention.

Other methods for detecting a PRRSV, preferably a European-like PRRSV, include the amplification of a polynucleotide, preferably by the polymerase chain reaction (PCR). The polynucleotide can be one that is, for instance, present in a biological sample from a porcine subject that is suspected of harboring the PRRSV, or a member of a herd that is being screened for the presence of the PRRSV. The polynucleotide can be obtained from an isolated, preferably purified, virus particle. When the polynucleotide is obtained from a virus particle, the polynucleotide is converted from an RNA polynucleotide to a DNA polynucleotide by reverse transcription (see, for instance, Example 3). In some aspects of the present invention, the methods to detect a European-like PRRSV and distinguish it from a European PRRSV and a North American PRRSV exploit the presence of a deletion present in European-like PRRSV. This deletion is described above in the section labeled "Polynucleotides."

In one aspect of detecting a PRRSV by amplification of a polynucleotide, the invention is directed to detecting a virus of the present invention under conditions where European PRRSV and North American PRRSV are not detected. The method includes contacting a viral polynucleotide that is suspected of being a European-like PRRSV with a primer pair and incubating under conditions to form a detectable amplified polynucleotide. As used herein, a "primer pair" refers to two single stranded polynucleotides that can be used together to amplify a region of a polynucleotide, preferably by a polymerase chain reaction (PCR). The polynucleotide that results from amplifying a region of a polynucleotide is referred to as an "amplification product" or an "amplified polynucleotide." The phrase "under conditions suitable to form a detectable amplification product" refers to the reactions conditions that result in an amplification product. For instance, in the case of a PCR, the conditions suitable to form a detectable amplification product include the appropriate temperatures, ions, and enzyme.

One of the primers of the primer pair is complementary to a portion of the viral polynucleotide that corresponds to nucleotides 2268 and 2269 of SEQ ID NO: 1, or the complement thereof. The use of such a primer results in the production of an amplified polynucleotide when there is a deletion. In contrast, the use of such a primer with a European PRRSV will not result in the production of an amplified polynucleotide because there are about 51 nucleotides present between the nucleotides that correspond to nucleotides 2268 and 2269 of SEQ ID NO: 1, or the complement thereof. For instance, the use of such a primer pair will not result in an amplified polynucleotide when the viral polynucleotide is from the Lelystad PRRSV. An example of a primer pair that can be used in this method includes forward primer 5'ATCGGGAATGCTCAGTC-CCCTT (SEQ ID NO:12), which corresponds to nucleotides 2,255 to 2,276 of SEQ ID NO:1 and reverse primer Euro2714 5'-GCGCATAAGACAGATCCA (SEQ ID NO:13), which is expected to result in an amplified polynucleotide of about 467 nucleotides. Another primer pair is reverse primer: 5'-AAGGGGACTGAGCATTCCCG (SEQ ID NO:14), which corresponds to the complement of nucleotides 2,257 to 2,276 of SEQ ID NO:1 and forward primer Euro20/5'-CAGAAGGGTTCGAGGAAG (SEQ ID NO:15), which is expected to result in an amplified polynucleotide of about 170 nucleotides.

In another aspect of detecting a PRRSV by amplification of a polynucleotide, the invention is directed to detecting a virus of the present invention under conditions where both European-like PRRSV and European PRRSV are detected, and the molecular weights of the amplified polynucleotides vary. The primer pair used in this aspect produces an amplified polynucleotide that includes the region of the deletion, i.e., nucleotides 2268 and 2269 of SEQ ID NO: 1, and the corresponding nucleotides of a European PRRSV. When both a European-like PRRSV and European PRRSV are amplified, and the resulting amplified polynucleotides are compared, the amplified polynucleotide that results from the European-like PRRSV will have a molecular weight that is about 51 nucleotides less than an amplified polynucleotide from a European PRRSV. Methods of determining the approximate molecular weight of an amplified polynucleotide are known in the art, and include, for instance, resolving the polynucleotide on an acrylamide or agarose gel.

An example of a primer pair that can be used in this method includes forward primer Euro1671/5'-GCCTGTC-CTAACGCCAAGTAC (SEQ ID NO: 16) and reverse primer/Euro3165-rc: 5'-CATGTCCACCCTATCCCACAT (SEQ ID NO:17), which results in an amplified polynucleotide in a European-like PRRSV of about 1,494 nucleotides, and an amplified polynucleotide in a European PRRSV of about 1,544 nucleotides. Other primer pairs include forward primer Euro20/5'-CAGAAGGGTTCGAGGAAG (SEQ ID NO: 15) and reverse primer/Euro3207 5'-GCTTGGAACT-GCGAGG (SEQ ID NO: 19) (expected size of amplified polynucleotide from a European-like PRRSV: about 910 nucleotides); forward primer Euro20/5'-CAGAAGGGTTC-GAGGAAG (SEQ ID NO:15) and reverse primer/Euro2714 5'-GCGCATAAGACAGATCCA (SEQ ID NO: 13) (expected size of amplified polynucleotide from a European-like PRRSV: about 616 nucleotides). When these primers are used to amplify a European PRRSV, the size of the amplified polynucleotide is expected to be about 51 nucleotides greater.

In another aspect of detecting a PRRSV by amplification of a polynucleotide, the invention is directed to detecting a virus of the present invention under conditions where European PRRSV is detected and European-like PRRSV are not detected. In this aspect of the invention, at least one of the primers of a primer pair is complementary a portion of nucleotides 2,419 to 2,470 of the prototype European PRRSV, Lelystad (Genbank Accession number NC_002533), of the complement thereof. An example of a primer pair that can be used in this method includes forward primer Euro1/: 5'-TGAAGGTGCTCTGGTCT (SEQ ID NO:20) and reverse primer/Euro2: 5'-AAATTCCCGC-CTACC (SEQ ID NO:21), which results in an amplified polynucleotide from a European PRRSV of about 51 nucleotides.

The present invention also provides a kit for detecting a virus of the present invention, and a kit for detecting a polypeptide of the present invention or an immunogenic analog or immunogenic fragment thereof. The kit includes an antibody that specifically binds a virus of the present invention, a polypeptide of the present invention or immunogenic analog or immunogenic fragment thereof (when detecting the presence of the virus) or a primer pair as described herein (when amplifying a polynucleotide) in a suitable packaging material in an amount sufficient for at least one assay. Preferably, the antibody does not specifically bind to the European PRRSV deposited as I-1102 with the Collection Nationale De Cultures De Microorganisms, Institut Pasteur, France, or to the North American PRRSV deposited as VR-2332 with the ATCC. The present invention also provides a kit for detecting antibody to a virus of the present invention, a polypeptide of the present invention or an immunogenic analog or immunogenic fragment thereof. When detecting antibody to the virus, polypeptide, or immunogenic analog or immunogenic fragment thereof the kit includes a virus of the present invention, a polypeptide of the present invention or immunogenic analog or immunogenic fragment thereof. Optionally, other reagents such as buffers and solutions needed to practice the invention are also included. Instructions for use of the packaged virus or polypeptide or primer pair are also typically included.

As used herein, the term "packaging material" refers to one or more physical structures used to house the contents of the kit. The packaging material is constructed by well known methods, preferably to provide a sterile, contaminant-free environment. The packaging material has a label which indicates that the polypeptide or primer pair can be used for detecting a virus of the present invention. In addition, the packaging material contains instructions indicating how the materials within the kit are employed to detect a virus of the present invention. As used herein, the term "package" refers to a solid matrix or material such as glass, plastic, paper, foil, and the like, capable of holding within fixed limits a virus or a primer pair. Thus, for example, a package can be a glass vial used to contain milligram quantities of a primer pair, or it can be a microtiter plate well to which microgram quantities of a virus have been affixed. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is also directed to vaccines and methods of treatment. Treatment can be prophylactic or, alternatively, can be initiated after the development of MSD in a porcine subject. A vaccine can include, for instance, an immunogenic composition or a neutralizing antibody. The term "vaccine" refers to a composition that, upon administration to a subject, will provide protection against a virus of the present invention. When the vaccine includes an immunogenic composition, administration to the subject will also produce an immunological response to a polypeptide and result in immunity. An immunogenic composition of the present invention can include an attenuated or inactivated virus of the present invention, and/or one or more polypeptides of the present invention or immunogenic analogs or immunogenic fragments thereof, and/or a polynucleotide.

As used herein, the term "immunogenic composition" refers to a composition or preparation administered in an amount effective to result in some therapeutic benefit or effect so as to result in an immune response that inhibits or prevents MSD in a subject, or so as to result in the production of antibodies to a PRRSV of the present invention. Both local and systemic administration is contemplated. Systemic administration is preferred.

A polynucleotide used in a vaccine of the invention is preferably one that includes a nucleotide sequence encoding a polypeptide on the present invention, or an immunogenic analog or immunogenic fragment thereof. The polynucleotide can include DNA, RNA, or a combination thereof. The polynucleotide can be supplied as part of a vector or as a "naked" polynucleotide. General methods for construction, production and administration of polynucleotide vaccines are known in the art, e.g. F. Vogel et al., Clin. Microbiol. Rev. 8:406–410 (1995); WO 93/02556; Felgner et al., U.S. Pat. No. 5,580,859, Pardoll et al., Immunity 3:165 (1995); Stevenson et al., Immunol. Rev. 145:211 (1995); Molling, J. Mol. Med. 75:242 (1997); Donnelly et al., Ann. N.Y. Acad. Sci. 772:40 (1995); Yang et al., Mol. Med. Today 2:476 (1996); and Abdallah et al., Biol. Cell 85:1 (1995)). A nucleic acid molecule can be generated by means standard in the art, such as by recombinant techniques, or by enzymatic or chemical synthesis.

Preferably, administration of a polynucleotide that is part of a vaccine includes the introduction of an expression vector that includes the polynucleotide. There are numerous plasmids known to those of ordinary skill in the art useful for the production of polynucleotide vaccine plasmids, including, for instance, the plasmid pVAX1 as the vector (In Vitrogen Corporation, Carlsbad, Calif.). In addition, the vector construct can contain immunostimulatory sequences that stimulate the animal's immune system. Examples of immunostimulatory sequences include, for instance, sequences with CpG motifs, two 5' purines, an unmethylated CpG dinucleotide, or two 3' pyrimidines (see, for instance, Lowie et al., DNA Vaccines Methods and Protocols, Humana Press, Totowa, N.J. (2000)). Other possible additions to the polynucleotide vaccine constructs include nucleotide sequences encoding cytokines, such as granulocyte macrophage colony stimulating factor (GM-CSF) or interleukin-12 (IL-12). The cytokines can be used in various combinations to fine-tune the response of the animal's immune system, including both antibody and cytotoxic T lymphocyte responses, to bring out the specific level of response needed to produce an immune response. Alternatively, the vaccine vector can be a viral vector, including an adenovirus vector, and adenovirus associated vector, or a retroviral vector.

Immunogenic carriers can be used to enhance the immunogenicity of a vaccine that includes an immunogenic composition. Such carriers include but are not limited to other polypeptides, polysaccharides, liposomes, and bacterial cells and membranes. Polypeptide carriers may be joined to the attenuated or inactivated virus of the present invention, and/or a polypeptide of the present invention or an immunogenic analog of immunogenic fragment thereof to form fusion polypeptides by recombinant or synthetic means or by chemical coupling. Useful carriers and means of coupling such carriers to polypeptide antigens are known in the art.

The vaccine preferably includes a pharmaceutical carrier that is compatible with a porcine subject. The vaccine may be delivered orally, parenterally, intranasally or intravenously. Factors bearing on the vaccine dosage include, for example, the age, weight, and level of maternal antibody of the infected pig. The vaccine doses should be applied over about 14 to 28 days to ensure that the pig has developed an immunity to the MSD infection.

The vaccine of the present invention can be administered in a variety of different dosage forms. An aqueous medium containing the vaccine may be desiccated and combined with pharmaceutically acceptable inert excipients and buffering agents such as lactose, starch, calcium carbonate, sodium citrate formed into tablets, capsules and the like. These combinations may also be formed into a powder or suspended in an aqueous solution such that these powders and/or solutions can be added to animal feed or to the animals' drinking water. These compositions can be suitably sweetened or flavored by various known agents to promote the uptake of the vaccine orally by the pig.

For purposes of parenteral administration, the composition can be combined with pharmaceutically acceptable carrier(s) well known in the art such as saline solution, water, propylene glycol, etc. In this form, the vaccine can be parenterally, intranasally, and orally applied by well-known methods known in the art of veterinary medicine. The vaccine can also be administered intravenously by syringe. In this form, the vaccine is combined with pharmaceutically acceptable aqueous carrier(s) such as a saline solution. The parenteral and intravenous formulations of the composition may also include emulsifying and/or suspending agents as well, together with pharmaceutically acceptable diluent to control the delivery and the dose amount of the composition.

The present invention is illustrated by the following examples. It is to be understood that the particular examples, materials, amounts, and procedures are to be interpreted broadly in accordance with the scope and spirit of the invention as set forth herein.

EXAMPLES

Example 1

Detection of Virus in Infected Pigs

This example describes the isolation of a new PRRSV from infected pigs. The PRRSV was given the designation MND99-35186 and is referred to in these examples as European-like.

Methods

Three live, 3 to 4-day-old pigs from a herd with a clinical history of late-gestation abortions and weak-born pigs were submitted to the Minnesota Veterinary Diagnostic Laboratory (St. Paul, Minn.). The pigs were euthanized by intravenous over dose of barbiturate and necropsied (autopsied).

Portions of lung, lymph nodes, brain, spleen, kidney, tonsil and heart were collected and pooled as one sample. The sample was treated for the isolation of porcine reproductive and respiratory syndrome virus (PRRSV), pseudorabies virus (PRV), and swine influenza virus (SIV).

For isolation of PRRSV, samples were inoculated on MARC-145 cells and primary porcine alveolar macrophages. Before inoculation, the samples were treated as described by Rossow et al. (Vet. Pathol., 32, 361–373 (1995)). Briefly, Hank's Balanced Salt Solution was added to the tissue sample or sera to make an approximately 10% (vol/vol) suspension, and then homogenized. The homogenate was centrifuged a 4,133×g for 20 minutes, and the supernatant removed and saved. The pelleted material was discarded. The conditions for inoculating MARC-145 cells and primary porcine alveolar macrophages are described below. In addition, serum from each pig was pooled together into one sample and then used to inoculate MARC-145 cells and primary porcine alveolar macrophages.

Portions of lung, lymph nodes, stomach, brain, liver, kidney, tonsil, heart and ileum (a section of the small intestine) were preserved in 10% formalin buffered with a mixture of dibasic sodium phosphate and monobasic sodium phosphate to yield pH 7.0. The tissues were incubated in the formalin for at least 12 hours before subsequent use in assays. Portions of each tissue were paraffin embedded.

Formalin fixed tissues were stained by hematoxylin and eosin (H and E) staining.

Formalin fixed tissues were also assayed for PRRSV testing by immunohistochemical technique by the method of Christopher-Hennings et al., (*Vet. Pathol.*, 35, 260–267 (1998)). Briefly, formalin fixed, paraffin embedded lung was sectioned at approximately 4 microns and sections were applied to glass slides. Tissue sections were covered with the monoclonal antibody SDOW-17 and incubated in a humidified chamber. SDOW-17 is an anti-PRRSV monoclonal antibody that recognizes an epitope present on the Lelystad PRRSV and on the VR-23332 PRRSV. Antibody binding to PRRSV in the lung was identified using a modified avidin biotin complex method (Hsu et al., *J. Histochem. Cytochem.*, 29, 577–580 (1981)).

Lung sections were rapidly frozen in isopentane at −30° C. The frozen sections were examined for PRRSV by direct fluorescent antibody technique using the monoclonal antibody SDOW-17. Direct FA examination of tissue was done by the method of Rossow et al. (*Vet. Pathol.*, 32, 361–373 (1995)). Briefly, tissues were frozen, sectioned at approximately 5 microns and transferred to glass slides. Tissue sections were covered with fluoroscene-conjugated SDOW-17, an anti-PRRSV monoclonal antibody (obtained from E. Nelson, South Dakota State University, South Dakota). The tissue sections were then incubated in a humidified chamber for about 1 hour, and excess unbound antibody removed by washing in phosphate buffered saline. The presence of antibody binding to PRRSV in the lung was visualized with a fluorescent microscope.

Brain, lung, and liver samples were cultured on blood agar plates to detect the presence of aerobic bacteria.

Pooled tissues were also examined for leptospira using the method of Smith et al. (*Cornell Vet.*, 57, 517–526 (1967)).

Results

PRRSV was identified in lung sections from each pig by immunohistochemical and direct fluorescent antibody.

Light microscopic tissue lesions (H and E slides) were compatible with PRRSV infection. Histopathology of the lungs showed diffuse septal thickening by macropahges. Some alveoli contained necrotic cell debris. Lymph nodes were characterized by germinal centers filled with blast-lymphocytes and small foci of necrosis. The muscular layer in one stomach was characterized by lymphoplasmacytic perineuritis and perivasculitis. Brain, liver, kidney, tonsil, heart, and ileum did not have lesions.

Tests for PRV and SIV were negative and no bacterial pathogens were identified in tissues from the infected pigs.

PRRSV was isolated from pooled tissue homogenate and pooled sera cultured in the alveolar macrophages. However, few cells were infected with PRRSV. No PRRSV was isolated from either sample cultured in MARC-145 cells.

Because this PRRSV grew poorly in the alveolar macrophages, 3 to 4-week-old pigs from a documented PRRSV-free farm were inoculated (intramuscularly and intranasally) with approximately 1 ml of the virus obtained from the supernatant from the infected alveolar macrophages. The virus was diluted by adding about 9 mls of Hanks Balanced Salt Solution to about 1 ml of virus-containing supernatant. Clinically, the experimentally infected pigs exhibited the same symptoms of mild, transient signs of lethargy within about 1–2 days that are also seen after infection of a pig with Lelystad virus or VR-2332. Each infected pig seroconverted to the PRRSV infection. Seroconversion was measured by the IDEXX Elisa test (HerdChek-PRRSV, IDEXX Laboratories Inc. Westbrook, Me.). Seroconversion was also measured by indirect fluorescent antibody test using Lelystad infected cells and the method of Yoon et al. (*J. Vet. Diagn. Invest.*, 4, 144–147 (1992)). The European-like PRRSV was re-isolated from infected pig tissues and serum, cultured in porcine alveolar macrophages, and identified in tissues by immunohistochemistry.

Example 2

Infection of Porcine Alveolar Macrophages with PRRSV

Porcine alveolar macrophages were isolated by collection from PRRSV-negative pigs less than 6-weeks-old. Pigs were euthanized, and trachea and lungs removed and airways lavaged with sterile phosphate buffered saline. The phosphate buffered saline was made by combining 8.5 grams NaCl, 1.1 grams disodium phosphate, and 0.32 gram sodium monophosphate in 10 liters distilled water. The Porcine alveolar macrophages were concentrated by centrifugation, confirmed negative for PRRSV by isolation and examination using direct fluorescent antibody as described in Example 1, and used immediately or stored in liquid nitrogen at a concentration of $10^6$ cells/ml. Frozen alveolar macrophages chould be used within 6 months.

Freshly harvested porcine alveolar macrophages (about $10^7$) or frozen cells ($10^6$ cells) were plated on a 1×48 well plate or a 1×75 cm flask, and allowed to adhere for 4 hours to overnight in about 10 to 25 ml RPMI-1640 complete medium. The cells cannot be allowed to incubate for more than one day before virus is added. RPMI-1640 complete medium is made by combining 500 ml RPMI-1640 medium containing 300 mg/liter L-glutamine, 25 mM HEPES [N-(2-Hydroxyethyl)piperazine-N'-(2-ethanesulfonic acid)] (Catalog #10-041-CV, Mediatech Inc., Herndon. Va.), 40 ml heat-inactivated Fetal Bovine Serum (Cat #12133-78P; JRH Bioscience, Inc., Lenexa, Kans.), 1 gram neomycin sulfate (Gibco Life Technologies, Rockville, Md.), 40 ml Hanks Balanced Salt Solution (HBSS) (Gibco Life Technologies, #14180053, Rockville, Md.) containing neomycin sulfate at a final concentration of 150 µg/ml medium), 66 ml HBSS containing penicillin G potassium salt (Sigma #P7794, St. Louis, Mo.), streptomycin sulfate (Sigma #S9137), and amphotericin B solubilized (Sigma A-9528) at a final concentration of 2500 U penicillin G, 0.45 mg streptomycin sulfate/ml medium, and 120 µg/ml amphotericin B/ml of medium.

The medium was removed, and the cells were washed in once ins HBSS, and the cells were infected with 1 ml of virus in 1 ml RPMI incomplete medium (same as RPMI complete but without FBS added). The virus titer can vary, and when the virus is from tissue isolated from a PRRSV-infected pig, is unknown. HBSS was 500 mls HBSS supplemented with 5 mls of 100× neomycin (10 mg/ml) and 5 mls of 100× pennecillin (10,000 U ml), streptomycin (10 mg/ml), and fungizone (25 µg/ml).

The plate was gently rotated for 1 hour at room temperature. Nine mls of RPMI complete medium were added and the infected cells were incubated at 37° C. The cell were observed daily until 60–80% cytopathic effect (CPE) was seen (2–3 days). CPE appears as fragmented, vacuolated, malformed, shrunken cells.

Virus was isolated by removing the medium and centrifuging at about 4,000×g for 10 minutes to remove cellular debris, and leave the virus in the supernatant.

The presence of PRRSV in the primary porcine alveolar macrophages was confirmed by staining with the SDOW-17 monoclonal antibody as described by Nelson et al. (*J. Clin. Microbiol.*, 34, 3184–3189 (1993)).

Example 3

Sequence Analysis of Virus

1. PRRSV RNA Extraction:

Viral RNA was extracted from macrophage culture supernatants using QIAamp Viral RNA Mini Spin Kit (QIAgen, Inc., Valencia, Calif.). Briefly, 280 μl cell culture fluid was added to 1120 μl Buffer AVL/Carrier RNA, pulse vortexed for 15 seconds, incubated at room temperature for 10 minutes, and centrifuged briefly. After this step, 1120 μl 100% ethanol was added to the reaction, pulse vortexed for 15 seconds, and centrifuged briefly. The reaction was then applied to a QIAamp spin column (in a 2 ml collection tube) in 630 μl aliquots (4×) and centrifuged at 6000×g (800 rpm) for 1 minute, discarding flow-through each time. When all sample was applied to the filter, the QIAamp spin column was placed into a clean 2 ml collection tube, and again centrifuged. Buffer AW1 (500 μl) was added to the filter containing viral RNA, and this reaction was centrifuged at 6000×g (8000 rpm) for 1 minute. Buffer AW2 (500 μl) was added to the spin column and the column was centrifuged at full speed (20,000×g; 14,000 rpm) for 3 minutes. The collection tube was discarded, and the QIAamp spin column was place in a clean 1.5 ml centrifigue tube. Buffer AVE (60 μl) was added to the spin column, the column incubated at room temperature for 1 minutes, and then centrifuged at 6000×g (8000 rpm) for 1 minutes.

2. RT-PCR: Two methods were used to reverse transcribe the viral RNA and obtain DNA for use in DNA sequence analysis. In general, the primers were selected to hybridize to an appropriate portion of SEQ ID NO: 1 and amplify a DNA fragment that was then used in DNA sequencing reactions.

a. Qiagen OneStep RT-PCR:

Five microliters of extracted RNA were added to a reaction mix containing 1× Qiagen RT-PCR Buffer; 400 nM of each DATP, dCTP, dGTP and dTTP; 0.08 units/reaction RNase inhibitor (20 U/μl, Perkin Elmer, Boston Mass.); ¹/₂₅ volume of Qiagen Enzyme mix; 300 nM each forward and reverse primer; to make a total reaction volume of 25 ml. The thermocycling conditions consisted of: 1 cycle 50° C. for 30 minutes; 1 cycle of 95° C. for 15 minutes; 35 cycles of 57° C. for 30 seconds, 72° C. for 45 seconds, 94° C. for 45 seconds; 1 cycle of 57° C. for 30 seconds; 1 cycle of 72° C. for 10 minutes and a 4° C. hold.

b. RT and PCR-2 Step Reaction b1. Reverse Transcription: Random primed cDNA was generated in the following way: 2 μl of 50 μM random hexamers were added to 6 μl of RNA extract. This was heated to 70° C. for 5 minutes and quickly chilled on ice. Then 32 μl of a master mix containing 5 mM MgCl$_2$ (Perkin Elmer), 1× Perkin Elmer Buffer II (50 mM KCl, 10 mM Tris-HCl, (pH 8.3 at room temperature)), 1 mM dNTPs (Perkin Elmer), 1 U/μl RNase Inhibitor (20 U/μl, Perkin Elmer), and 25 U/μl MuLV RT (murine leukemia virus reverse transcriptase; Perkin Elmer). The thermocyling conditions consisted of: 1 cycle of 22° C. for 10 minutes; 1 cycle of 42° C. for 15 minutes; 1 cycle of 95° C. for 10 minutes, 1 cycle of 5° C. for 5 minutes and hold at 4° C.

b2. PCR: Reactions tube containing 40 μl of 5 mM MgCl$_2$ (Perkin Elmer), 1× Perkin Elmer Buffer II, 300 nM forward primer, 300 nM reverse primer, and 0.25 U/μl Amplitaq Polymerase (Perkin Elmer) was added to 10 μl cDNA obtained from the reverse transcription (paragraph b1, above). Alternatively, to amplify longer section of random primed cDNA, Expand Long Template PCR Kit (Boehringer Mannheim, Indianapolis, Ind.) was used. The thermocycling conditions consisted of: 1 cycle of 93° C. for 4 minutes; 35 cycles of 57° C. for 30 seconds, 72° C. for 45 seconds, 93° C. for 45 seconds; 1 cycle of 57° C. for 30 seconds; 1 cycle of 72° C. for 10 minutes and a 4° C. hold. (Annealing temperature would vary according to the primer pair utilyzed to amplify cDNA).

3. The Results of Each PCR were Evaluated and Prepared for DNA Sequencing.

Sequence analysis was performed by the Advanced Genetic Analysis Center (AGAC) (University of Minnesota, Minneapolis, Minn.). using an ABI Model 377 DNA Sequencer.

I. Evaluation of PCR Reactions on an Agarose Gel.

One gram of agarose was added to 100 ml of 1× TAE buffer. This was microwaved for 2 minutes, and 4 μl of 10 mg/ml EtBr was added to every 100 ml agarose. The gel was cast and allowed to solidify for about 15–30 minutes. Four μl of PCR product were mixed with 1 μl loading dye and added to the gel, which was run at 140 volts for 1 hour or 75 volts for 2 hours.

II. Purification of PCR Product with Qiagen Qiaquick PCR Purification Kit

For each sample to be purified, a column was placed into a collection tube. One hundred μl PB buffer were added to the 20 μl PCR reaction left in PCR tube, and mixed thoroughly. All of the PCR product/PB buffer mix was added to the column, and the column was spun for 1 minute at full speed in an Eppendorf microfuge. The flow-through from collection tube was discarded, and the column was placed back in the tube. Seven hundred and fifty μl of PE buffer was added, and the column spun for another minute at full speed. After discarding the flow-through from collection tube, the column was spun for another minute at full speed to remove any residual PE buffer from the column. The column was transferred into a clean, microfuge tube, and 30 μl H$_2$O was added to the column and incubated for at least a minute at room temp. The column was spun for one minute at full speed. The PCR product/H$_2$O eluate in the microfuge tube and was ready to be added to the sequencing reaction.

Example 4

Detection of European-like PRRSV

In this example, viral DNAs were amplified using primers that amplify European-like PRRSV, European PRRSV, and North American PRRSV. The amplified region included the deletion that is present in European-like PRRSV.

The viral RNA of Lelystad was obtained from supernatants of infected MA-104 cells, the viral RNA of VR-2332 was obtained from supernatants of infected MA-104 cells, and the viral RNA from European-like PRRSV was obtained from supernatants of infected primary porcine alveolar macrophages, cDNA of viral RNA was prepared as described above in Example 3.

The viral cDNAs were amplified using the primers Euro1671/: 5'-GCCTGTCCTAACGCCAAGTAC (SEQ ID NO:16) and/Euro3165-rc: 5'-CATGTCCACCCTATCCCA-CAT (SEQ ID NO:17). The amplification conditions are listed in Table 2.

TABLE 2

General PCR Conditions (for 50 uL reaction)

| Component | Stock Concentration | Final Conc |
|---|---|---|
| MgCl$_2$ | 25 mM | 5 mM |
| Buffer II[1] | 10 X | 1 X |
| Forward Primer | 15 uM | 0.3 uM |
| Reverse Primer | 15 uM | 0.3 uM |
| Taq Polymerase | 5 U/ul | 0.25 U/ul |

[1]Buffer II, manufactured by Perkin Elmer.

RESULTS

Amplification of viral DNA from Lelystad, VR-2332, and European-like resulted in amplification products that migrated at the predicted molecular weights. As expected, the product of amplifying the European-like DNA migrated at about 1.5 kilobases, approximately 51 base pairs less than Lelystad.

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described for variations obvious to one skilled in the art will be included within the invention defined by the claims.

All headings are for the convenience of the reader and should not be used to limit the meaning of the text that follows the heading, unless so specified.

| Sequence Listing Free Text | |
|---|---|
| SEQ ID NO: 1 | Portion of nucleotide sequence of a porcine reproductive and respiratory syndrome virus |
| SEQ ID NOs: 2–10 | Polypeptides predicted from open reading frames of SEQ ID NO: 1. |
| SEQ ID NO: 11 | Nucleotides 1,981 to 2,820 of the Lelystad virus |
| SEQ ID NOs: 12–17 | Primer |
| SEQ ID NO: 18 | Oligonucleotide |
| SEQ ID NOs: 19–21 | Primer |

What is claimed is:

1. A method for detecting the presence of a European-like PRRSV, comprising:

contacting a viral polynucleotide with a first primer and a second primer under conditions suitable to form a detectable amplification product, wherein the first primer comprises a nucleotide sequence that is complementary to a portion of SEQ ID NO:1 that comprises nucleotides 2268 and 2269 of SEQ ID NO:1 or the complement thereof; and detecting an amplification product, wherein the detection indicates that the viral polynucleotide is a European-like PRRSV.

2. The method of claim 1 wherein the first primer comprises a nucleotide sequence selected from the group consisting of 5'ATCGGGAATGCTCAGTCCCCTT (SEQ ID NO:12), and 5'-AAGGGGACTGAGCATTCCCG (SEQ ID NO:14).

3. A method for detecting the presence of a European-like PRRSV in a porcine subject comprising:

contacting a biological sample obtained from a porcine subject with a first primer and a second primer and incubating under conditions suitable to form a detectable amplification product, wherein the first primer comprises a nucleotide sequence that is complementary to a portion of SEQ ID NO:1 that comprises nucleotides 2268 and 2269 of SEQ ID NO: 1 or the complement thereof; and detecting an amplification product, wherein the detection indicates that the porcine subject has a European-like PRRSV.

4. The method of claim 3 wherein the first primer comprises a nucleotide sequence selected from the group consisting of 5'ATCGGGAATGCTCAGTCCCCTT (SEQ ID NO:12), and 5'-AAGGGGACTGAGCATTCCCG (SEQ ID NO:14).

5. The method of claim 3 wherein the biological sample comprises lung tissue.

6. A kit for use in detecting PRRSV in a porcine subject, the kit comprising the first primer and a second primer of claim 1 or 3 for use in amplification of a portion of a PRRSV and instructions for using the primer pair.

* * * * *